(12) United States Patent
Havran et al.

(10) Patent No.: US 7,420,083 B2
(45) Date of Patent: Sep. 2, 2008

(54) SUBSTITUTED ARYLOXIMES

(75) Inventors: Lisa Marie Havran, Florence, NJ (US); John Anthony Butera, Clarksburg, NJ (US); Hassan Mahmoud Elokdah, Yardley, PA (US); Douglas John Jenkins, Collegeville, PA (US); Eric Gould Gundersen, Royersford, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/948,611

(22) Filed: Sep. 23, 2004

(65) Prior Publication Data

US 2005/0070584 A1 Mar. 31, 2005

Related U.S. Application Data

(60) Provisional application No. 60/505,801, filed on Sep. 25, 2003.

(51) Int. Cl.
C07C 63/06 (2006.01)
A61K 31/19 (2006.01)
(52) U.S. Cl. .................. 562/440; 514/568; 514/570
(58) Field of Classification Search ............... 562/440; 514/568, 570
See application file for complete search history.

(56) References Cited

U.S. PATENT DOCUMENTS

| | | | |
|---|---|---|---|
| 3,026,325 A | 3/1962 | Heinzelman et al. | 548/496 |
| 3,476,770 A | 11/1969 | Scherrer | 548/494 |
| 3,557,142 A | 1/1971 | Bell | 548/516 |
| 3,843,683 A | 10/1974 | Bell | 548/493 |
| 4,478,819 A | 10/1984 | Hercelin et al. | 424/457 |
| 4,736,043 A | 4/1988 | Michel et al. | 548/492 |
| 4,851,406 A | 7/1989 | Mertens et al. | 514/217.04 |
| 5,164,372 A | 11/1992 | Matsuo et al. | 514/19 |
| 5,393,920 A * | 2/1995 | Benoit et al. | 562/440 |
| 5,420,289 A | 5/1995 | Musser et al. | 548/159 |
| 5,482,960 A | 1/1996 | Berryman | 514/414 |
| 5,502,187 A | 3/1996 | Ayer et al. | 544/117 |
| 5,541,343 A | 7/1996 | Himmelsbach et al. | 514/424 |
| 5,599,663 A | 2/1997 | Vaughan | 435/6 |
| 5,612,360 A | 3/1997 | Boyd et al. | 514/381 |
| 5,859,044 A | 1/1999 | Dow et al. | 514/419 |
| 6,048,875 A | 4/2000 | De Nanteuil et al. | 514/314 |
| 6,054,621 A * | 4/2000 | Gayer et al. | 568/20 |
| 6,103,907 A * | 8/2000 | Yanagisawa et al. | 546/329 |
| 6,110,963 A | 8/2000 | Malamas | 514/443 |
| 6,166,069 A | 12/2000 | Malamas et al. | 514/414 |
| 6,177,463 B1 * | 1/2001 | Gerdes et al. | 514/524 |
| 6,194,464 B1 * | 2/2001 | Kuhnt et al. | 514/609 |
| 6,221,865 B1 | 4/2001 | Sebti et al. | 514/235.5 |
| 6,232,322 B1 | 5/2001 | Malamas et al. | 514/303 |
| 6,251,936 B1 | 6/2001 | Wrobel et al. | 514/443 |
| 6,302,837 B1 | 10/2001 | De Nanteuil et al. | 514/337 |
| 6,479,524 B1 | 11/2002 | Priepke et al. | 514/352 |
| 6,599,929 B2 | 7/2003 | Cho et al. | 514/415 |
| 6,787,556 B1 | 9/2004 | Hargreaves et al. | 514/311 |
| 6,800,645 B1 | 10/2004 | Cox et al. | 514/314 |
| 6,800,654 B2 | 10/2004 | Mayer et al. | 514/381 |
| 6,844,358 B2 | 1/2005 | Malamas et al. | 514/336 |
| 2003/0013732 A1 | 1/2003 | Elokdah | 514/301 |
| 2003/0018067 A1 | 1/2003 | Elokdah et al. | 514/469 |
| 2003/0060497 A1 | 3/2003 | Gerlach et al. | 514/414 |
| 2003/0125371 A1 | 7/2003 | Elokdah et al. | 514/419 |
| 2004/0116488 A1 | 6/2004 | Jennings et al. | 514/374 |
| 2004/0116504 A1 | 6/2004 | Elokdah et al. | 514/419 |
| 2004/0122070 A1 | 6/2004 | Jennings | 514/374 |
| 2004/0138283 A1 | 7/2004 | Jennings et al. | 514/414 |
| 2004/0204417 A1 | 10/2004 | Perez et al. | 514/249 |
| 2005/0070585 A1 | 3/2005 | Elokdah et al. | 514/364 |
| 2005/0070587 A1 | 3/2005 | Elokdah et al. | 514/381 |
| 2005/0070592 A1 | 3/2005 | Gundersen | 514/415 |
| 2005/0096377 A1 | 5/2005 | Hu | 514/419 |
| 2005/0113428 A1 | 5/2005 | Gopalsamy et al. | 514/364 |
| 2005/0113436 A1 | 5/2005 | Elokdah et al. | 514/411 |
| 2005/0113438 A1 | 5/2005 | Hu et al. | 514/414 |
| 2005/0113439 A1 | 5/2005 | Hu | 514/414 |
| 2005/0119296 A1 | 6/2005 | Elokdah et al. | 514/300 |
| 2005/0119326 A1 | 6/2005 | Havran et al. | 514/414 |
| 2005/0119327 A1 | 6/2005 | Hu | 514/414 |
| 2005/0215626 A1 | 9/2005 | Havran et al. | 514/469 |
| 2007/0167490 A1 | 7/2007 | Ishida et al. | 514/338 |

FOREIGN PATENT DOCUMENTS

| | | |
|---|---|---|
| DE | 3147276 A1 | 11/1981 |
| DE | 43 38 770 A1 | 5/1995 |
| DE | 19543639 A1 | 5/1997 |
| DE | 19753522 | 6/1999 |
| EP | 0 416 609 A2 | 3/1991 |
| EP | 0 508 723 A1 | 10/1992 |
| EP | 0 512 570 A1 | 11/1992 |
| EP | 0 540 956 A1 | 5/1993 |
| EP | 0 564 984 A2 | 10/1993 |
| EP | 0 655 439 A2 | 5/1995 |
| EP | 0 759 434 A1 | 2/1997 |
| EP | 0 819 686 A1 | 1/1998 |
| EP | 0 822 185 A1 | 2/1998 |
| EP | 708 098 B1 | 3/1999 |
| EP | 0 916 651 A1 | 5/1999 |

(Continued)

OTHER PUBLICATIONS

Krishnamurti, C. et al., "Plasminogen Activator Inhibitor: A Regulator of Ancrod-Induced Fibrin Deposition in Rabbits," *Blood*, 69(3): 798-803 (Mar. 1987).

Reilly, C. et al., "Both Circulating and Clot-Bound Plasminogen Activator-1 Inhibit Endogenous Fibrinolysis in the Rat," *Arteriosclerosis and Thrombosis*, 11(5): 1276-1286 (Sep./Oct. 1991).

(Continued)

*Primary Examiner*—Shailendra Kumar
(74) *Attorney, Agent, or Firm*—Mabel Ng

(57) ABSTRACT

The present invention relates to substituted aryl oximes and methods of using them.

21 Claims, No Drawings

FOREIGN PATENT DOCUMENTS

| | | | |
|---|---|---|---|
| EP | 0 955 299 | A1 | 11/1999 |
| EP | 1 092 716 | | 4/2001 |
| EP | 1 156 045 | A1 | 11/2001 |
| EP | 1 354 602 | A1 | 10/2003 |
| FR | 2 244 499 | A1 | 4/1975 |
| FR | 2 777 886 | A1 | 10/1999 |
| FR | 2 799 756 | A1 | 4/2001 |
| GB | 1 321 433 | | 6/1973 |
| JP | 7-41459 | | 2/1995 |
| JP | 11-193272 | | 7/1999 |
| JP | 2000-344748 | | 12/2000 |
| WO | 96/21656 | A1 | 7/1986 |
| WO | 94/13637 | A1 | 6/1994 |
| WO | 94/14434 | A1 | 7/1994 |
| WO | 94/26738 | A1 | 11/1994 |
| WO | 95/10513 | A1 | 4/1995 |
| WO | WO 95/24383 | A1 | 9/1995 |
| WO | WO 95/29907 | A1 | 11/1995 |
| WO | 96/06840 | A1 | 3/1996 |
| WO | WO 96/07636 | A1 | 3/1996 |
| WO | 96/26207 | A1 | 8/1996 |
| WO | WO 96/32379 | A1 | 10/1996 |
| WO | WO 97/07096 | A1 | 2/1997 |
| WO | 97/09308 | A1 | 3/1997 |
| WO | WO 97/37970 | A1 | 10/1997 |
| WO | 97/43260 | A1 | 11/1997 |
| WO | 97/48697 | A1 | 12/1997 |
| WO | 98/08818 | A1 | 3/1998 |
| WO | WO 98/50029 | A1 | 11/1998 |
| WO | 99/28297 | A1 | 6/1999 |
| WO | 99/43672 | A1 | 9/1999 |
| WO | 99/46260 | A1 | 9/1999 |
| WO | WO 99/43651 | A2 | 9/1999 |
| WO | WO 99/43654 | A2 | 9/1999 |
| WO | 99/50268 | A1 | 10/1999 |
| WO | 99/58519 | A1 | 11/1999 |
| WO | 99/61435 | A1 | 12/1999 |
| WO | 00/32180 | A2 | 6/2000 |
| WO | 0/35919 | A1 | 6/2000 |
| WO | 00/46195 | A1 | 8/2000 |
| WO | 00/46197 | A1 | 8/2000 |
| WO | 00/64876 | A1 | 11/2000 |
| WO | 00/64888 | A1 | 11/2000 |
| WO | 01/12187 | A2 | 2/2001 |
| WO | WO 02/24633 | A1 | 3/2002 |
| WO | 02/030895 | A1 | 4/2002 |
| WO | 02/072549 | A1 | 9/2002 |
| WO | 03/000253 | A1 | 1/2003 |
| WO | 03/031409 | A1 | 4/2003 |
| WO | 03/068742 | A1 | 8/2003 |
| WO | 03/087087 | A2 | 10/2003 |
| WO | 2004/052854 | A2 | 6/2004 |
| WO | WO 2004/080947 | A1 | 9/2004 |

OTHER PUBLICATIONS

Carmeliet, P. et al., "Plasminogen Activator Inhibitor-1 Gene-deficient Mice," *Journal of Clinical Investigation*, 92: 2756-2760 (Dec. 1993).

Rocha, E. et al., "The Relationship Between Impaired Fibrinolysis and Coronary Heart Disease," *Fibrinolysis*, 8: 294-303 (1994).

Aznar, J. et al., "Role of Plasminogen Activator Inhibitor Type 1 in the Pathogenesis of Coronary Artery Diseases," *Haemostasis* 24: 243-251 (1994).

Biemond, B. J. et al., "Thrombolysis and Reocclusion in Experimental Jugular Vein and Coronary Artery Thrombosis," *Circulation*, 91: 1175-1181 (1995).

Levi, M. et al., "Inhibition of Plasminogen Activator Inhibitor-1 Activity Results in Promotion of Endogenous Thrombolysis and Inhibition of Thrombus Experimental Thrombosis," *Circulation* 85:305-312 (1992).

Nordt, T. K. et al., "Differential Regulation by Troglitazone of Plasminogen Activator Inhibitor Type 1 in Human Hepatic and Vascular Cells," *Journal of Clinical Endocrinology and Metabolism*, 85(4):1563-1568 (2000).

Daci, E. et al., "Mice Lacking the Plasminogen Activator Inhibitor 1 are Protected from Trabecular Bone Loss Induced by Estrogen Deficiency," *Journal of Bone and Mineral Research*, 15(8):1510-1516 (Nov. 8, 2000).

Schneiderman J. et. al., "Increased type 1 plasminogen activator inhibitor gene expression in atherosclerotic human arteries," *Proc Natl Acad Sci* 89: 6998-7002 (Aug. 1992).

Juhan-Vague, I. et. al., "Deficient t-PA Release and Elevated PA Inhibitor Levels in Patients with Spontaneous or Recurrent Deep Venous Thrombosis," *Thromb Haemost* 57: 67-72 (1987).

Juhan-Vague, I. et. al., "PAI-1, Obesity, Insulin Resistance and Risk of Cardiovascular Events," *Thromb Haemost* 78: 565-660 (1997).

Hamsten, A. et. al., "Plasminogen Activator Inhibitor in Plasma: Risk Factor For Recurrent Myocardial Infarction," *Lancet* 2: 3-9 (Jul. 4, 1987).

Siemens, H. J. et. al., "Course of Molecular Hemostatic Markers During and After Different Surgical Procedures," *J Clin Anesthesia* 11: 622-629 (Dec. 1999).

Koh, K. et. al., "Effects of Hormone-Replacement Therapy on Fibrinolysis in Postmenopausal Women," *N Engl J Med* 336(10): 683-690 (Mar. 6, 1997).

Ley, J. P. et al., "Hydroxy- or Methoxy-Substituted Benzaldoximes and Benzaldehyde-*O*-alkyloximes as Tyrosinase Inhibitors," *Bioorganic & Medicinal Chemistry*, 2001, 9:1879-1885.

Yoshikawa, H. et al., "Benzaldehyde O-Alkyloximes as New Plant Growth Regulators," *BioSci. Biotechnol. Biochem.*, 62(5), pp. 996-997, 1998.

Yoshikawa, H. et al., "Synthesis and Biological Activity of Benzaldehyde o-Alkyloximes as Abscisic Acid Mimics (Part I)," *BioSci. Biotechnol. Biochem.*, 56(2), pp. 256-260, 1992.

Van Dijk, J. et al., "Oxime ether derivatives, a new class of nonsteroidal antiinflammatory compounds," *J Med Chem*, 20(9), pp. 1199-1206 (Sep. 1977).

Takamura, M. et al., "Synthesis and biological activity of novel α-substituted β-phenylpropionic acids having pyridine-2-ylphenyl moiety as antihyperglycemic agents," Bioorganic and Medicinal Chemistry, Mar. 9, 2004, 12(9):2419-2439.

U.S. Appl. No. 10/947,710, filed Sep. 23, 2004, Commons et al.

U.S. Appl. No. 10/947,711, filed Sep. 23, 2004, Gopalsamy et al.

U.S. Appl. No. 11/208,777, filed Aug. 22, 2005, Commons et al.

U.S. Appl. No. 11/208,772, filed Aug. 22, 2005, Commons

U.S. Appl. No. 11/208,775, filed Aug. 22, 2005, Commons et al.

Aggarwal et al., "A catalytic antibody programmed for torsional activation of amide bond hydrolysis," *Chem. Eur. J.*, Jan. 25, 2003, 9(13), 3132-3142.

Ballantine, J. A., "The Chemistry of Bacteria," *Journal of the Chemical Society Abstracts*, 1957, 2222-2227.

Charlton, Peter, "The status of plasminogen activator inhibitor-1 as a therapeutic target," *Expert Opinion On Investigational Drugs*, May 1997, 6(5), 539-554.

Crandall, D. L. et al., "Characterization and comparative evaluation of a structurally unique PAI-1 inhibitor exhibiting oral in-vivo efficacy," *Journal of Thrombosis and Haemostasis*, Mar. 17, 2004, 2, 1422-1428.

Da Settimo, A. et al., "Reaction of indole derivatives with bromine, substitution, oxidation, and dimerization," J Org Chem, 1970, 35(8):2546-2551.

Delgado et al., Journal of Organic Chemistry (1993), 58(10), pp. 2862-2866.

Dillard R. D. et al., "Indole Inhibitors of Human Nonpancreatic Secretory Phospholipase A₂ 1. Indole-3-Acetamides" , *Journal of Medicinal Chemistry*, American Chemical Society, 39(26), 5119-5136.

Guzzo, P.R. et al., "Synthesis of a conformationally constrained threonin-valine dipeptide mimetic: design of a potential inhibitor of plasminogen activator inhibitor-1," *Tetrahedron Letters*, 2002 43(1), 41-43.

Hipskind, P. A. et al., "Potent and selective 1,2,3-trisubstituted indole NPY Y-1 antagonists," *J Med Chem*, 40(23), 3712-3714.

Julia et al., CA 57:49169, 1962.

Malamas, M. S. et al., "Antihyperglycemic activity of new 1,2,4-oxadiazolidine-3,5-diones," *Eur. J. Med. Chem.*, 2001, 36, 31-42.

Malamas, M.S. et al. "Novel benzofuran and benzothiophene biphenyls as inhibitors of protein tyrosine phosphatase 1B with antihyperglycemic properties," *Journal of Medicinal Chemistry*, Apr. 6, 2000, 43(7), 1293-1310.

Moody et al., CA 120:298300, 1994.

Shengeliya, M. S. et al., "N-Glycosides of 5-amino-2-(ethoxycarbonyl)indole," *Zhurnal Organicheskoi Khimii*, 1986, 22(9), 1868-1873.

Albers, "Advances in intravenous thrombolytic therapy for treatment of acute stroke," *Neurology*, 2001, 57(suppl 2), S77-S81.

Ashitani et al., "Elevated Plasma Procoagulant and Fibrinolytic Markers in Patients with Chronic Obstructive Pulmonary Disease," *Internal Medicine*, 2002, 41(3), 181-185.

Atiomo et al., "Immunohistochemical detection of plasminogen activator inhibitor-1 in polycystic ovaries," *Gynecol Endocrinol*, 2000, 14, 162-168.

Aznar, "Role of Plasminogen Activator Inhibitor Type 1 in the Pathogenesis of Coronary Artery Dieseases," *Haemostasis*, 1994, 24, 243.

Berry et al., "Antithrombotic activity of a monoclonal antibody inducing the substrate form of plasminogen activator inhibitor type 1 in rat models of venous and arterial thrombosis," *British Journal of Pharmacology*, 1998, 125, 29-34.

Bianchi et al., "Immunohistochemical Localization of the Plasminogen Activator Inhibitor-1 in Breast Cancer," *International Journal of Cancer*, 1995, 60(5), 597-603.

Biemond, "Thrombolysis and Reocclusion in Experimental Jugular Vein and Coronary Artery Thrombosis: Effects of a Plasminogen Activator Inhibitor Type 1-Neutralizing Monoclonal Antibody," *Circulation*, 1995, 91, 1175.

Carmeliet et al., "Biological Effects of Disruption of the Tissue-Type Plasminogen Activator, Urokinase-Type Plasminogen Activator, and Plasminogen Activator Inhibitor-1 Genes in Mice," *Ann. NY Acad Sci*, 1995, 748, 367-381.

Carmeliet, "Plasminogen Activator Inhibitor-1 Gene-deficient Mice: II. Effects on Hemostasis, Thrombosis, and Thrombolysis," *Journal of Clinical Investigation*, 1993, 92, 2756-2760.

Chazaud et al., "Promigratory Effect of Plasminogen Activator Inhibitor-1 on Invasive Breast Cancer Cell Populations," *American Journal of Pathology*, 2002, 160(1), 237-246.

Daci, "Mice Lacking the Plasminogen Activator Inhibitor 1 Are Protected from Trabecular Bone Loss Induced by Estrogen Deficiency," *Journal of Bone and Mineral Research*, 2000, 15(8), 1510.

Egelund et al., "A Regulatory Hydrophobic Area in the Flexible Joint Region of Plasminogoen Activator Inhibitor-1, Defined with Fluorescent Activity-neutralizing Ligands," *Journal of Biological Chemistry*, 2001, 276(16), 13077-13086.

Exley et al., "Plasmin cleaves Aβ42 in vitro and prevents its aggregation into β-pleated sheet structures," *Neuroreport*, 2001, 12, 2967-2970.

Fay et al., "Human Plasminogen Activator Inhibitor-1 (PAI-1) Deficiency: Characterization of a Large Kindred with a null Mutation in the PAI-1 Gene," *Blood*, 1997, 90, 204-208.

Frandsen et al., "Plasminogen activator inhibitor type 1 (PAI-1) in cancer: a potential new target for antiinvasive and antimetastatic therapy," *Drugs of the Future*, 1998, 23(8), 873-883.

Glueck et al., "Continuing metformin throughout pregnancy in women with polycystic ovary syndrome appears to safely reduce first-trimester spontaneous abortion: a pilot study," *Fertility and Sterility*, 2001, 75(1), 46-52.

Hamano et al., "Expression of Glomerular Plasminogen Activator Inhibitor Type 1in Glomerulonephrtis," *American Journal of Kidney Diseases*, 2002, 39(4), 695-705.

Hamsten, A. et al., "Plasminogen Activator Inhibitor in Plasma: Risk Factor for Recurrent Myocardial Infarction," *Lancet*, 1987, 2, 3-9.

Isogai et al., "Plasminogen Activator Inhibitor-1 Promotes Angiogenesis by Stimulating Endothelial Cell Migration toward Fibronectin," *Cancer Research*, 2001, 61(14), 5587-5594.

Juhan-Vague, I. et al., "Deficient t-PA Release and Elevated PA Inhibitor Levels in Patients with Spontaneous of Recurrent Deep Venous Thrombosis," *Thromb Haemost*, 1987, 57, 67-72.

Juhan-Vague, I. et al., "PAI-1, Obesity, Insulin Resistance and Risk of Cardiovascular Events," *Thromb Haemost*, 1997, 78, 565-660.

Kim et al., "Nonproteolytic Neuroprotection by Human Recombinant Tissue Plasminogen Activator," *Science*, 1999, 284, 647-650.

Kingston et al., "In Vitro stimulation of tissue-type plasminogen activator by Alzheimer amyloid β-peptide analogues," *Nat. Med.*, 1995, I. 138-142.

Koh, K. et. al, "Effects of Hormone-Replacement Therapy on Fibrinolysis in Postmenopausal Women," *N Engl J Med*, 1997, 336, 683-690.

Krishnamurti, "Plasminogen Activator Inhibitor: A Regulator of Ancrod-Induced Fibrin Deposition in Rabbits," *Blood*, 1987, 69, 798-803.

Lahlou et al., "Chronic Graft Dysfunction in Renal Transplant Patients," *Transplantation*, 2002, 73, 1290-1295.

Lahlou et al., "Chronic Graft Dysfunction in Renal Transplant Patients," *Transplantation*, 2002, 73, 1290-1295.

Levi, "Inhibition of Plasminogen Activator Inhibitor-1 Activity Results in Promotion of Endogenous Thrombolysis and Inhibition of Thrombus Extension in Models of Experimental Thrombosis," *Circulation*, 1992, 85, 305.

Look et al., "Pooled Analysis of prognostic Impact of Urokinase-Type Plasminogen Activator and its Inhibitor PAI-1 in 8377 Breast Cancer Patients," *Journal of the National Cancer Institute*, 2002, 94(2), 116-128.

Malamas, M. S. et al., "Antihyperglycemic activity of new 1,2,4-oxadiazolidine-3,5-diones," *Eur. J. Med. Chem.*, 2001, 36, 31-42.

Malamas, M. S. et al., "New Azolidinediones as Inhibitors of Protein Tyrosine Phosphatase 1B with Antihypergylcemic Properties," *J. Med. Chem.*, 2000, 43, 995-1010.

McGeer et al., "The inflammatory response system of brain: implications for therapy of Alzheimer and other neurodegenerative diseases," *Brain Res. Rev.*, 1995, 21, 195-218.

Melchor et al., "The Tissue Plasminogen Activator-Plasminogen Proteolytic Cascade Accelerates Amyloid-β(Aβ) Degredation and Inhibits Aβ-Induced Neurodengenration," *J. Neurosci.*, 2003, 23, 8867-8871.

Nordt, "Differential Regulation by Troglitazone of Plasminogen Activator Inhibitor Type 1 in Human Hepatic and Vascular Cells," *Journal of clinical Endocrinology and Metabolism*, 2000, 85(4), 1563.

Periz et al., "Proteolysis in Alzheimer's disease: Can plasmin tip the balance?" *EMBO Reports*, 2000, I, 477-478.

Qu et al., "Clinical significance of the expression of urokinase type plasminogen activator and plasminogen activator inhibitor in cervical carcinomas," *Zhongliu Fangzhi Zazhi*, 2003, 10(8), 821-824.

Reilly, "Both Circulating and Clot-Bound Plasminogen Activator Inhibitor-1 Inhibit Endogenous Fibrinolysis in the Rat," *Arteriosclerosis and Thrombosis*, 1991, 11, 1276.

Rocha, "The Relationship Between Impaired Fibrinolysis and Coronary Heart Disease: a Role for PAI-1," *Fibrinolysis*, 1994, 8, 294-303.

Roldan et al., "Hypofibrinolysis in atrial fibrillation," *American Heart Journal*, 1998, 136(6), 956-960.

Schneiderman, J. et al., "Increased type 1 plasminogen activator inhibitor gene expression in atherosclerotic human arteries," *Proc Natl Acad Sci*, 1992, 89, 6998-7002.

Seeds et al., "Neuronal migration is retarded in mice lacing the tissue plasminogen activator gene," *PNAS*, 1999, 96, 14118-14123.

Siemens, HJ et al., "Course of molecular hemostatic markers during and after different surgical procedures," *J Clin Anesthesia*, 1999, 11, 622-629.

Simons et al., "Cholesterol depletion inhibits the generation of β-amyloid in hippocampal neurons," *PNAS*, 1998, 95, 6460-6464.

Sobel, "The Potential Influence of Insulin and Plasminogen Activator Inhibitor Type 1 on the Formation of Vulnerable Atherosclerotic Plaques Associated with Type 2 Diabetes." *Proceedings of the Association of American Physicians*, 1999, 111(4), 313-318.

Takanashi et al., "Insulin Resistance and Changes in the Blood Coagulation-Fibrinolysis System After a Clucose Clamp Technique in Patients with Type 2 *Diabetes mellitus*," *Journal of Medicine*, 2000, 31(1 & 2), 45-62.

Takazoe et al., "Increased plasminogen activator inhibitor activity and diabetes predict subsequent coronary events in patients with angina pectoris," *Ann Med*, 2001, 33, 206-212.

Thogersen et al., "High Plasminogen Activator Inhibitor and Tissue Plasminogen Activator Levels in Plasma Precede a First Acute Myocardial Infarction in Both Men and Women: Evidence for the Fibrinolytic System as an Independent Primary Risk Factor," *Circulation*, 1998, 98, 2241-2247.

Tsirka et al., "An Extracellular Proteolytic Cascade Promotes Neuronal Degeneration in the Mouse Hippocampus," *J. Neurosci.*, 1997, 17, 543-552.

Tucker et al., "Tissue Plasminogen Activator Requires Plasminogen to Modulate Amyloid-β Neurotoxicity and Deposition," *J. Neurochem.*, 2000, 75, 2172-2177.

Tucker et al., "The Plasmin System is Induced by and Degrades Amyloid-β Aggregates," *J. Neurosci.*, 2000, 20, 3937-3946.

Tucker et al., "Urokinase-Type Plasminogen Activator Inhibits Amyloid-β Neurotoxicity and Fibrillogenesis Via Plasminogen," *J. Neurosci. Res.*, 2002, 70, 249-255.

Van Nostrand et al., "Plasmin Cleavage of Amyloid β-Protein: Alteration of Secondary Structure and Stimulation of Tissue Plasminogen Activator Activity," *Biochemistry*, 1999, 38, 11570-11576.

Wind et al., "Epitope mapping for four monoclonal antibodies against human plasminogen activator inhibitor type-1," *European Journal of Biochemistry*, 2001, 268(4), 1095-1106.

Wnendt et al., "Amyloid β Peptides Stimulate Tissue-Type Plasminogen Activator But Not Recombinant Prourokinase," *Thromb. Res.*, 1997, 8, 217-224.

Zhao et al., "Immunohistochemical Expression of uPA, PAI-1, Cathepsin D and Apoptotic Cells in Ductal Carcinoma in situ of the Breast," *Breast cancer*, 2002, 9(2), 118-26.

* cited by examiner

SUBSTITUTED ARYLOXIMES

CROSS-REFERENCE TO RELATED APPLICATIONS

This application claims the benefit of U.S. Provisional Application No. 60/505,801 filed Sep. 25, 2003, the entire disclosure of which is incorporated herein by reference.

BACKGROUND

The present invention relates generally to substituted aryl oximes and methods of using them.

The serine protease inhibitor PAI-1 is one of the primary inhibitors of the fibrinolytic system. The fibrinolytic system includes the proenzyme plasminogen, which is converted to the active enzyme, plasmin, by one of two tissue type plasminogen activators, t-PA or u-PA. PAI-1 is the principal physiological inhibitor of t-PA and u-PA. One of plasmin's main responsibilities in the fibrinolytic system is to digest fibrin at the site of vascular injury. The fibrinolytic system, however, is not only responsible for the removal of fibrin from circulation but is also involved in several other biological processes including ovulation, embryogenesis, intima proliferation, angiogenesis, tumorigenesis, and atherosclerosis.

Elevated levels of PAI-1 have been associated with a variety of diseases and conditions including those associated with impairment of the fibrinolytic system. For example, elevated levels of PAI-1 have been implicated in thrombotic diseases, e.g., diseases characterized by formation of a thrombus that obstructs vascular blood flow locally or detaches and embolizes to occlude blood flow downstream. (Krishnamurti, *Blood*, 69, 798 (1987); Reilly, *Arteriosclerosis and Thrombosis*, 11, 1276 (1991); Carmeliet, *Journal of Clinical Investigation*, 92, 2756 (1993), Rocha, *Fibrinolysis*, 8, 294, 1994; Aznar, *Haemostasis* 24, 243 (1994)). Antibody neutralization of PAI-1 activity resulted in promotion of endogenous thrombolysis and reperfusion (Biemond, *Circulation*, 91, 1175 (1995); Levi, *Circulation* 85, 305, (1992)). Elevated levels of PAI-1 have also been implicated in diseases such as polycystic ovary syndrome (Nordt, *Journal of clinical Endocrinology and Metabolism*, 85, 4, 1563 (2000)), bone loss induced by estrogen deficiency (Daci, *Journal of Bone and Mineral Research*, 15, 8, 1510 (2000)), cystic fibrosis, diabetes, chronic periodontitis, lymphomas, diseases associated with extracellular matrix accumulation, malignancies and diseases associated with neoangiogenesis, inflammatory diseases, vascular damage associated with infections, and diseases associated with increased uPA levels such as breast and ovarian cancer.

In view of the foregoing, there exists a need for the identification of inhibitors of PAI-1 activity and for methods of using the identified inhibitors to modulate PAI-1 expression or activity in a subject in order to treat disorders associated with elevated PAI-1 levels.

SUMMARY

The present invention provides substituted aryl oximes and methods of using them. In certain embodiments, substituted aryl oximes of the present invention include those compounds of the following formula:

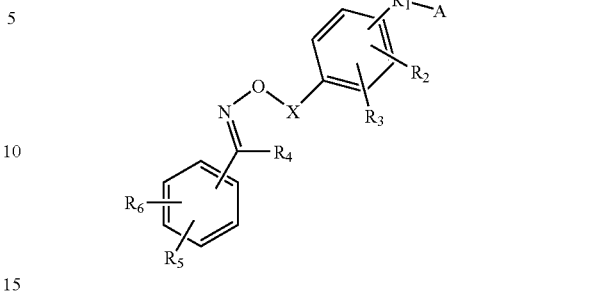

Formula 1 wherein:
  $R_1$ is a direct bond to A, $C_1$-$C_4$ alkylene, or —O—$C_1$-$C_4$ alkylene;
  $R_2$ and $R_3$ are, independently, hydrogen, halogen, $C_1$-$C_4$ alkyl, $C_1$-$C_3$ perfluoroalkyl, —O—$C_1$-$C_3$ perfluoroalkyl, $C_1$-$C_3$ alkoxy, —OH, —$NH_2$, —$NO_2$, aryl, heteroaryl, —O($CH_2$)$_p$-aryl, —O($CH_2$)$_p$-heteroaryl, —NH($CH_2$)$_p$-aryl, —NH($CH_2$)$_p$-heteroaryl, —NH(CO)-aryl, —NH(CO)-heteroaryl, —O(CO)-aryl, —O(CO)-heteroaryl, —NH(CO)—CH=CH-aryl, or —NH(CO)—CH=CH-heteroaryl;
  p is an integer from 0-6;
  $R_4$ is hydrogen, $C_1$-$C_8$ alkyl, or $C_3$-$C_6$ cycloalkyl;
  A is COOH or an acid mimic;
  X is $C_1$-$C_8$ alkylene, $C_3$-$C_6$ cycloalkylene, —($CH_2$)$_m$O—, or —($CH_2$)$_m$NH—;
  m is an integer from 1-6; and
  $R_5$ and $R_6$ are, independently, hydrogen, halogen, $C_1$-$C_6$ alkyl, $C_1$-$C_6$ perfluoroalkyl, —O—$C_1$-$C_6$ perfluoroalkyl, $C_1$-$C_6$ alkoxy, —OH, —$NH_2$, —$NO_2$, —O($CH_2$)$_n$-aryl, —O($CH_2$)$_n$-heteroaryl, aryl, or heteroaryl; and
  n is an integer from 0-6.

In certain exemplary embodiments, $R_1$ is a direct bond to A or $C_1$-$C_3$. $R_2$ may be hydrogen, halogen, $C_1$-$C_3$ alkyl, $C_1$-$C_3$ perfluoroalkyl, aryl, heteroaryl, —O—$C_1$-$C_3$ perfluoroalkyl, $C_1$-$C_3$ alkoxy, —OH, —O($CH_2$)$_p$-aryl, —NH(CO)-aryl or —NH(CO)-heteroaryl. $R_3$ may be hydrogen, halogen, $C_1$-$C_3$ alkyl, $C_1$-$C_3$ perfluoroalkyl, aryl, heteroaryl, —O—$C_1$-$C_3$ perfluoroalkyl, $C_1$-$C_3$ alkoxy, —OH, —O($CH_2$)$_p$-aryl, —NH(CO)-aryl or —NH(CO)-heteroaryl. $R_4$ may be hydrogen or $C_1$-$C_4$ alkyl. $R_5$ may be hydrogen, $C_1$-$C_8$ alkyl or $C_3$-$C_6$ cycloalkyl. $R_5$ may be hydrogen, halogen, $C_1$-$C_6$ alkyl, $C_1$-$C_6$ perfluoroalkyl, —O—$C_1$-$C_6$ perfluoroalkyl, or $C_1$-$C_6$ alkoxy. $R_6$ may be hydrogen, halogen, $C_1$-$C_6$ alkyl, $C_1$-$C_6$ perfluoroalkyl, —O—$C_1$-$C_6$ perfluoroalkyl, or $C_1$-$C_6$ alkoxy. A may be —COOH or tetrazole. X may be —$CH_2$—, —$CH_2$—$CH_2$—O—, or —$CH_2$—$CH_2$—$CH_2$—O—.

In some embodiments, when A is carboxylic acid, $R_1$ is a direct bond, unsubstituted $C_1$-$C_4$ alkylene, or —O—$C_1$-$C_4$ alkylene. In other embodiments, when A is carboxylic acid, $R_1$ is unsubstituted $C_1$-$C_4$ alkylene, or —O—$C_1$-$C_4$ alkylene.

The present invention also provides, inter alia, pharmaceutically acceptable salt or ester forms of compounds of formulas 1-3.

The present invention further provides, inter alia, methods of using substituted aryl oximes. In one aspect of the present invention, a therapeutically effective amount of one or more substituted aryl oximes is administered to a subject in order to treat a PAI-1 related disorder, e.g., by inhibiting PAI-1 activity in the subject. PAI-1 activity is associated with a number of diseases and conditions. For example, in one embodiment of the present invention, PAI-1 activity is associated with impairment of the fibrinolytic system. In other embodiments, PAI-1 activity is associated with thrombosis, e.g., venous thrombosis, arterial thrombosis, cerebral thrombosis, and deep vein thrombosis, atrial fibrillation, pulmonary fibrosis, thromboembolic complications of surgery, cardiovascular disease, e.g., myocardial ischemia, atherosclerotic plaque formation, chronic obstructive pulmonary disease, renal fibrosis, polycystic ovary syndrome, Alzheimer's disease, or cancer.

DETAILED DESCRIPTION

A. General Overview

The present invention provides compounds that inhibit PAI-1 activity, processes for preparing such compounds, pharmaceutical compositions containing such compounds, and methods for using such compounds in medical therapies. The compounds have properties that are useful for the treatment, including the prevention and inhibition, of a wide variety of diseases and disorders including those involving the production and/or action of PAI-1. These include disorders resulting from impairment of the fibrinolytic system including, but not limited to, thrombosis, coronary heart disease, renal fibrosis, atherosclerotic plaque formation, pulmonary disease, myocardial ischemia, atrial fibrillation, coagulation syndromes, thromboembolic complications of surgery, peripheral arterial occlusion and pulmonary fibrosis. Other disorders include, but are not limited to, polycystic ovary syndrome, Alzheimer's disease, and cancer.

The terms "alkyl" and "alkylene," as used herein, whether used alone or as part of another group, refer to substituted or unsubstituted aliphatic hydrocarbon chains, the difference being that alkyl groups are monovalent (i.e., terminal) in nature whereas alkylene groups are divalent and typically serve as linkers. Both include, but are not limited to, straight and branched chains containing from 1 to 12 carbon atoms, e.g. 1 to 8 carbon atoms, preferably 1 to 6 carbon atoms, more preferably 1 to 4 carbon atoms unless explicitly specified otherwise. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted. Representative optional substituents include, but are not limited to, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted aliphatic hydrocarbon chain and includes, but is not limited to, straight and branched chains having 2 to 10 carbon atoms (unless explicitly specified otherwise) and containing at least one double bond. Preferably, the alkenyl moiety has 1 or 2 double bonds. Such alkenyl moieties can exist in the E or Z conformations and the compounds of this invention include both conformations. Specifically included within the definition of "alkenyl" are those aliphatic hydrocarbon chains that are optionally substituted. Representative optional substituents include, but are not limited to, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Heteroatoms, such as O or S attached to an alkenyl should not be attached to a carbon atom that is bonded to a double bond.

The term "alkynyl", as used herein, whether used alone or as part of another group, refers to a substituted or unsubstituted aliphatic hydrocarbon chain and includes, but is not limited to, straight and branched chains having 2 to 10 carbon atoms (unless explicitly specified otherwise) and containing at least one triple bond. Preferably, the alkynyl moiety has 3 to 6 carbon atoms. In certain embodiments, the alkynyl can contain more than one triple bond and, in such cases, the alkenyl group must contain at least three carbon atoms. Specifically included within the definition of "alkynyl" are those aliphatic hydrocarbon chains that are optionally substituted. Representative optional substituents include, but are not limited to, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Heteroatoms, such as O or S attached to an alkynyl should not be attached to the carbon that is bonded to a triple bond.

The term "cycloalkyl" as used herein, whether alone or as part of another group, refers to a substituted or unsubstituted alicyclic hydrocarbon group having 3 to about 20 carbon atoms, preferably 3 to 6 carbon atoms (unless explicitly specified otherwise). Specifically included within the definition of "cycloalkyl" are those alicyclic hydrocarbon groups that are optionally substituted. For example, in certain embodiments of the present invention, the rings of the cycloalkyl can be optionally substituted by 1 to 3 groups selected from halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —$NH_2$, or —$NO_2$.

The term "aryl", as used herein, whether used alone or as part of another group, is defined as a substituted or unsubstituted aromatic hydrocarbon ring group having 5 to about 50 carbon atoms with from about 6 to about 14 carbon atoms being preferred. The "aryl" group can have a single ring or multiple condensed rings. The term "aryl" includes, but is not limited to phenyl, α-naphthyl, β-naphthyl, biphenyl, anthryl, tetrahydronaphthyl, fluorenyl, indanyl, biphenylenyl, and acenaphthenyl. Specifically included within the definition of "aryl" are those aromatic groups that are optionally substituted. Accordingly, the aryl groups described herein refer to both unsubstituted or substituted aryl groups. For example, in representative embodiments of the present invention, the, "aryl" groups are optionally substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. Exemplary substituents on the aryl groups herein include alkyl, alkoxy, halo, cyano, nitro, trihalomethyl, and thioalkoxy. In certain embodiments of the present invention, the rings of the aryl groups can be optionally substituted by 1 to 3 groups selected from halogen, $C_1$-$C_6$ alkyl, $C_1$-$C_6$ perfluoroalkyl, —O—$C_1$-$C_6$ perfluoroalkyl, $C_1$-$C_6$ alkoxy, —OH, —$NH_2$, —$NO_2$, —CN, aryl, —O-aryl, —NH-aryl, —NH—CO-alkyl, or —NH—CO-aryl. Aryl may suitably be substituted by one or more substituents selected from $C_1$-$C_4$ alkyl, —O—$C_1$-$C_4$ alkyl, $CF_3$, phenyl, —$OCF_3$, α-naphthyl and β-naphthyl.

As used herein, the term "heteroaryl", whether used alone or as part of another group, is defined as a substituted or unsubstituted aromatic heterocyclic ring system (monocyclic or bicyclic). Heteroaryl groups can have, for example, from about 3 to about 50 carbon atoms (unless explicitly specified otherwise) with from about 4 to about 10 being preferred. In some embodiments, heteroaryl groups are aromatic heterocyclic rings systems having about 4 to about 14 ring atoms and containing carbon atoms and 1, 2, 3, or 4 heteroatoms selected from oxygen, nitrogen or sulfur. Representative heteroaryl groups are furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Specifically included within the definition of "heteroaryl" are those aromatic heterocyclic rings that are optionally substituted with 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. In exemplary embodiments of the present invention, the rings of the heteroaryl group can be optionally substituted by 1 to 3 groups selected from halogen, $C_1$-$C_6$ alkyl, $C_1$-$C_6$ perfluoroalkyl, —O—$C_1$-$C_6$ perfluoroalkyl, $C_1$-$C_6$ alkoxy, —OH, —$NH_2$, —$NO_2$, —CN, aryl, —O-aryl, —NH-aryl, —NH—CO-alkyl, or —NH—CO-aryl.

The term "alkoxy" as used herein, refers to the group —$OR_a$ wherein $R_a$ is an alkyl group as defined above.

Exemplary substituents on the alkyl, alkenyl, alkynyl, thioalkoxy and alkoxy groups mentioned above include, but are not limited to, halogen, —O—$C_1$-$C_6$ alkyl, —NH—$C_1$-$C_6$ alkyl, —CN, —OH, and amino groups.

The term "arylalkyl", as used herein, whether used alone or as part of another group, refers to the group —$R_a$—$R_b$, where $R_a$ is an alkyl group as defined above, substituted by $R_b$, an aryl group, as defined above. Examples of arylalkyl moieties include, but are not limited to, benzyl, 1-phenylethyl, 2-phenylethyl, 3-phenylpropyl, 2-phenylpropyl and the like.

The term "alkylheteroaryl", as used herein, whether used alone or as part of another group, refers to the group -$R_c$-$R_a$, where $R_c$ is a heteroaryl group as defined above, substituted with $R_a$, an alkyl group as defined above.

The term "heterocycle", as used herein, whether used alone or as part of another group, refers to a stable 3 to 8-member ring containing carbons atoms and from 1 to 3 heteroatoms selected from the group consisting of nitrogen, phosphorus, oxygen, and sulfur. A heterocycle of this invention can be either a monocyclic or bicyclic ring system, and can be either saturated or partially saturated. Heterocycle groups include, but are not limited to, aziridinyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, and tetrahydroisoquinolinyl.

The term "perfluoroalkyl", as used herein, whether used alone or as part of another group, refers to a saturated aliphatic hydrocarbon having 1 to 6 carbon atoms and two or more fluorine atoms and includes, but is not limited to, straight or branched chains, such as —$CF_3$, —$CH_2CF_3$, —$CF_2CF_3$ and —$CH(CF_3)_2$.

The term "halogen" refers to chlorine, bromine, fluorine, and iodine.

In the present invention, both "p" and "n" can be 0, 1, 2, 3, 4, 5, or 6. "m" can be 1, 2, 3, 4, 5, or 6.

The term "treating" or "treatment" refers to any indicia of success in amelioration of an injury, pathology, or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluation. "Treating" or "treatment of a PAI-1 related disorder" includes preventing the onset of symptoms in a subject that may be predisposed to a PAI-1 related disorder but does not yet experience or exhibit symptoms of the disorder (prophylactic treatment), inhibiting the symptoms of the disorder (slowing or arresting its development), providing relief from the symptoms or side-effects of the disorder (including palliative treatment), and/or relieving the symptoms of the disorder (causing regression). Accordingly, the term "treating" includes the administration of the compounds or agents of the present invention to a subject to prevent or delay, to alleviate, or to arrest or inhibit development of the symptoms or conditions associated with PAI-1 related disorders, e.g., tumor growth associated with cancer. A skilled medical practitioner will know how to use standard methods to determine whether a patient is suffering from a disease associated with enhanced levels and/or activity of PAI-1, e.g., by examining the patient and determining whether the patient is suffering from a disease known to be associated with elevated PAI-1 levels or activity or by assaying for PAI-1 levels in blood plasma or tissue of the individual suspected of suffering from a PAI-1 related disease and comparing PAI-1 levels in the blood plasma or tissue of the individual suspected of suffering from a PAI-1 related disease to PAI-1 levels in the blood plasma or tissue of a healthy individual. Increased PAI-1 levels are indicative of disease. Accordingly, the present invention provides, inter alia, methods of administering a compound of the present invention to a subject and determining levels of PAI-1 in the subject. The level of PAI-1 in the subject can be determined before and/or after administration of the compound.

In healthy individuals, PAI-1 is found at low levels in the plasma (for example, about 5-26 ng/mL), but it is elevated in many PAI-1 related disorders, including, for example, atherosclerosis (Schneiderman J. et. al, *Proc Natl Acad Sci* 89: 6998-7002, 1992) deep vein thrombosis (Juhan-Vague I, et. al, *Thromb Haemost* 57: 67-72, 1987), and non-insulin dependent diabetes mellitus (Juhan-Vague I, et. al, *Thromb Haemost* 78: 565-660, 1997). PAI-1 stabilizes both arterial and venous thrombi, contributing respectively to coronary arterial occlusion in post-myocardial infarction (Hamsten A, et. al. *Lancet* 2:3-9, 1987), and venous thrombosis following post-operative recovery from orthopedic surgery. (Siemens H J, et. al, *J Clin Anesthesia* 11: 622-629, 1999). Plasma PAI-1 is also elevated, for example, in postmenopausal women, and has been proposed to contribute to the increased incidence of cardiovascular disease in this population (Koh K et. al, *N Engl J Med* 336: 683-690, 1997).

The term "PAI-1 related disorder or disease" refers to any disease or condition that is associated with increased or enhanced expression or activity of PAI-1 or increased or enhanced expression or activity of a gene encoding PAI-1. Examples of such increased activity or expression can include one or more of the following: activity of the protein or expression of the gene encoding the protein is increased above the level of that in normal subjects; activity of the protein or expression of the gene encoding the protein is in an organ, tissue or cell where it is not normally detected in normal subjects (i.e. spatial distribution of the protein or expression of the gene encoding the protein is altered); activity of the protein or expression of the gene encoding the protein is increased when activity of the protein or expression of the gene encoding the protein is present in an organ, tissue or cell for a longer period than in a normal subjects (i.e., duration of activity of the protein or expression of the gene encoding the protein is increased). A normal or healthy subject is a subject not suffering from a PAI-1 related disorder or disease. In some embodiments of the present invention, the PAI-1 related disorder is not associated with hyperglycemia. A PAI-1 related disorder that is not associated with hyperglycemia is one, for example, that is not caused by elevated levels of glucose in the blood.

The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" refers to salts and esters that are pharmaceutically acceptable and have the desired pharmacological properties. Such salts include, for example, salts that can be formed where acidic protons present in the compounds are capable of reacting with inorganic or organic bases. Suitable inorganic salts include, for example, those formed with the alkali metals or alkaline earth metals, e.g. sodium and potassium, magnesium, calcium, and aluminum. Suitable organic salts include, for example, those formed with organic bases such as the amine bases, e.g. ethanolamine, diethanolamine, triethanolamine, trimethamine, N methylglucamine, and the like. Pharmaceutically acceptable salts can also include acid addition salts formed from the reaction of basic moieties, such as amines, in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g. $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention can be present in more than one stereoisomeric form, and the naming of such compounds is intended to include all single stereoisomers and all mixtures (whether racemic or otherwise) of such stereoisomers.

"Inhibitors," "activators," and "modulators" of expression or of activity are used to refer to inhibitory, activating, or modulating molecules, respectively, identified using in vitro and in vivo assays for expression or activity. Inhibitors of the present invention are compositions that, inhibit expression of PAI-1 or bind to, partially or totally block stimulation, decrease, prevent, delay activation, inactivate, desensitize, or down regulate the activity of PAI-1. Samples or assays comprising PAI-1 can be treated with a composition of the present invention and compared to control samples without a composition of the present invention. Control samples (untreated with compositions of the present invention) can be assigned a relative activity value of 100%. In certain embodiments, inhibition of PAI-1 is achieved when the activity value relative to the control is about 80% or less, optionally 50% or 25, 10%, 5% or 1%.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the compound.

A "therapeutically effective amount" or "pharmaceutically effective amount" means the amount that, when administered to a subject, produces effects for which it is administered. For example, a "therapeutically effective amount," when administered to a subject to inhibit PAI-1 activity, is sufficient to inhibit PAI-1 activity. A "therapeutically effective amount," when administered to a subject for treating a disease, is sufficient to effect treatment for that disease.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that are associated with the targeted or suspected disease or condition. These and other routine methods allow the clinician to select patients in need of therapy using the methods and formulations of the present invention. In some embodiments of the present invention, the subject to be treated with the methods of the present invention does not have hyperglycemia and/or a disease that has been caused by hyperglycemia. Methods of determining whether a subject has hyperglycemia are known in the art and include, for example, performing a glucose test that measures the level of glucose in the blood. Two exemplary tests that can be used to measure the presence of excess levels of glucose in the blood include a test that measures the amount of glucose in the blood after an overnight fast and a test that measures the body's ability to process excess sugar presented after drinking a high glucose test. Typically a subject having a fasting sugar level (sugar level after an overnight fast) of about 64 to about 110 mg/dl does not have hyperglycemia whereas as person having a fasting sugar level of greater than 110 mg/dl has elevated blood sugar levels. A value above about 140 mg/dl on at least two occasions typically signifies that the subject has diabetes.

When any variable occurs more than one time in any constituent or in any formula, its definition in each occurrence is independent of its definition at every other occurrence. Combinations of substituents and/or variables are permissible only if such combinations result in stable compounds.

B. Substituted Aryl Oximes

The present invention provides substituted aryl oximes. Such compounds are preferably administered to inhibit PAI-1 expression or activity in a subject and, ultimately, to treat diseases or conditions including those associated with increased PAI-1 activity in a subject, e.g., a PAI-1 related disorder.

Substituted aryl oximes include those compounds of the following formula:

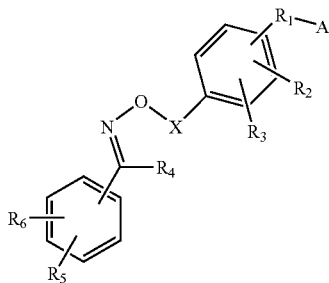

Formula 1 wherein:
$R_1$ is a direct bond to A, $C_1$-$C_4$ alkylene, or —O—$C_1$-$C_4$ alkylene;
$R_2$ and $R_3$ are, independently, hydrogen, halogen, $C_1$-$C_4$ alkyl, $C_1$-$C_3$ perfluoroalkyl, —O—$C_1$-$C_3$ perfluoroalkyl, $C_1$-$C_3$ alkoxy, —OH, —NH$_2$, —NO$_2$, aryl, heteroaryl, —O(CH$_2$)$_p$-aryl, —O(CH$_2$)$_p$-heteroaryl, —NH(CH$_2$)$_p$-aryl, —NH(CH$_2$)$_p$-heteroaryl, —NH(CO)-aryl, —NH(CO)-heteroaryl, —O(CO)-aryl, —O(CO)-heteroaryl, —NH(CO)—CH═CH-aryl, or —NH(CO)—CH═CH-heteroaryl;
p is an integer from 0-6;
$R_4$ is hydrogen, $C_1$-$C_8$ alkyl, or $C_3$-$C_6$ cycloalkyl;
A is COOH or an acid mimic;
X is $C_1$-$C_8$ alkylene, $C_3$-$C_6$ cycloalkylene, —(CH$_2$)$_m$O—, or —(CH$_2$)$_m$NH—;
m is an integer from 1-6; and
$R_5$ and $R_6$, are, independently, hydrogen, halogen, $C_1$-$C_6$ alkyl, $C_1$-$C_6$ perfluoroalkyl, —O—$C_1$-$C_6$ perfluoroalkyl, $C_1$-$C_6$ alkoxy, —OH, —NH$_2$, —NO$_2$, —O(CH$_2$)$_n$-aryl, —O(CH$_2$)$_n$-heteroaryl, aryl, or heteroaryl; and
n is an integer from 0-6.

Compounds of the present invention also include prodrugs, stereoisomers, or pharmaceutically acceptable salts or ester forms of formula 1.

Representative $R_1$ groups of formula 1 include, but are not limited to, $C_1$-$C_4$ alkylene, $C_1$-$C_3$ alkylene—O—$C_1$-$C_3$ alkylene, or —O—$C_1$-$C_4$ alkylene optionally substituted by 1 to 3 groups selected from, $C_1$-$C_4$ alkyl, aryl, or benzyl. In some embodiments, $R_1$ is a direct bond, —CH$_2$—, or —CH$_2$—CH$_2$—. In such embodiments, $R_2$, $R_3$, $R_4$, $R_5$, $R_6$, X, A, p, m, and n are as defined herein for formula 1. In certain preferred embodiments of formula 1, $R_1$ is a direct bond, unsubstituted $C_1$-$C_4$ alkylene, or unsubstituted —O—$C_1$-$C_4$ alkylene. In other preferred embodiments of formula 1, $R_1$ is a direct bond, unsubstituted $C_1$-$C_4$ alkylene, or —O—$C_1$-$C_4$ alkylene.

Representative $R_2$ groups of formula 1 include, but are not limited to, —O(CH$_2$)$_p$-aryl, —O(CH$_2$)$_p$-heteroaryl, aryl, heteroaryl, —NH(CH$_2$)$_p$-aryl, —NH(CH$_2$)$_p$-heteroaryl, —NH(CO)-aryl, —NH(CO)-heteroaryl groups, —O(CO)-aryl, —O(CO)-heteroaryl, —NH(CO)—CH═CH-aryl, or —NH(CO)—CH═CH-heteroaryl groups wherein the rings of the aryl or heteroaryl groups are optionally substituted by 1 to 3 groups selected from halogen, $C_1$-$C_4$ alkyl, $C_1$-$C_3$ perfluoroalkyl, —O—$C_1$-$C_3$ perfluoroalkyl, $C_1$-$C_3$ alkoxy, —OH, —NH$_2$, —CN or —NO$_2$. In certain embodiments, $R_2$ is hydrogen, —OH, halogen, O(CO)-aryl wherein the aryl group is unsubstituted or substituted with CF$_3$, phenyl, —OCH$_2$ or t-butyl, —O(CH$_2$)-aryl wherein the aryl group is unsubstituted or substituted with CF$_3$, or —NH(CO)-aryl wherein the aryl group is unsubstituted or substituted with t-butyl, CF$_3$ or —OCF$_3$. In such embodiments, $R_1$, $R_3$, $R_4$, $R_5$, $R_6$, X, A, p, m, and n are as defined herein for formula 1.

Representative $R_3$ groups of formula 1 include, but are not limited to, —O(CH$_2$)$_p$-aryl, —O(CH$_2$)$_p$-heteroaryl, aryl, heteroaryl, —NH(CH$_2$)$_p$-aryl, —NH(CH$_2$)$_p$-heteroaryl, —NH(CO)-aryl, —NH(CO)-heteroaryl groups, —O(CO)-aryl, —O(CO)-heteroaryl, —NH(CO)—CH═CH-aryl, or —NH(CO)—CH═CH-heteroaryl groups wherein the rings of the aryl and heteroaryl groups are optionally substituted by 1 to 3 groups selected from halogen, $C_1$-$C_4$ alkyl, $C_1$-$C_3$ perfluoroalkyl, —O—$C_1$-$C_3$ perfluoroalkyl, $C_1$-$C_3$ alkoxy, —OH, —NH$_2$, —CN, or —NO$_2$. In certain embodiments, $R_3$ is hydrogen, —OH, halogen, O(CO)-aryl wherein the aryl group is unsubstituted or substituted with CF$_3$, phenyl, —OCH$_2$ or t-butyl, —O(CH$_2$)-aryl wherein the aryl group is unsubstituted or substituted with CF$_3$, or —NH(CO)-aryl wherein the aryl group is unsubstituted or substituted with t-butyl, CF$_3$ or —OCF$_3$. In such embodiments, $R_1$, $R_2$, $R_4$, $R_5$, $R_6$, X, A, p, m, and n are as defined herein for formula 1.

Representative $R_4$ groups of formula 1 include, but are not limited to, $C_1$-$C_6$ alkyl, hydrogen, aryl, and $C_3$-$C_6$ cycloalkyl. In certain embodiments, $R_4$ is hydrogen or alkyl. In such embodiments, $R_1$, $R_2$, $R_3$, $R_5$, $R_6$, X, A, p, m, and n are as defined herein for formula 1.

Representative $R_5$ groups of formula 6 include, but are not limited to, —O(CH$_2$)$_n$-aryl, —O(CH$_2$)$_n$-heteroaryl, aryl, or heteroaryl wherein the rings of the aryl and/or heteroaryl groups are substituted by 1 to 3 groups selected from halogen, $C_1$-$C_6$ alkyl, $C_1$-$C_6$ perfluoroalkyl, —O—$C_1$-$C_6$ perfluoroalkyl, $C_1$-$C_6$ alkoxy, —OH, —NH$_2$, —CN or —NO$_2$. In certain embodiments, $R_5$ is hydrogen, aryl, t-butyl, or CF$_3$. In such embodiments, $R_1$, $R_2$, $R_3$, $R_4$, $R_6$, X, A, p, m, and n are as defined herein for formula 1.

Representative $R_6$ groups of formula 1 include, but are not limited to, —O(CH$_2$)$_n$-aryl, —O(CH$_2$)$_n$-heteroaryl, aryl, or heteroaryl groups that are optionally substituted by 1 to 3 groups selected from halogen, $C_1$-$C_6$ alkyl, $C_1$-$C_6$ perfluoroalkyl, —O—$C_1$-$C_6$ perfluoroalkyl, $C_1$-$C_6$ alkoxy, —OH, —NH$_2$, —CN, or —NO$_2$. In certain embodiments, $R_6$ is hydrogen, aryl, t-butyl, or CF$_3$. In such embodiments, $R_1$, $R_2$, $R_3$, $R_4$, $R_5$, X, A, p, m, and n are as defined herein for formula 1.

Representative X groups of formula 1 include, but are not limited to, $C_1$-$C_6$ alkyl, $C_1$-$C_6$ branched alkyl, —(CH$_2$)$_m$O where m is an integer from 2-5.

Representative A groups of formula 1 include, but are not limited to, —COOH and tetrazole.

In certain embodiments, such substituted aryl oximes include the following compounds:

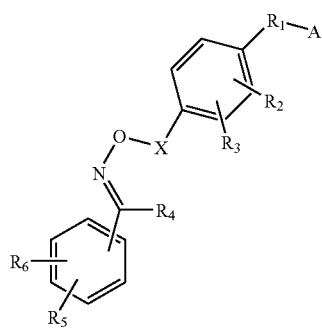

Formula 2

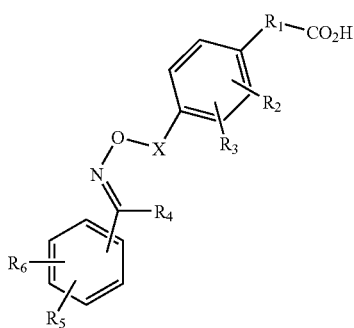

Formula 3 wherein $R_1$, $R_2$, $R_3$, $R_4$, $R_5$, $R_6$, X, A, p, m, and n are defined as above for Formula 1.

Exemplary substituted aryl oximes of the present invention include, but are not limited to, (4-{3-[1-(4-tert-butyl-phenyl)-ethylideneaminooxy]-propoxy}-phenyl)-acetic acid or a pharmaceutically acceptable salt or ester form thereof; {4-[1-(4-tert-butyl-phenyl)-ethylideneaminooxymethyl]-phenyl}-acetic acid or a pharmaceutically acceptable salt or ester form thereof; [4-(4-tert-butyl-benzylideneaminooxymethyl)-phenyl]-acetic acid or a pharmaceutically acceptable salt or ester form thereof; {4-[3-(4-tert-butyl-benzylideneaminooxy)-propoxy]-phenyl}-acetic acid or a pharmaceutically acceptable salt or ester form thereof; 4-{2-[({(E)-1-[4-(tert-butyl)-phenyl]-ethylidene}amino)oxy]-ethoxy}-2-hydroxy-benzoic acid or a pharmaceutically acceptable salt or ester form thereof; 2-{[4-(tert-Butyl)benzoyl]oxy)}4-[2-({1-phenylethylidene]amino}oxy)ethoxy]benzoic acid or a pharmaceutically acceptable salt or ester form thereof; 4-{2-[({[4-(tert-butyl)phenyl]methylidene}amino)oxy]-ethoxy}-2-hydroxybenzoic acid or a pharmaceutically acceptable salt or ester form thereof; 4-[2-[({(E)-[4-(tert-butyl)phenyl]methylidene}amino)oxy]ethoxy}-2-{[4-(trifluoromethyl)benzoyl]oxy}benzoic acid or a pharmaceutically acceptable salt or ester form thereof; 4-{2-[({(E)-[4-(tert-butyl)phenyl]methylidene}amino)oxy]ethoxy}-2-[(4-methoxybenzoyl)oxy]benzoic acid or a pharmaceutically acceptable salt or ester form thereof; 2-{[4-(tert-butyl)benzoyl]oxy}-4-{2-[({(E)-[4-(tert-butyl)phenyl]methylidene}amino)oxy]ethoxy}benzoic acid or a pharmaceutically acceptable salt or ester form thereof; 2-(benzoyloxy)-4-{2-[({(E)-[4-(tert-butyl)phenyl]methylidene}amino)oxy]ethoxy}benzoic acid or a pharmaceutically acceptable salt or ester form thereof; 4-{2-[({(E)-1-[4-(tert-butyl)phenyl]ethylidene}amino)oxy]-ethoxy}-3-chloro-benzoic acid or a pharmaceutically acceptable salt or ester form thereof; 4-[2-[({(E)-1-[4-(tert-butyl)phenyl]ethylidene}amino)oxy]-ethoxy}-2-chloro-benzoic acid or a pharmaceutically acceptable salt or ester form thereof; 4-{2-[({[4-(tert-butyl)phenyl]methylidene}amino)oxy]ethoxy}-2-{[4-(trifluoromethyl)benzyl]oxy}benzoic acid or a pharmaceutically acceptable salt or ester form thereof; 2-[([1,1'-biphenyl]-4-ylcarbonyl)oxy]-4-[2-({[(E)-1-phenylethylidene]amino}oxy)ethoxy]benzoic acid or a pharmaceutically acceptable salt or ester form thereof; 3-(4-{3-[({(E)-[4-(tert-butyl)phenyl]methylidene}amino)oxy]propoxy}phenyl)propanoic acid or a pharmaceutically acceptable salt or ester form thereof; 4-(tert-butyl)benzaldehyde 0-{3-[4-(1H-tetraazol-5-ylmethyl)-phenoxy]-propyl}oxime or a pharmaceutically acceptable salt or ester form thereof; 2-{[4-(tert-butyl)benzoyl]amino}-4-{3-[({(E)-[4-(tert-butyl)phenyl]methylidene}amino)oxy]propoxy}benzoic acid or a pharmaceutically acceptable salt or ester form thereof; 4-{3-[({(E)-[3,5-bis(trifluoromethyl)phenyl]methylidene}amino)oxy]propoxy}-2-hydroxybenzoic acid or a pharmaceutically acceptable salt or ester form thereof; 4-[3-({[(1E)-1,1'-Biphenyl-4-ylmethylidene]amino}oxy)propoxy]-2-{[4-(trifluoromethyl)benzoyl]amino}benzoic acid or a pharmaceutically acceptable salt or ester form thereof; 4-[3-({[(1E)-1-(4-tert-butylphenyl)propylidene]amino}oxy) propoxy]-2-{[4-(trifluoromethyl)benzoyl]amino}benzoic acid or a pharmaceutically acceptable salt or ester form thereof; 2-{[4-(trifluoromethyl)benzoyl]amino}-4-{3-[({(1E)-[4-(trifluoromethyl)phenyl]methylidene}amino)oxy]propoxy}benzoic acid or a pharmaceutically acceptable salt or ester form thereof; 4-[3-({[[1E]-1-phenylethylidene]amino}oxy)propoxy]-2-{[4-(trifluoromethyl)benzoyl]amino}benzoic acid or a pharmaceutically acceptable salt or ester form thereof; 4-[3-({[(1E)-(4-tert-butylphenyl)methylidene]amino}oxy)propoxy]-2-{[2-trifluoromethyl)benzoyl]amino}benzoic acid or a pharmaceutically acceptable salt or ester form thereof; 2-{[2-(trifluoromethyl)benzoyl]amino}-4-{3-[({(1E)-[4-trifluromethyl)phenyl]methylidene}amino)oxy]propoxy}benzoic acid or a pharmaceutically acceptable salt or ester form thereof; 4-[3-({[(1E)-1,1'-biphenyl-4-ylmethylidene]amino}oxy)propoxy]-2-{[2-(trifluoromethyl)benzoyl]amino}benzoic acid or a pharmaceutically acceptable salt or ester form thereof; 2-{[3,5-bis(trifluoromethyl)benzoyl]amino}-4-[3-({[(1E)-(4-tert-butylphenyl)methylidene]amino}oxy)propoxy]benzoic acid or a pharmaceutically acceptable salt or ester form thereof; 4-{3-[({(1E)-[3,5-bis(trifluoromethyl)phenyl]methylidene}amino)oxy]propoxy}-2-{[4-(trifluoromethoxy)benzoyl]amino}benzoic acid or a pharmaceutically acceptable salt or ester form thereof; 4-[3-({[(1E)-1,1'-biphenyl-4-ylmethylidene]amino}oxy)propoxy]-2-{[4-(trifluoromethoxy)benzoyl]amino}benzoic acid or a pharmaceutically acceptable salt or ester form thereof; 2-{[4-(trifluoromethoxy)benzoyl] amino}-4-{3-[({(1E)-[4-(trifluoromethyl)phenyl] methylidene}amino)oxy]propoxy}benzoic acid or a pharmaceutically acceptable salt or ester form thereof; 4-[3-({[(1E)-1,1'-biphenyl-4-ylmethylidene]amino}oxy)propoxy]-2-{[3, 5-bis(trifluoromethyl)benzoyl]amino}benzoic acid or a pharmaceutically acceptable salt or ester form thereof; 2-{[3, 5-bis(trifluoromethyl)benzoyl]amino}-4-{3-[({(1 E)-[4-(trifluoromethyl)phenyl]methylidene}amino)oxy] propoxy}benzoic acid or a pharmaceutically acceptable salt or ester form thereof; 2-bromo-4-[({[(1E)-(4-tert-butylphenyl)methylidene]amino}oxy)methyl]benzoic acid or a pharmaceutically acceptable salt or ester form thereof; 4-[3-({[(1E)-(4-tert-butylphenyl)methylidene]amino}oxy)propoxy]-2-(2-naphthoylamino)benzoic acid or a pharmaceutically acceptable salt or ester form thereof; 2-{[(2E)-3-(1,1'-biphenyl-4-yl)prop-2-enoyl]amino}4-[3-({[(1E)-(4-tert-butylphenyl)methylidene]amino}oxy)propoxy]-benzoic acid or a pharmaceutically acceptable salt or ester form thereof; and 2-[(1,1'-biphenyl-4-ylcarbonyl)amino]-4-[3-({[(1E)-(4-tert-butylphenyl)methylidene]amino}oxy)propoxy]benzoic acid or a pharmaceutically acceptable salt or ester form thereof.

The present invention also provides compositions comprising substituted aryl oximes, including those compounds of formulas 1-3 or a stereoisomer or pharmaceutically acceptable salt thereof, and one or more pharmaceutically acceptable carriers, excipients, or diluents. Such compositions include pharmaceutical compositions for treating or controlling disease states or conditions associated with increased PAI-1 activity. In certain embodiments, the compositions comprise mixtures of one or more substituted aryl oximes.

Certain of the compounds of formulas 1-3 contain stereogenic carbon atoms or other chiral elements and thus give rise to stereoisomers, including enantiomers and diastereomers. The present invention includes all of the stereoisomers of formulas 1-3, as well as mixtures of the stereoisomers. Throughout this application, the name of the product, where the absolute configuration of an asymmetric center is not indicated, is intended to embrace the individual stereoisomers as well as mixtures of stereoisomers.

Where an enantiomer is preferred, it can, in some embodiments, be provided substantially free of the corresponding enantiomer. Thus, an enantiomer substantially free of the corresponding enantiomer refers to a compound that is isolated or separated via separation techniques or prepared free of the corresponding enantiomer. "Substantially free," as used herein, means that the compound is made up of a significantly greater proportion of one enantiomer. In preferred embodiments, the compound is made up of at least about 90% by weight of a preferred enantiomer. In other embodiments of the invention, the compound is made up of at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein. Methods for the preparation of preferred enantiomers are described, for example, in Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972).

Exemplary salt forms of the compounds herein include, but are not limited to, sodium salts and potassium salts. Other exemplary salt forms of these compounds include, but are not limited to, those formed with pharmaceutically acceptable inorganic and organic bases known in the art. Salt forms prepared using inorganic bases include hydroxides, carbonates or bicarbonates of the therapeutically acceptable alkali metals or alkaline earth metals, such as sodium potassium, magnesium, calcium and the like. Acceptable organic bases include amines, such as benzylamine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Exemplary salts also include alkylene diamines containing up to 6 carbon atoms, such as hexamethylenediamine; cyclic saturated or unsaturated bases containing up to 6 carbon atoms, including pyrrolidine, piperidine, morpholine, piperazine and their N-alkyl and N-hydroxyalkyl derivatives, such as N-methyl-morpholine and N-(2-hyroxyethyl)-piperidine, or pyridine. Quaternary salts can also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-di-methylmorpholinium, N-methyl-N-(2-hydroxyethyl)-morpholinium, or N,N-dimethyl-piperidinium salt forms. These salt forms can be prepared using the acidic compound(s) of Formulas 1-3 and procedures known in the art.

Exemplary ester forms of the compounds of this invention include, but are not limited to, straight chain alkyl esters having from 1 to 6 carbon atoms or branched chain alkyl groups containing 3 or 6 carbon atoms, including methyl, ethyl, propyl, butyl, 2-methylpropyl and 1, 1-dimethylethyl esters, cycloalkyl esters, alkylaryl esters, benzyl esters, and the like. Other exemplary esters include, but are not limited to, those of the formula —COOR$_7$ wherein R$_7$ is selected from the formula:

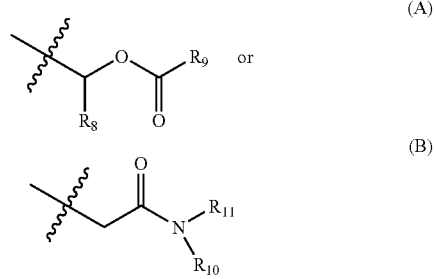

wherein R$_8$, R$_9$, R$_{10}$, R$_{11}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Acids and acid mimics, according to the invention, are defined as proton or hydrogen donating groups. Exemplary acid mimics or mimetics of the present invention include pharmaceutically useful carboxylic acids and acid mimics or mimetics known in the art, such as those described in R. Silverman, The Organic Chemistry of Drug Design and Drug Action, Academic Press (1992) and others. Exemplary acid mimics or mimetics include tetrazole, tetronic acid, acyl tetronic acid, and groups having the formula:

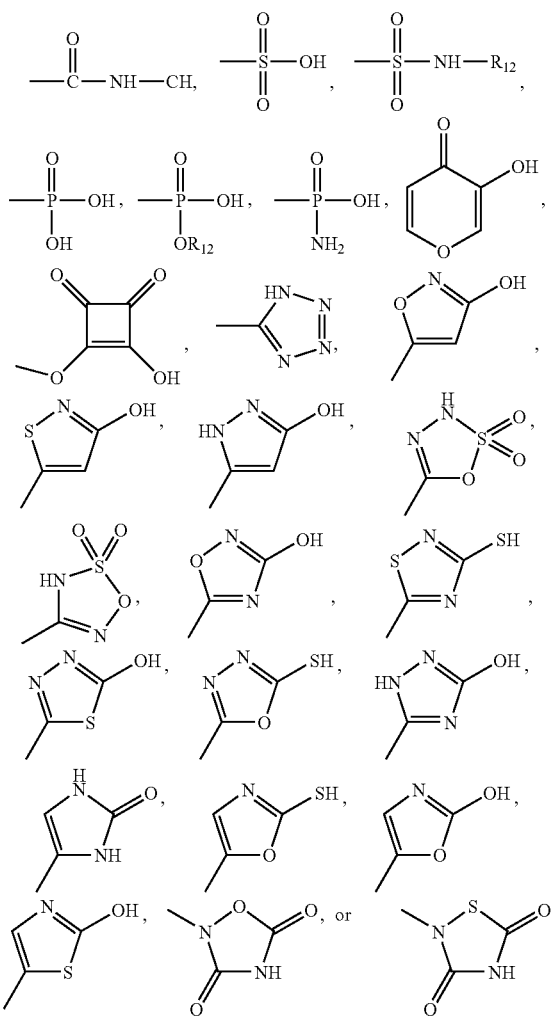

wherein $R_{12}$ is $C_1$-$C_6$ alkyl, $C_2$-$C_6$ alkenyl, $C_3$-$C_6$ cycloalkyl, —$CH_2$—($C_3$-$C_6$ cycloalkyl), $C_3$-$C_6$ cycloalkenyl, —$CH_2$—($C_3$-$C_6$ cycloalkenyl), optionally substituted aryl or heteroaryl groups or optionally substituted aryl($C_1$-$C_6$)alkyl or heteroaryl($C_1$-$C_6$)alkyl, with the aryl and heteroaryl groups as defined herein.

Preferred compounds of the present invention inhibit PAI-1 activity. Accordingly, the compounds can be used for the treatment, including prevention, inhibition, and/or amelioration of PAI-1 related disorders in a subject, including, for example, in the treatment of noninsulin dependent diabetes mellitus, in the treatment of cardiovascular disease, and in the treatment of thrombotic events associated with coronary artery and cerebrovascular disease. Using the methods of the present invention, a skilled medical practitioner will know how to administer substituted aryl oximes, including those represented by formulas 1-3, to a subject suffering from any of the diseases associated with increased PAI-1 activity or expression, e.g., diabetes or cardiovascular disease, in order to effect treatment for that disease.

In one exemplary embodiment, substituted aryl oximes are administered to a subject in order to treat disease processes involving thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary thrombosis, cerebral thrombosis, thromboembolic complications of surgery (such as joint or hip replacement), and peripheral arterial occlusion.

Any disease or condition that is associated with increased PAI-1 activity or expression in a subject can be treated using substituted aryl oximes. Exemplary diseases and conditions include stroke, e.g., stroke associated with or resulting from atrial fibrillation; diseases associated with extracellular matrix accumulation including, but not limited to, renal fibrosis, chronic obstructive pulmonary disease, polycystic ovary syndrome, restenosis, renovascular disease, and organ transplant rejection; diseases associated with neoangiogenesis, including, but not limited to, diabetic retinopathy; Alzheimer's disease, e.g., by increasing or normalizing levels of plasmin concentration in a subject; myelofibrosis with myeloid metaplasia, e.g., by regulating stromal cell hyperplasia and increases in extracellular matrix proteins.

The compounds of the present invention can be used to treat, for example, diabetic nephropathy and renal dialysis associated with nephropathy; malignancies or cancers, including, but not limited to, leukemia, breast cancer and ovarian cancer; tumors, including, but not limited to, liposarcomas and epithelial tumors; septicemia; obesity; insulin resistance; proliferative diseases, including, but not limited to, psoriasis; conditions associated with abnormal coagulation homeostasis; low grade vascular inflammation; cerebrovascular diseases; hypertension; dementia; osteoporosis; arthritis; respiratory diseases, such as asthma; heart failure; arrhythmia; angina, including, but not limited to, angina pectoris; atherosclerosis and sequelae; kidney failure; multiple sclerosis; osteoporosis; osteopenia; dementia; peripheral vascular disease; peripheral arterial disease; acute vascular syndromes; microvascular diseases including, but not limited to, nephropathy, neuropathy, retinopathy and nephrotic syndrome; hypertension; Type I and II diabetes and related diseases; hyperglycemia; hyperinsulinemia; malignant lesions; premalignant lesions; gastrointestinal malignancies; coronary heart disease, including, but not limited to, primary and secondary prevention of myocardial infarction, stable and unstable angina, primary prevention of coronary events, and secondary prevention of cardiovascular events; and inflammatory diseases, including, but not limited to, septic shock and the vascular damage associated with infections.

The compounds of the present invention can also be administered to a subject in combination with a second therapeutic agent, including, but not limited to, prothrombolytic, fibrinolytic, and anticoagulant agents, or in conjunction with other therapies, for example, protease inhibitor-containing highly active antiretroviral therapy (HAART) for the treatment of diseases which originate from fibrinolytic impairment and hyper-coagulability of HIV-1 infected patients. In certain embodiments, the compounds of the present invention can be administered in conjunction with and/or following processes or procedures involving maintaining blood vessel patency, including, but not limited to, vascular surgery, vascular graft and stent patency, organ, tissue and cell implantation and transplantation. The compounds of the present invention can also be used for the treatment of blood and blood products used in dialysis, blood storage in the fluid phase, especially ex vivo platelet aggregation. The compounds of the present invention can also be administered to a subject as a hormone replacement agent or to reduce inflammatory markers or C-reactive protein. The compounds can be administered to improve coagulation homeostasis, to improve endothelial function, or as a topical application for wound healing, e.g., the prevention of scarring. The compounds of the present invention can be administered to a subject in order to reduce the risk of undergoing a myocardial revascularization procedure. The present compounds can also be added to human plasma during the analysis of blood chemistry in hospital settings to determine the fibrinolytic capacity thereof. In certain embodiments, the compounds of the present invention can be used as imaging agents for the identification of metastatic cancers.

C. Synthesis of Substituted Aryl Oximes

Compounds of the present invention can be prepared by those skilled in the art of organic synthesis employing conventional methods that utilize readily available reagents and starting materials. Representative compounds of the present invention can be prepared using the following synthetic schemes. In the following synthetic schemes, $R_1$, $R_2$, $R_3$, $R_4$, $R_5$, $R_6$, X, and A are selected from the groups defined above. The skilled practitioner will know how to make use of variants of these process steps, which in themselves are well known in the art.

Representative substituted aryl oximes of the present invention can be prepared using scheme 1.

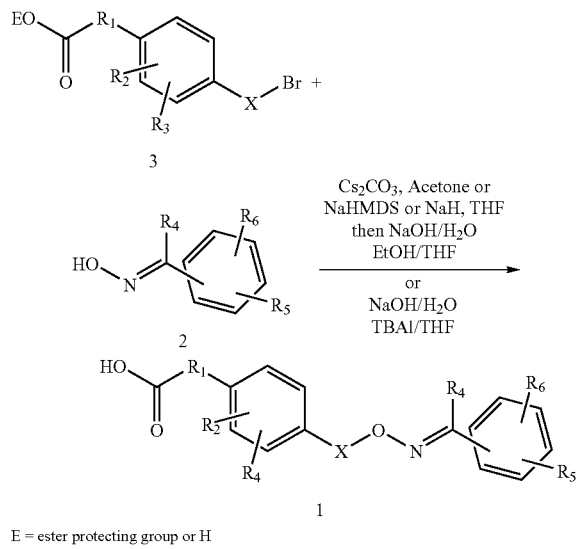

E = ester protecting group or H

In Scheme 1, compounds can be prepared by coupling of the oxime 2 with bromide 3 either in presence of a base like cesium carbonate in a solvent like acetone or like sodium hexamethyldisilylazide or sodium hydride in a solvent like THF, followed by saponification or by treatment under basic conditions to give acid derivatives.

D. Substituted Aryl Oximes as Pharmaceutical Compositions

The present invention provides substituted aryl oximes as pharmaceuticals. In a preferred embodiment, the aryl oximes are formulated as pharmaceuticals to treat diseases associated with increased PAI-1 activity, e.g., by inhibiting PAI-1 activity in a subject.

In general, substituted aryl oximes can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection). Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso A R: Remington's Pharmaceutical Sciences, 17th ed., Mack Publishing Company, Easton Pa., 1985. Suitable liquid carriers, especially for injectable solutions, include water, aqueous saline solution, aqueous dextrose solution, and glycols. In some embodiments of the present invention, substituted aryl oximes suitable for use in the practice of this invention will be administered either singly or in combination with at least one other compound of this invention. Substituted aryl oximes suitable for use in the practice of the present invention can also be administered with at least one other conventional therapeutic agent for the disease being treated.

Aqueous suspensions of the invention can contain a substituted aryl oxime in admixture with excipients suitable for the manufacture of aqueous suspensions. Such excipients can include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions can be formulated by suspending a substituted aryl oxime in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of substituted aryl oxime in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol. The formulations of commends can be presented in unit-dose or multi-dose sealed containers, such as ampules and vials.

Injection solutions and suspensions can be prepared from sterile powders, granules, and tablets of the kind previously described.

Substituted aryl oximes suitable for use in the practice of this invention can be administered orally. The amount of a compound of the present invention in the composition can vary widely depending on the type of composition, size of a unit dosage, kind of excipients, and other factors well known to those of ordinary skill in the art. In general, the final composition can comprise, for example, from 0.000001 percent by weight (% w) to 10% w of the substituted aryl oxime, preferably 0.00001% w to 1% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropylmethyl-cellulose or sodium carboxymethylcellulose; and gums including arabic and tragacanth; as well as proteins such as gelatin and collagen. If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The substituted aryl oximes of the present invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

The substituted aryl oximes of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" is intended to include the active ingredient in combination with an encapsulating material as a formulation, with or without other carriers. For example, the compounds of the present invention can also be delivered as microspheres for slow release in the body. In one embodiment, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present invention, e.g., anti-atherosclerotic medicaments.

In another embodiment, the compounds of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compound into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

In other cases, the preferred preparation can be a lyophilized powder which may contain, for example, any or all of the following: 1 mM-50 mM histidine, 0.1%-2% sucrose, 2%-7% mannitol, at a pH range of 4.5 to 5.5, that is combined with buffer prior to use.

A pharmaceutical composition of the invention can optionally contain, in addition to a substituted aryl oxime, at least one other therapeutic agent useful in the treatment of a disease or condition associated with increased PAI-1 activity.

The pharmaceutical compositions are generally formulated as sterile, substantially isotonic and in full compliance with all Good Manufacturing Practice (GMP) regulations of the U.S. Food and Drug Administration.

E. Determining Dosage Regimens for Substituted Aryl Oximes

The present invention provides methods of inhibiting PAI-1 activity in a subject for the treatment of diseases and conditions associated with increased PAI-1 activity using substituted aryl oximes. In an exemplary embodiment of the present invention, a skilled practitioner will treat a subject having a disease associated with elevated PAI-1 levels and/or activity with a compound of the present invention.

For treatment purposes, the compositions or compounds disclosed herein can be administered to the subject in a single bolus delivery, via continuous delivery (e.g., continuous transdermal, mucosal, or intravenous delivery) over an extended time period, or in a repeated administration protocol (e.g., by an hourly, daily or weekly, repeated administration protocol). The pharmaceutical formulations of the present invention can be administered, for example, one or more times daily, 3 times per week, or weekly. In an exemplary embodiment of the present invention, the pharmaceutical formulations of the present invention are orally administered once or twice daily.

In this context, a therapeutically effective dosage of the biologically active agent(s) can include repeated doses within a prolonged treatment regimen that will yield clinically significant results to alleviate one or more symptoms or detectable conditions associated with increased PAI-1 activity. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response). In alternative embodiments, an "effective amount" or "effective dose" of the biologically active agent(s) can simply inhibit or enhance one or more selected biological activity(ies) correlated with a disease or condition, as set forth above, for either therapeutic or diagnostic purposes.

The actual dosage of biologically active agents will of course vary according to factors such as the extent of exposure and particular status of the subject (e.g., the subject's age, size, fitness, extent of symptoms, susceptibility factors, etc), time and route of administration, as well as other drugs or treatments being administered concurrently. Dosage regimens can be adjusted to provide an optimum prophylactic or therapeutic response. By "therapeutically effective dose" herein is meant a dose that produces effects for which it is administered. More specifically, a therapeutically effective dose of the compound(s) of the invention preferably alleviates symptoms, complications, or biochemical indicia of diseases associated with increased PAI-1 activity. The exact dose will depend on the purpose of the treatment, and will be ascertainable by one skilled in the art using known techniques (see, e.g., Lieberman, Pharmaceutical Dosage Forms (Vols. 1-3, 1992); Lloyd, 1999, *The Art, Science, and Technology of Pharmaceutical Compounding*; and Pickar, 1999, *Dosage Calculations*). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

In an exemplary embodiment of the present invention, unit dosage forms of the compounds are prepared for standard administration regimens. In this way, the composition can be subdivided readily into smaller doses at the physicians direction. For example, unit dosages can be made up in packeted powders, vials or ampoules and preferably in capsule or tablet form. The active compound present in these unit dosage forms of the composition can be present in an amount of, for example, from about one gram to about fifteen grams or more, for single or multiple daily administration, according to the particular need of the patient. By initiating the treatment regimen with a minimal daily dose of about one gram, the blood levels of PAI-1 and the patients symptomatic relief analysis can be used to determine whether a larger or smaller dose is indicated. Effective administration of the compounds of this invention can be given at an oral dose of from about 0.1 mg/kg/day to about 1,000 mg/kg/day. Preferably, administration will be from about 10/mg/kg/day to about 600 mg/kg/day, more preferably from about 25 to about 200 mg/kg/day, and even more preferably from about 50 mg/kg/day to about 100 mg/kg/day. In some embodiments, a daily dosage of from about 1 mg/kg to about 250 mg/kg is provided.

In certain embodiments, the present invention is directed to prodrugs of compounds of formulas 1-3. The term "prodrug," as used herein, means a compound that is convertible in vivo by metabolic means (e.g. by hydrolysis) to a compound of formula 1-3. Various forms of prodrugs are known in the art such as those discussed in, for example, Bundgaard, (ed.), *Design of Prodrugs*, Elsevier (1985); Widder, et al. (ed.),

*Methods in Enzymology*, vol. 4, Academic Press (1985); Krogsgaard-Larsen, et al., (ed). "Design and Application of Prodrugs, *Textbook of Drug Design and Development*, Chapter 5, 113-191 (1991), Bundgaard, et al., *Journal of Drug Delivery Reviews*, 8:1-38(1992), Bundgaard, *J. of Pharmaceutical Sciences*, 77:285 et seq. (1988); and Higuchi and Stella (eds.) *Prodrugs as Novel Drug Delivery Systems*, American Chemical Society (1975).

F. Kits

After a pharmaceutical comprising a substituted aryl oxime has been formulated in a suitable carrier, it can be placed in an appropriate container and labeled for treatment of a PAI-1 related disorder, e.g., leukemia. Additionally, another pharmaceutical comprising at least one other therapeutic agent useful in the treatment of the PAI-1 related disorder can be placed in the container as well and labeled for treatment of the indicated disease. Alternatively, a single pharmaceutical comprising a substituted aryl oxime and at least one other therapeutic agent useful in the treatment of a PAI-1 related disorder can be placed in an appropriate container and labeled for treatment. For administration of pharmaceuticals comprising substituted aryl oximes and of pharmaceuticals comprising, in a single pharmaceutical, substituted aryl oximes and at least one other therapeutic agent useful in the treatment of a PAI-related disorder, such labeling would include, for example, instructions concerning the amount, frequency and method of administration. Similarly, for administration of multiple pharmaceuticals provided in the container, such labeling would include, for example, instructions concerning the amount, frequency and method of administration of each pharmaceutical.

EXAMPLES

Example 1

Synthesis of (4-{3-[1-(4-tert-Butyl-phenyl)-ethylideneaminooxy]-propoxy}-phenyl)-acetic Acid Step 1: To a solution of methyl 4-hydroxy phenyl acetic acid (8.240 g, 49.6 mmol) in acetonitrile (100 mL) was added potassium carbonate (20.75 g, 150.2 mmol) and dibromopropane (25 mL, 246.2 mmol). The reaction mixture was heated at reflux for 5 hours, cooled to room temperature and then concentrated to a small volume in vacuo. The residue was partitioned between ethyl acetate and brine and the aqueous layer was extracted with ethyl acetate. The combined organics were washed with brine, dried over anhydrous magnesium sulfate and concentrated in vacuo. The residue was purified by flash chromatography using ethyl acetate/hexanes (20/80) to afford [4-(3-bromo-propoxy)-phenyl]-acetic acid methyl ester (11.23 g, 79%) as a colorless oil. $^1$H NMR (300 MHz, $CD_3Cl_3$); δ 7.21 (d, 2H), 6.86 (d, 2H), 4.09 (t, 2H), 3.70 (s, 3H), 3.61 (t, 2H); 3.58 (s, 2H), 2.31 (m, 2H).

Step 2: To a solution of 1-(4-tert-butyl-phenyl)-ethanone oxime (0.679 g, 3.55 mmol) in tetrahydrofuran (25 mL) was added sodium hexamethyldisilazane (3.6 mL, 3.6 mmol) and the resulting solution was stirred at room temperature for 30 minutes. [4-(3-bromo-propoxy)-phenyl]-acetic acid methyl ester was then added as a solution in tetrahydrofuran (10 mL) and the reaction was stirred at room temperature for 48 hours. No reaction was observed and the reaction was heated at reflux for 48 hours. It was then poured into brine, extracted with ethyl acetate, dried over magnesium sulfate and concentrated in vacuo. The (4-{3-[1-(4-tert-butyl-phenyl)-ethylideneaminooxy]-propoxy}-phenyl)-acetic acid methyl ester was used crude in the subsequent reaction. $^1$H NMR (300 MHz, $CD_3Cl_3$); δ 7.62 (d, 2H), 7.42 (d, 2H), 7.22 (d, 2H), 6.92 (d, 2H), 4.41 (t, 2H), 4.11 (t, 2H), 3.70 (s, 3H), 3.60 (s, 2H), 2.26 (s, 3H), 2.24 (m, 2H), 1.70 (s, 9H).

Step 3: To a solution of (4-{3-[1-(4-tert-butyl-phenyl)-ethylideneaminooxy]-propoxy}-phenyl)-acetic acid methyl ester (3.55 mmol) in tetrahydrofuran/ethanol (3/2) (20 mL) was added 1 M sodium hydroxide solution (6 mL, 6 mmol) and the reaction was stirred overnight at room temperature. It was concentrated to a small volume, acidified to pH 1 with 1M hydrochloric acid solution and extracted with ethyl acetate. The combined organics were washed with brine, dried over anhydrous magnesium sulfate and concentrated in vacuo. The residue was purified by flash chromatography using ethyl acetate/hexanes (20/80)+1% formic acid to afford the title compound (0.620 g, 46%) as a light yellow solid. mp=98.7-99.7° C.; mass spectrum (−ESI, M−H) m/z 382. $^1$H NMR (400 MHz, DMSO-$d_6$); δ 12.20 (bs, 1H), 7.55 (d, 2H), 7.38 (d, 2H). 7.14 (d, 2H), 6.87 (d, 2H), 4.25 (t, 2H), 4.05 (t, 2H), 3.47 (s, 2H), 2.16 (s, 3H), 2.09 (m, 2H), 1.25 (s, 9H). Elemental analysis: Calcd. for $C_{23}H_{29}NO_4$: C, 72.04; H, 7.62; N, 3.65, Found: C, 71.43; H, 7.87; N, 3.52.

Example 2

Synthesis of {4-[1-(4-tert-Butyl-phenyl)-ethylideneaminooxymethyl]-phenyl}-acetic Acid To a slurry of sodium hydride (95%) (0.531 g, 22.1 mmol) in tetrahydrofuran (4 mL) was added 1-(4-tert-butyl-phenyl)-ethanone oxime (0.791 g, 4.13 mmol) as a solution in tetrahydrofuran (10 mL) and the solution was allowed to stir at room temperature for 1 hour. (4-Bromomethyl-phenyl)-acetic acid (9.10 g, 3.97 mmol) was added as a solution in tetrahydrofuran (10 mL) and the reaction was stirred at room temperature overnight. The reaction was poured into 0.1 N hydrochloric acid solution, neutralized to pH 7 with 2 M hydrochloric acid solution and extracted with ethyl acetate. The combined organics were dried over anhydrous magnesium sulfate and concentrated in vacuo. The residue was purified by flash chromatography using ethyl acetate/hexanes (20/80)+1% formic acid to afford the title compound (0.646 g, 46%) as a white solid. mp=148.9-150° C.; mass spectrum (−ESI, M−H) m/z 338. $^1$H NMR (400 MHz, DMSO-$d_6$); δ 12.30 (bs, 1H), 7.55 (d, 2H), 7.40 (d, 2H). 7.32 (d, 2H), 7.23 (d, 2H), 5.13 (s, 2H), 3.55 (s, 2H), 2.20 (s, 2H), 1.25 (s, 9H). Elemental analysis: Calcd. for $C_{21}H_{25}NO_3$: C, 74.31; H, 7.42; N, 4.13, Found: C, 74.42; H, 7.73; N, 4.15.

Example 3

Synthesis of [4-(4-tert-Butyl-benzylideneaminooxymethyl]-phenyl}-acetic Acid

The title compound was prepared as a white solid (0.193 g, 41%) from 4-tert-butyl-benzaldehyde oxime and 4-bromomethyl-phenyl-acetic acid using a procedure similar to example 2. mp=93.3-96.2° C.; mass spectrum (−APCI, M−H) m/z 324. $^1$H NMR (400 MHz, DMSO-$d_6$); δ 12.30 (bs, 1H), 8.23 (s, 1H), 7.52 (d, 2H), 7.42 (d, 2H), 7.33 (d, 2H), 7.24 (d, 2H), 5.10 (s, 2H), 3.55 (s, 2H), 1.25 (s, 9h). Elemental analysis: Calcd. for $C_{20}H_{23}NO_3$: C, 73.82; H, 7.12; N, 4.30, Found: C, 73.15; H, 7.14; N, 4.01.

Example 4

Synthesis of {4-[3-(4-tert-Butyl-benzylideneaminooxy)-propoxy]-phenyl}-acetic Acid Step 1: {4-[3-(4-tert-Butyl-benzylideneaminooxy)-propoxy]-phenyl}-acetic acid methyl ester was prepared from 1-(4-tert-butyl-phenyl)-ethanone oxime and [4-(3-bromo-propoxy)-phenyl]-acetic acid methyl ester using a procedure similar to step 2 of example 1. It was used crude in the subsequent reaction. $^1$H NMR (300 MHz, CDCl$_3$); δ 8.07 (s, 1H), 7.52 (d, 2H), 7.40 (d, 2H), 7.20 (d, 2H), 6.88 (d, 2H), 4.35 (t, 2H), 4.10 (t, 2H), 3.70 (s, 3H), 3.58 (s, 2H), 2.21 (m, 2H), 1.34 (s, 9H).

Step 2: The title compound was prepared as a white solid (0.280 g, 20%) from {4-[3-(4-tert-butyl-benzylideneami-nooxy)-propoxy]-phenyl}-acetic acid methyl ester using a procedure similar to step 3 of example 1. mp=56.2-59.2° C.; mass spectrum (+APCI, M+H) m/z 370. $^1$H NMR (400 MHz, DMSO-d$_6$); δ 12.20 (bs, 1H), 8.20 (s, 1H), 7.52 (d, 2H), 7.42 (d, 2H), 7.14 (d, 2H), 6.87 (d, 2H), 4.23 (t, 2H), 4.05 (t, 2H), 3.48 (s, 2H), 2.09 (m, 2H), 1.25 (s, 9h). Elemental analysis: Calcd. for C$_{22}$H$_{27}$NO$_4$: C, 71.52; H, 7.37; N, 3.79, Found: C, 69.72; H, 7.27; N, 3.46.

Example 5

Synthesis of 4-{2-[({(E)-1-[4-(tert-Butyl)-phenyl]-ethylidene}amino)oxy]-ethoxy}-2-hydroxy-benzoic Acid Step 1: To a solution of 2,4-dihydroxy-benzoic acid methyl ester (12.254 g, 72.8 mmol) in acetone (120 mL) was added potassium carbonate (30.72 g, 222.3 mmol) and allyl bromide (7 mL, 80.9 mmol). The reaction mixture was heated at reflux for 5 hours, and then cooled to room temperature. It was partitioned between ethyl acetate and brine and the aqueous layer was extracted with ethyl acetate. The combined organics were washed with brine, dried over anhydrous magnesium sulfate and concentrated in vacuo. The residue was purified by flash chromatography using ethyl acetate/hexanes (4/96) to afford 4-allyloxy-2-hydroxy-benzoic acid methyl ester (10.952 g, 77%) as a yellow oil. $^1$H NMR (300 MHz, CDCl$_3$); δ 10.95 (s, 1H), 7.72 (d, 2H), 6.45 (m, 2H), 6.02 (m, 1H), 5.35 (m, 2H), 4.55 (d, 2H), 3.90 (s, 3H).

Step 2: A solution of 4-allyloxy-2-hydroxy-benzoic acid methyl ester(10.952 g, 52.6 mmol) in methanol/methylene chloride (1/1) (300 mL) was cooled to −40° C. then ozone was bubbled through the reaction mixture for 50 minutes. The solution was then purged with nitrogen for 20 minutes, sodium borohydride (2.643 g, 69.86 mmol) was added and warmed to room temperature over 1 hour. The reaction was quenched by the addition of water (20 mL), poured into brine and extracted with ethyl acetate. The combined organics were dried over anhydrous magnesium sulfate and concentrated in vacuo. The residue was purified by flash chromatography using ethyl acetate/hexanes (30/70 to 40/60) to afford 2-hydroxy-4-(2-hydroxy-ethoxy)-benzoic acid methyl ester (9.745 g, 87%) as a white solid. $^1$H NMR (300 MHz, CDCl$_3$); δ 11.00 (s, 1H), 7.75 (d, 2H), 6.46 (m, 2H), 4.11 (t, 2H), 3.98 (t, 2H), 3.93 (s, 3H), 1.90 (bs, 1H).

Step 3: To a solution of 2-hydroxy-4-(2-hydroxy-ethoxy)-benzoic acid methyl ester (3.025 g, 14.25 mmol) in methylene chloride (80 mL) was added carbon tetrabromide (6.216 g, 18.74 mmol) and triphenylphosphine (5.012 g, 19.10 mmol). The reaction was stirred 3 hours at room temperature then additional carbon tetrabromide (1.967 g, 5.931 mmol) and triphenylphosphine (1.568 g, 5.97 mmol) was added and stirring continued overnight. The reaction mixture was concentrated in vacuo and the residue was purified by flash chromatography using ethyl acetate/hexanes (10/90 to 20/80) to afford 4-(2-bromo-ethoxy)-2-hydroxy-benzoic acid methyl ester (3.070 g, 78%) as a white solid. $^1$H NMR (300 MHz, CDCl$_3$); δ 11.00 (s, 1H), 7.76 (d, 2H), 6.46 (m, 2H), 4.32 (t, 2H), 3.93 (s, 3H), 3.65 (t, 2H).

Step 4: To a slurry of sodium hydride (95%) (0.487 g, 20.3 mmol) in tetrahydrofuran (6 mL) was added 1-(4-tert-butyl-phenyl)-ethanone oxime (0.7021 g, 3.67 mmol) as a solution in tetrahydrofuran (18 mL) and the solution was allowed to stir at room temperature for 40 minutes. 4-(2-Bromo-ethoxy)-2-hydroxy-benzoic acid methyl ester (0.908 g, 3.64 mmol) was added as a solution in tetrahydrofuran (10 mL). The reaction was stirred at room temperature 1 hour and then heated at reflux 3 days. The reaction was cooled, quenched with brine and extracted with ethyl acetate. The combined organics were washed with brine, dried over anhydrous magnesium sulfate and concentrated in vacuo. The residue was purified by flash chromatography using ethyl acetate/hexanes (5/95 to 10/90) afford 4-{2-[1-(4-tert-butyl-phenyl)-ethylideneaminooxy]-ethoxy}-2-hydroxy-benzoic acid methyl ester (0.546 g, 39%) as a yellow oil which solidified on standing. mp=65.4-66.8° C.; mass spectrum (+ESI, M+H) m/z 386. $^1$H NMR (400 MHz, DMSO-d$_6$); δ 10.63 (s, 1H), 7.69 (d, 1H), 7.57 (d, 2H), 7.40 (d, 2H), 6.55 (m, 2H), 4.42 (t, 2H), 4.31 (t, 2H), 3.75 (s, 3H), 2.14 (s, 3H), 1.28 (s, 9H). Elemental analysis: Calcd. for C$_{22}$H$_{27}$NO$_5$: C, 68.55; H, 7.06; N, 3.63, Found: C, 68.91; H, 7.10; N, 3.60.

Step 5: To a solution of 4-{2-[1-(4-tert-butyl-phenyl)-ethylideneaminooxy]-ethoxy}-2-hydroxy-benzoic acid methyl ester (0.546 g, 1.29 mmol) in ethanol (10 mL) was added 1 M sodium hydroxide solution (2 mL, 2 mmol) and the reaction was heated at reflux for 40 minutes. After cooling to room temperature, it was concentrated to a small volume, acidified to pH 1 with 2M hydrochloric acid solution and extracted with ethyl acetate. The combined organics were dried over anhydrous magnesium sulfate and concentrated in vacuo. The residue was purified by flash chromatography using ethyl acetate/hexanes (30/70)+1% formic acid to afford the title compound (0.224 g, 47%) as a white solid. mp=157.4-158.7° C.; mass spectrum (+ESI, M+H) m/z 372. $^1$H NMR (400 MHz, DMSO-d$_6$); δ 13.60 (bs, 1H), 11.50 (bs, 1H), 7.67 (d, 1H), 7.57 (d, 2H), 7.40 (d, 2H), 6.52 (m, 2H), 4.40 (t, 2H), 4.30 (t, 2H), 2.13 (s, 3H), 1.27 (s, 9H). Elemental analysis: Calcd. for C$_{21}$H$_{25}$NO$_5$: C, 67.91; H, 6.78; N, 3.77, Found: C, 67.69; H, 6.81; N, 3.68.

Example 6

Synthesis of 2-{[4-(tert-Butyl)benzoyl]oxy}-4-[2-({1-phenylethylidene]amino}oxy)ethoxy]benzoic acid Step 1: To a solution of 1-phenyl-ethanone oxime (1.156 g, 8.55 mmol) in tetrahydrofuran (75 mL) was added 4-(2-bromo-ethoxy)-2-hydroxy-benzoic acid methyl ester (2.346 g, 8.52 mmol), tetrabutylammonium iodide (0.968 g, 2.62 mmol) and 15% sodium hydroxide solution (30 mL). The reaction was heated at reflux overnight, cooled to room temperature and the layers were separated. The aqueous layer was neutralized to pH 7 by the addition of concentrated hydrochloric acid and extracted with ethyl acetate. The combined organics were washed with brine, dried over anhydrous magnesium sulfate and concentrated in vacuo. The residue was purified by flash chromatography using ethyl acetate/hexanes (25/75)+1% formic acid to afford 2-hydroxy-4-[2-(1-phenyl-ethylideneaminooxy)-ethoxy]-benzoic acid (0.712 g, 27%) as a white solid. mp=149.1-150.4° C.; mass spectrum (+APCI, M+H) m/z 316. $^1$H NMR (400 MHz, DMSO-d$_6$); δ 13.60 (bs, 1H), 11.50 (bs, 1H), 7.66 (m, 3H), 7.39 (m, 3H), 6.53 (m, 2H), 4.44 (t, 2H), 4.31 (t, 2H), 2.17 (s, 3H). Elemental analysis: Calcd. for $C_{17}H_{17}NO_5$: C, 67.7; H, 5.43; N, 4.44, Found: C, 64.45; H, 5.32; N, 4.42.

Step 2: To a solution of 2-hydroxy-4-[2-(1-phenyl-ethylideneaminooxy)-ethoxy]-benzoic acid (0.187 g, 0.59 mmol) in methylene chloride (6 mL) was added pyridine (0.120 mL, 1.48 mmol) and 4-tert-butyl benzoyl chloride (0.125 mL, 0.64 mmol). The reaction was stirred at room temperature overnight and then concentrated in vacuo. The residue was partitioned between ethyl acetate and water and the aqueous layer extracted with ethyl acetate. The combined organics dried over anhydrous magnesium sulfate and concentrated in vacuo. The residue was purified by flash chromatography using ethyl acetate/hexanes (10/90 to 30/70)+1% formic acid to afford the title compound (0.084 g, 30%) as a white solid. mp=161.5-163.5° C.; mass spectrum (+APCI, M+H) m/z 470. $^1$H NMR (400 MHz, DMSO-$d_6$); δ 12.60 (bs, 1H), 8.00 (d, 1H), 7.71 (d, 1H), 7.64 (m, 2H), 7.58 (d, 2H), 7.36 (m, 3H), 7.02 (dd, 1H), 6.96 (d, 1H), 4.47 (t, 2H), 4.39 (t, 2H), 2.16 (s, 3H), 1.32 (s, 9H). Elemental analysis: Calcd. for $C_{28}H_{29}NO_6$: C, 70.72; H, 6.15; N, 2.95, Found: C, 66.80; H, 5.87; N, 2.90.

Example 7

Synthesis of 4-{2-[({[4-(tert-Butyl)phenyl] methylidene}amino)oxy]ethoxy}-2-hydroxybenzoic Acid The title compound was prepared as a white solid (3.056 g, 76%) from 4-(2-bromo-ethoxy)-2-hydroxy-benzoic acid methyl ester and 4-tert-butyl-benzaldehyde oxime using a procedure similar to that of step 1 of example 6. mp=161.4-162.7° C.; mass spectrum (+APCI, M+H) m/z 358. $^1$H NMR (400 MHz, DMSO-$d_6$); δ 13.60 (bs, 1H), 11.50 (bs, 1H), 8.24 (s, 1H), 7.68 (d, 1H), 7.54 (d, 2H), 7.42 (d, 2H), 6.52 (m, 2H), 4.40 (t, 2H), 4.29 (t, 2H), 1.38 (s, 9H). Elemental analysis: Calcd. for $C_{20}H_{23}NO_5$: C, 67.21; H, 6.49; N, 3.92, Found: C, 66.86; H, 6.42; N, 3.88.

Example 8

Synthesis of 4-{2-[({(E)-[4-(tert-Butyl)phenyl] methylidene}amino)oxy]ethoxy}-2-{[4-(trifluoromethyl)benzoyl]oxy}benzoic Acid Step 1: To a solution of 4-[2-(4-tert-butyl-benzylideneaminooxy)-ethoxy]-2-hydroxy-benzoic acid (0.614 g, 1.72 mmol) in refluxing benzene (15 mL) was added dimethylformamide di-tertbutyl acetal (2.4 mL, 9.01 mmol). The reaction was heated at reflux 1 hour, additional dimethylformamide di-tertbutyl acetal (1.2 mL, 4.50 mmol) was added and heating continued another hour. It was cooled to room temperature, poured into brine and extracted with ethyl acetate. The combined organics dried over anhydrous magnesium sulfate and concentrated in vacuo. The residue was purified by flash chromatography using ethyl acetate/petroleum ether (8/92) to afford 4-[2-(4-tert-butyl-benzylideneaminooxy)-ethoxy]-2-hydroxy-benzoic acid tert-butyl ester (0.609 g, 86%) as a yellow oil. $^1$H NMR (300 MHz, CDCl$_3$); δ 11.22 (s, 1H), 8.12 (s, 1H), 7.68 (d, 1H), 7.52 (d, 2H), 7.40 (d, 2H), 6.47 (m, 2H), 4.50 (t, 2H), 4.28 (t, 2H), 1.60 (s, 9H), 1.38 (s, 9H).

Step 2: To a solution of 4-[2-(4-tert-butyl-benzylideneaminooxy)-ethoxy]-2-hydroxy-benzoic acid tert-butyl ester (0.298 g, 0.72 mmol) in methylene chloride (10 mL) was added triethylamine (0.200 mL, 1.43 mmol) and 4-trifluoromethyl benzoyl chloride (0.200 mL, 1.42 mmol). The reaction was stirred at room temperature overnight, poured into brine and the aqueous layer extracted with ethyl acetate. The combined organics dried over anhydrous magnesium sulfate and concentrated in vacuo. The residue was purified by flash chromatography using ethyl acetate/hexanes (8/92) to afford 4-{2-[({(E)-[4-(tert-butyl)phenyl]methylidene}amino)oxy]ethoxy}-2-{[4-(trifluoromethyl)benzoyl]oxy}benzoic acid tert-butyl ester (0.405 g, 96%) as a colorless oil. $^1$H NMR (300 MHz, CDCl$_3$); δ 8.33 (d, 2H), 8.12 (s, 1H), 7.97 (d, 1H), 7.78 (d, 2H), 7.52 (d, 2H), 7.38 (d, 2H), 6.92 (dd, 1H), 6.76 (d, 1H), 4.50 (t, 2H), 4.33 (t, 2H), 1.40 (s, 9H), 1.30 (s, 9H).

Step 3: To a solution of 4-{2-[({(E)-[4-(tert-butyl)phenyl] methylidene}amino)oxy]ethoxy}-2-{[4-(trifluoromethyl) benzoyl]oxy}benzoic acid tert-butyl ester (0.387 g, 0.66 mmol) in methylene chloride (15 mL) was added trifluoroacetic acid (0.400 mL, 2.83 mmol). The reaction was stirred at room temperature overnight, poured into brine and the aqueous layer extracted with ethyl acetate. The combined organics dried over anhydrous magnesium sulfate and concentrated in vacuo. The residue was purified by flash chromatography using ethyl acetate/hexanes (20/80)+1% formic acid to afford the title compound (0.300 g, 86%) as a white solid. mp=146.3-147.9° C.; mass spectrum (+APCI, M+H) m/z 530. $^1$H NMR (400 MHz, DMSO-$d_6$); δ 12.70 (bs, 1H), 8.28 (d, 2H), 8.24 (s, 1H), 7.95 (m, 3H), 7.52 (d, 2H), 7.40 (d, 2H), 7.03 (m, 2H), 4.44 (t, 2H), 4.38 (t, 2H), 1.26 (s, 9H). Elemental analysis: Calcd. for $C_{28}H_{26}F_3NO_6$: C, 63.51; H, 4.95; N, 2.65, Found: C, 63.15; H, 4.90; N, 2.64.

Example 9

Synthesis of 4-{2-[({(E)-[4-(tert-Butyl)phenyl] methylidene}amino)oxy]ethoxy}-2-[(4-methoxybenzoyl)oxy]benzoic Acid Step 1: 4-{2-[({(E)-[4-(tert-Butyl)phenyl] methylidene}amino)oxy]ethoxy}-2-[(4-methoxybenzoyl) oxy]benzoic acid tert-butyl ester was prepared as colorless oil (0.112 g, 28%) from 4-[2-(4-tert-butyl-benzylideneaminooxy)-ethoxy]-2-hydroxy-benzoic acid tert-butyl ester using a procedure similar to that of Step 2 of example 8. $^1$H NMR (300 MHz, CDCl$_3$); δ 8.14 (m, 3H), 7.92 (d, 1H), 7.50 (d, 2H), 7.37 (d, 2H), 6.98 (d, 2H), 6.88 (dd, 1H), 6.76 (d, 1H), 4.49 (t, 2H), 4.31 (t, 2H), 3.88 (s, 3H), 1.38 (s, 9H), 1.31 (s, 9H).

Step 2: The title compound was prepared as a white solid (0.062 g, 62%) from 4-{2-[({(E)-[4-(tert-butyl)phenyl] methylidene}amino)oxy]ethoxy}-2-[(4-methoxybenzoyl) oxy]benzoic acid tert-butyl ester using a procedure similar to that of step 3 of example 8. mp=115.5-117.5° C.; mass spectrum (+ESI, M+H) m/z 492. $^1$H NMR (400 MHz, DMSO-$d_6$); δ 12.60 (bs, 1H), 8.24 (s, 1H), 8.02 (d, 2H), 7.90 (d, 1H), 7.53 (d, 2H), 7.40 (d, 2H), 7.10 (d, 2H), 6.98 (dd, 1H), 6.94 (d, 1H), 4.43 (t, 2H), 4.36 (t, 2H), 3.86 (s, 3H), 1.26 (s, 9H). Elemental analysis: Calcd. for $C_{28}H_{29}NO_7$: C, 68.42; H, 5.95; N, 2.85, Found: C, 67.35; H, 5.84; N, 2.76.

Example 10

Synthesis of 2-{[4-(tert-Butyl)benzoyl]oxy}-4-{2-[({(E)-[4-(tert-butyl)phenyl]methylidene}amino) oxy]ethoxy}benzoic Acid.

Step 1: 2-{[4-(tert-Butyl)benzoyl]oxy}-4-{2-[({(E)-[4-(tert-butyl)phenyl]methylidene}amino) oxy]ethoxy}benzoic acid tert-butyl ester was prepared as white foam (0.485 g, 85%) from 4-[2-(4-tert-butyl-benzylideneaminooxy)-ethoxy]-2-hydroxy-benzoic acid tert-butyl ester using a procedure similar to that of Step 2 of example 8. $^1$H NMR (300 MHz, CDCl$_3$); δ 8.15 (m, 3H), 7.93 (d, 1H), 7.52 (m, 4H), 7.38 (d, 2H), 6.88 (dd, 1H), 6.72 (d, 1H), 4.50 (t, 2H), 4.32 (t, 2H), 1.36 (s, 18H), 1.32 (s, 9H).

Step 2: The title compound was prepared as a white solid (0.284 g, 65%) from 2-{[4-(tert-butyl)benzoyl]oxy}-4-{2-[({(E)-[4-(tert-butyl)phenyl]methylidene}amino) oxy] ethoxy}benzoic acid tert-butyl ester using a procedure similar to that of step 3 of example 14. mp=148.1-150.1° C.; mass spectrum (+EI, M+) m/z 517. $^1$H NMR (400 MHz, DMSO-d$_6$); δ 12.60 (bs, 1H), 8.24 (s, 1H), 8.02 (d, 2H), 7.92 (d, 1H), 7.61 (d, 2H), (d, 2H), 7.42 (d, 2H), 7.02 (dd, 1H), 6.94 (d, 1H), 4.44 (t, 2H), 4.37 (t, 2H), 1.32 (s, 9H), 1.25 (s, 9H). Elemental analysis: Calcd. for C$_{31}$H$_{35}$NO$_6$: C, 71.93; H, 6.82; N, 2.71, Found: C, 71.38; H, 6.82; N, 2.67.

Example 11

Synthesis of 2-(Benzoyloxy)-4-{2-[({(E)-[4-(tert-butyl)phenyl]methylidene}amino)oxy] ethoxy}benzoic Acid Step 1: 2-(Benzoyloxy)-4-{2-[({(E)-[4-(tert-butyl)phenyl] methylidene}amino)oxy]ethoxy}benzoic acid tert-butyl ester was prepared as colorless oil (0.175 g, 39%) from 4-[2-(4-tert-butyl-benzylideneaminooxy)-ethoxy]-2-hydroxy-benzoic acid tert-butyl ester using a procedure similar to that of Step 2 of example 8. $^1$H NMR (300 MHz, CDCl$_3$); . 8.22 (d, 2H), 8.12 (s, 1H), 7.95 (d, 1H), 7.64 (m, 1H), 7.50 (m, 4H), 7.38 (d, 2H), 6.89 (dd, 1H), 6.76 (d, 1H), 4.50 (t, 2H), 4.32 (t, 2H), 1.34 (s, 9H), 1.31 (s, 9H).

Step 2: The title compound was prepared as a white solid (0.086 g, 49%) from 2-(benzoyloxy)-4-{2-[({(E)-[4-(tert-butyl)phenyl]methylidene}amino)oxy]ethoxy}benzoic acid tert-butyl ester using a procedure similar to that of step 3 of example 14. mp=129.3-130.6° C.; mass spectrum (+APCI, M+H) m/z 462. $^1$H NMR (400 MHz, DMSO-d$_6$); δ 12.65 (bs, 1H), 8.24 (s, 1H), 8.08 (d, 2H), 7.92 (d, 1H), 7.72 (d, 1H), 7.56 (m, 4H), 7.41 (d, 2H), 7.00 (m, 2H), 4.43 (t, 2H), 4.38 (t, 2H), 1.25 (s, 9H). Elemental analysis: Calcd. for C$_{27}$H$_{27}$NO$_6$: C, 70.27; H, 5.90; N, 3.03, Found: C, 69.94; H, 5.93; N, 2.92.

Example 12

Synthesis of 4-{2-[({(E)-1-[4-(tert-Butyl)phenyl] ethylidene}amino)oxy]-ethoxy}-3-chloro-benzoic Acid Step 1: 4-Allyloxy-3-chloro-benzoic acid methyl ester was prepared as colorless oil (7.16 g, 98%) which solidified on standing from 3-chloro-4-hydroxy-benzoic acid using a procedure similar to that of step 1 of example 11. $^1$H NMR (300 MHz, CDCl$_3$); δ 8.00 (d, 1H), 7.84 (dd, 1H), 6.88 (d, 1H), 6.02 (m, 1H), 5.36 (m, 2H), 4.62 (d, 2H), 3.85 (s, 3H).

Step 2: 3-Chloro-4-(2-hydroxy-ethoxy)-benzoic acid methyl ester was prepared as white solid (6.88 g, 94%) from 4-allyloxy-3-chloro-benzoic acid methyl ester using a procedure similar to that of step 2 of example 5. $^1$H NMR (300 MHz, CDCl$_3$); δ 8.05 (d, 1H), 7.91 (dd, 1H), 6.95 (d, 1H), 4.19 (t, 2H), 4.02 (bt, 2H), 3.89 (s, 3H), 2.38 (bs, 1H).

Step 3: 4-(2-Bromo-ethoxy)-3-chloro-benzoic acid methyl ester was prepared as white solid (8.613 g, 99%) from 3-chloro-4-(2-hydroxy-ethoxy)-benzoic acid methyl ester using a procedure similar to that of step 3 of example 5. $^1$H NMR (300 MHz, CDCl$_3$); δ 8.07 (d, 1H), 7.92 (dd, 1H), 6.93 (d, 1H), 4.40 (t, 2H), 3.89 (s, 3H), 3.70 (t, 2H).

Step 4: The title compound was prepared as white solid (0.334 g, 53%) from 4-(2-bromo-ethoxy)-3-chloro-benzoic acid methyl ester and 1-(4-tert-butyl-phenyl)-ethanone oxime using a procedure similar to that of step 1 of example 6. mp=167.1-168.8° C.; mass spectrum (+APCI, M+H) m/z 390. $^1$H NMR (400 MHz, DMSO-d$_6$); δ 12.95 (bs, 1H), 7.89 (d, 1H), 7.84 (dd, 1H), 7.57 (d, 2H), 7.39 (d, 2H), 7.29 (d, 1H), 4.45 (m, 4H), 2.13 (s, 3H), 1.29 (s, 9H). Elemental analysis: Calcd. for C$_{21}$H$_{24}$ClNO$_4$: C, 64.69; H, 6.20; N, 3.59, Found: C, 64.50; H, 6.28; N, 3.57.

Example 13

Synthesis of 4-{2-[({(E)-1-[4-(tert-Butyl)phenyl] ethylidene}amino)oxy]-ethoxy}-2-chloro-benzoic Acid Step 1: 4-Allyloxy-2-chloro-benzoic acid methyl ester was prepared as a colorless oil (6.04 g, 98%), which solidified on standing, from 2-chloro-4-hydroxy-benzoic acid using a procedure similar to that of step 1 of example 5. $^1$H NMR (300 MHz, CDCl$_3$); δ 7.87 (d, 1H), 6.98 (d, 1H), 6.83 (dd, 1H), 6.02 (m, 1H), 5.38 (m, 2H), 4.58 (d, 2H), 3.90 (s, 3H).

Step 2: 2-Chloro-4-(2-hydroxy-ethoxy)-benzoic acid methyl ester was prepared as colorless oil (5.84 g, 95%) from 4-allyloxy-2-chloro-benzoic acid methyl ester using a procedure similar to that of step 2 of example 5. $^1$H NMR (300 MHz, CDCl$_3$); δ 7.85 (d, 1H), 6.97 (d, 1H), 6.82 (dd, 1H), 4.10 (t, 2H), 3.97 (bt, 2H), 3.87 (s, 3H), 2.11 (bs, 1H).

Step 3: 4-(2-Bromo-ethoxy)-2-chloro-benzoic acid methyl ester was prepared as white solid (8.613 g, 99%) from 2-chloro-4-(2-hydroxy-ethoxy)-benzoic acid methyl ester using a procedure similar to that of step 3 of example 5. $^1$H NMR (300 MHz, CDCl$_3$); δ 7.88 (d, 1H), 6.98 (d, 1H), 6.83 (dd, 1H), 4.32 (t, 2H), 3.90 (s, 3H), 3.65 (t, 2H).

Step 4: The title compound was prepared as white solid (0.334 g, 53%) from 4-(2-bromo-ethoxy)-2-chloro-benzoic acid methyl ester and 1-(4-tert-butyl-phenyl)-ethanone oxime using a procedure similar to that of step 1 of example 6. mp=142.7-143.9° C.; mass spectrum (−ESI, M−H) m/z 388. $^1$H NMR (400 MHz, DMSO-d$_6$); δ 12.97 (bs, 1H), 7.81 (d, 1H), 7.57 (d, 2H), 7.40 (d, 2H), 7.14 (d, 1H), 7.02 (dd, 1H), 4.42 (t, 2H), 4.38 (t, 2H), 2.13 (s, 3H), 1.28 (s, 9H). Elemental analysis: Calcd. for C$_{21}$H$_{24}$ClNO$_4$: C, 64.69; H, 6.20; N, 3.59, Found: C, 64.43; H, 6.20; N, 3.42.

Example 14

Synthesis of 4-{2-[({[4-(tert-Butyl)phenyl] methylidene}amino)oxy]ethoxy}-2-{[4-(trifluoromethyl)benzyl]oxy}benzoic acid The title compound was prepared as a white solid from 4-{2-[({[4-(tert-butyl)phenyl]methylidene}amino)oxy]-ethoxy}-2-hydroxybenzoic acid and 4-trifluromethyl benzyl bromide using a procedure similar to that of step 1 of example 6 followed by a procedure similar to that of step 3 of example 1. mp=164.1-164.8° C.; mass spectrum (+APCI, M+H) m/z 516. $^1$H NMR (400 MHz, DMSO-d$_6$); δ 12.30 (s, 1H), 8.24 (s, 1H), 7.72 (m, 5H), 7.53 (d, 2H), 7.42 (d, 2H), 6.75 (d, 1H), 6.63 (dd, 1H), 5.29 (s, 2H), 4.41 (t, 2H), 4.3 (t, 2H), 1.25 (s, 9H). Elemental analysis: Calcd. for C$_{28}$H$_{28}$F$_3$NO$_5$: C, 65.24; H, 5.47; N, 2.72, Found: C, 63.30; H, 5.21; N, 2.68.

Example 15

Synthesis of 5 2-[([1,1'-Biphenyl]-4-ylcarbonyl) oxy]-4-[2-({[(E)-1-phenylethylidene]amino}oxy) ethoxy]benzoic Acid Step 1: 2-Hydroxy-4-[2-({[1-phenylethylidene] amino}oxy)ethoxy]benzoic acid was prepared as a white solid (0.712 g, 27%) from 4-(2-bromo-ethoxy)-2-hydroxy-benzoic acid methyl ester and 1-phenyl-ethanone oxime using a procedure similar to that of step 1 of example 6. $^1$H NMR (400 MHz, DMSO-d$_6$); δ 13.60 (bs, 1H), 11.50 (bs, 1H), 7.66 (m, 3H), 7.40 (m, 3H), 6.53 (dd, 1H), 6.52 (s, 1H), 4.44 (t, 2H), 4.32 (t, 2H), 2.18 (m, 2H).

Step 2: The title compound was prepared as a white solid (0.076 g, 40%) from 2-hydroxy-4-[2-({[1-phenylethylidene]amino}oxy)ethoxy]benzoic acid and biphenyl-4-carbonyl chloride using a procedure similar to example 8. mp=157.5-159.1° C.; mass spectrum (+EI, M+) m/z 495. $^1$H NMR (400 MHz, DMSO-d$_6$); δ 12.67 (s, 1H), 8.14 (d, 2H), 7.93 (d, 1H), 7.88 (d, 1H), 7.78 (d, 2H), 7.65 (dd, 2H), 7.52 (dd, 2H), 7.45 (dd, 1H), 7.38 (s, 1H), 7.36 (d, 2H), 7.04 (dd, 1H), 7.02 (s, 1H), 4.47(t, 2H), 4.40 (t, 2H), 2.17 (s, 3H). Elemental analysis: Calcd. for $C_{30}H_{25}NO_6$: C, 70.72H, 5.09; N, 2.83, Found: C, 70.92; H, 4.92; N, 2.76.

Example 16

Synthesis of 3-(4-{3-[({(E)-[4-(tert-butyl)phenyl]methylidene}amino)oxy]propoxy}phenyl)propanoic Acid Step 1: 3-[4-(3-Bromo-propoxy)-phenyl]-propionaldehyde was prepared as a colorless oil (2.869 g, 60%) from 3-(4-hydroxy-phenyl)-propionaldehyde and dibromopropane using a procedure similar to step 1 of example 1.

Step 2: The title compound was prepared as a white solid from 3-[4-(3-bromo-propoxy)-phenyl]-propionaldehyde and 4-tert-butyl-benzaldehyde oxime using a procedure similar to step 1 of example 6. mp=101.2-102.1° C.; mass spectrum (−APCI, M−H) n/z 382. $^1$H NMR (400 MHz, DMSO-d$_6$); δ 12.08 (bs, 1H), 8.20 (s, 1H), 7.51 (d, 2H), 7.42 (d, 2H), 7.11 (d, 2H), 6.84 (d, 2H), 4.23 (t, 2H), 4.02 (t, 2H), 2.72 (t, 2H), 2.45 (t, 2H), 2.09 (m, 2H), 1.28 (s, 9H). Elemental analysis: Calcd. for $C_{23}H_{29}NO_4$: C, 72.04; H, 7.62; N, 3.65, Found: C, 71.65; H, 7.77; N, 3.571.

Example 17

Synthesis of 4-(tert-Butyl)benzaldehyde 0-{3-[4-(1H-tetraazol-5-ylmethyl)-phenoxy]-propyl}oxime Step 1: 4-(3-Bromo-propoxy)-benzaldehyde was prepared as a colorless oil (10.642 g, 89%) from 4-hydroxy benzaldehyde and dibromopropane using a procedure similar to step 1 of example 7.

Step 2: 4-tert-Butyl-benzaldehyde O-[3-(4-formyl-phenoxy)-propyl]-oxime (1.453 g, 88%) was prepared as a yellow oil from 4-hydroxy benzaldehyde and 4-tert-butyl-benzaldehyde oxime using a procedure similar to step 1 of example 6. $^1$H NMR (300 MHz, CDCl$_3$); δ 9.85 (s, 1H), 8.04 (s, 1H), 7.80 (d, 2H), 7.47 (d, 2H), 7.36 (d, 2H), 6.98 (d, 2H), 4.32 (t, 2H), 4.18 (t, 2H), 2.21 (m, 2H), 1.30 (s, 9H).

Step 3: To a solution of 4-tert-butyl-benzaldehyde O-[3-(4-formyl-phenoxy)-propyl]-oxime (1.303 g, 3.84 mmol) in methanol (30 mL) was added sodium borohydride (0.201 g, 5.31 mmol) and the reaction was allowed to stir for 20 minutes. It was then poured slowly into brine and extracted with ethyl acetate. The combined organics were washed with brine, dried over magnesium sulfate and concentrated in vacuo to give 4-tert-butyl-benzaldehyde O-[3-(4-hydroxymethyl-phenoxy)-propyl]-oxime which was used without further purification. To a solution of 4-tert-butyl-benzaldehyde O-[3-(4-hydroxymethyl-phenoxy)-propyl]-oxime in methylene chloride (30 mL) was added phosphorus tribromide (0.400 mL, 4.25 mmol) and the reaction was stirred at room temperature for 30 minutes. It was then poured slowly over ice and extracted with ethyl acetate. The combined organics were washed with brine, dried over magnesium sulfate and concentrated in vacuo to give 4-tert-butyl-benzaldehyde O-[3-(4-bromomethyl-phenoxy)-propyl]-oxime (~0.8 g) which was used without further purification. To a solution of 4-tert-butyl-benzaldehyde O-[3-(4-bromomethyl-phenoxy)-propyl]-oxime (~0.8 g) in tetrahydrofuran (25 mL) was added tetrabutylammonium cyanide (0.650 g, 2.42 mmol) and the reaction was allowed to stir at room temperature overnight. It was then poured into brine and extracted with ethyl acetate. The combined organics were washed with brine, dried over magnesium sulfate and concentrated in vacuo. The residue was purified by flash chromatography using ethyl acetate/hexanes (10/90 to 15/85) to give {4-[3-(4-tert-butyl-benzylideneaminooxy)-propoxy]-phenyl}-acetonitrile (0.607 g, 45% over 3 steps) as a colorless oil. $^1$H NMR (300 MHz, CDCl$_3$); δ 8.08 (s, 1H), 7.52 (d, 2H), 7.40 (d, 2H), 7.22 (d, 2H), 6.92 (d, 2H), 4.35 (t, 2H), 4.10 (t, 2H), 3.68 (s, 2H), 2.21 (m, 2H), 1.34 (s, 9H).

Step 4: To a solution of {4-[3-(4-tert-butyl-benzylideneaminooxy)-propoxy]-phenyl}-acetonitrile (0.607 g, 1.5 mmol) in dimethylformamide (10 mL) was added sodium azide (0.583 g, 8.96 mmol) and ammonium chloride (4.82 g, 9.01 mmol) and the reaction was heated at 120° C. for 48 hours. It was then cooled, poured into water, acidified to pH 2 with 2 M HCl and filtered. The precipitate was dissolved in 1N NaOH and extracted with ethyl acetate. The combined organics were washed with brine, dried over magnesium sulfate and concentrated in vacuo. The residue was purified by flash chromatography using methanol/methylene chloride (5/95) to give the title compound as a white solid (0.480 g, 70%). mp=106.3-107.8° C.; mass spectrum +ESI, (M+H) m/z 394. $^1$H NMR (400 MHz, DMSO-d$_6$); 614.00 (bs, 1H), 8.20 (s, 1H), 7.52 (d, 2H), 7.42 (d, 2H), 7.16 (d, 2H), 6.90 (d, 2H), 4.22 (t, 2H), 4.18 (s, 2H), 4.05 (t, 2H), 2.08 (m, 2H), 1.28 (s, 9H). Elemental analysis: Calcd. for $C_{22}H_{27}N_5O_2$: C, 67.15; H, 6.92; N, 17.80, Found: C, 65.64; H, 6.87; N, 17.51.

Example 18

Synthesis of 2-{[4-(tert-Butyl)benzoyl]amino}-4-{3-[({(E)-[4-(tert-butyl)phenyl]methylidene}amino)oxy]propoxy}benzoic Acid Step 1: To a solution of 4-nitro-anthranilic acid (2.200 g, 10.9 mmol, 1 eq) in benzene/methanol (4/1) (100 mL) was added TMSCHN$_2$ (2M in hexanes) (12 mL, 24 mmol, 2.2 eq). The reaction was stirred at room temperature for 30 minutes and then concentrated in vacuo. The residue was purified by flash chromatography using ethyl acetate/hexanes (20/80) to afford 4-nitro-anthranilic acid methyl ester (1.841 g, 86%) as a bright yellow solid. $^1$H NMR (300 MHz, CDCl$_3$); δ 8.00 (d, 1H), 7.50 (d, 1H), 7.40 (dd, 1H), 3.92 (s, 3H).

Step 2: To a solution of 4-nitro-anthranilic acid methyl ester (1.500 g, 7.4 mmol) in CH$_2$Cl$_2$ (200 mL) was added triethylamine (8 mL) and 4-tert-butyl benzoyl chloride and the reaction was stirred overnight at rt. It was then poured into brine, extracted with ethyl acetate, dried over MgSO$_4$ and concentrated in vacuo. The residue was purified by flash chromatography using ethyl acetate/hexanes (20/80) to afford 2-(4-tert-butyl-benzoylamino)-4-nitro-benzoic acid methyl ester (1.841 g, 60%) as a yellow solid. mp=146.0-148.4° C.; mass spectrum (−ES, M−H) in/z 355. $^1$H NMR (400 MHz, DMSO-d$_6$); δ 11.60 (bs, 1H), 9.35 (d, 1H), 8.20 (d, 1H), 8.02 (dd, 1H), 7.90 (d, 2H), 7.64 (d, 2H), 3.95 (s, 3H), 1.36 (s, 9H). Elemental analysis: Calcd. for $C_{19}H_{20}N_2O_5$: C, 64.04; H, 5.66; N, 7.86, Found: C, 64.04; H, 5.79; N, 7.76.

Step 3: To a Parr shaker bottle was added 10% Pd/C (0.346 g) then ethyl acetate (50 mL) followed by 2-(4-tert-butyl-benzoylamino)-4-nitro-benzoic acid methyl ester (3.041 g, 8.53 mmol) as a solution in ethyl acetate (200 mL). The reaction was hydrogenated overnight, filtered through celite and silica washing with ethyl acetate and concentrated in vacuo. The residue was purified by flash chromatography using ethyl acetate/hexanes (20/80) to afford 4-amino-2-(4-tert-butyl-benzoylamino)-benzoic acid methyl ester (2.122 g, 76%) as a yellow solid.

Step 4: To a solution of 4-amino-2-(4-tert-butyl-benzoylamino)-benzoic acid methyl ester (0.711 g, 2.18 mmol) in trifluoroacetic acid cooled to 0° C. was added $NaNO_2$ (0.182 g, 2.64 mmol, 1.21 eq) as a solution in water (4 mL) and the reaction was stirred for 5 minutes. It was then added dropwise to a 30% solution of $H_2SO_4$ (50 mL) at 65° C. and stirred for 15 minutes. It was extracted with ethyl acetate, dried over $MgSO_4$ and concentrated in vacuo. The residue was purified by flash chromatography using ethyl acetate/hexanes (20/80) to afford 2-(4-tert-butyl-benzoylamino)-4-hydroxy-benzoic acid methyl ester (0.508, 71%) as a white solid. mp=146.0-148.4° C.; mass spectrum (−ES, M−H) m/z 326. $^1$H NMR (400 MHz, DMSO-$d_6$); δ 11.95 (bs, 1H), 10.60 (bs, 1H), 8.26 (d, 1H), 7.88 (m, 3H), 7.62 (d, 2H), 6.58 (dd, 1H), 3.85 (s, 3H), 1.32 (s, 9H). Elemental analysis: Calcd. for $C_{19}H_{21}NO_4$: C, 69.71; H, 6.47; N, 4.28, Found: C, 69.20; H, 6.54; N, 4.17.

Step 5: 4-(3-Bromo-propoxy)-2-(4-tert-butyl-benzoylamino)-benzoic acid methyl ester was prepared as a colorless oil (0.139 g, 83%) from 2-(4-tert-butyl-benzoylamino)-4-hydroxy-benzoic acid methyl ester and dibromopropane using a procedure similar to step 1 of example 1. $^1$H NMR (300 MHz, CDCl$_3$); δ 12.02 (s, 1H), 8.63 (d, 1H), 8.00 (m, 3H), 7.54 (d, 2H), 6.63 (dd, 1H), 4.23 (t, 2H), 3.93 (s, 3H), 3.60 (t, 2H), 2.35 (m, 2H), 1.38 (s, 9H).

Step 6: The title compound was (0.150 g, 91%) prepared as a white solid from 4-(3-bromo-propoxy)-2-(4-tert-butyl-benzoylamino)-benzoic acid methyl ester and 4-tert-butyl-benzaldehyde oxime using a procedure similar to step 1 of example 6. mp=192.3-193.8° C.; mass spectrum +ESI, (M+H) m/z 531. $^1$H NMR (400 MHz, DMSO-$d_6$); δ13.40 (bs, 1H), 12.50 (s, 1H), 8.45 (d, 1H), 8.21 (s, 1H), 7.98 (d, 1H), 7.86 (d, 2H), 7.60 (d, 2H), 7.50 (d, 2H), 7.38 (d, 2H), 6.76 (dd, 1H), 4.27 (t, 2H), 4.18 (t, 2H), 2.16 (m, 2H), 1.32 (s, 9H), 1.23 (s, 9H). Elemental analysis: Calcd. for $C_{32}H_{38}N_2O_5$: C, 72.43; H, 7.22; N, 5.28, Found: C, 70.96; H, 7.29; N, 5.05.

Example 19

Synthesis of 4-{3-[({(E)-[3,5-Bis(trifluoromethyl) phenyl]methylidene}amino)oxy]propoxy}-2-hydroxybenzoic Acid Step 1: 4-(3-Bromo-propoxy)-2-hydroxy-benzoic acid methyl ester was prepared as a white solid (6.478 g, 75%) from 2,4-dihydroxy-benzoic acid methyl ester and dibromopropane using a procedure similar to step 1 of example 1. $^1$H NMR (300 MHz, CDCl$_3$); δ 10.85 (s, 1H), 8.63 (d, 1H), 7.50 (d, 1H), 6.42 (m, 2H), 4.10 (t, 2H), 3.88 (s, 3H), 3.55 (t, 2H), 2.28 (m, 2H).

Step 2: The title compound (0.115 g, 12%) was prepared as a white solid from 4-(3-bromo-propoxy)-2-hydroxy-benzoic acid methyl ester and 3,5-bis-trifluoromethyl-benzaldehyde oxime using a procedure similar to step 1 of example 12. mp=181.9-183.4° C.; mass spectrum −ESI, (M−H) m/z 450. $^1$H NMR (400 MHz, DMSO-$d_6$); 613.60 (bs, 1H), 11.50 (bs, 1H), 8.48 (s, 1H), 8.23 (s, 2H), 8.13 (s, 1H), 7.66 (d, 1H), 6.47 (m, 2H), 4.33 (t, 2H), 4.12 (t, 2H), 2.12 (m, 2H). Elemental analysis: Calcd. for $C_{19}H_{15}F_6NO_5$: C, 50.56; H, 3.35; N, 3.1, Found: C, 50.25; H, 3.32; N, 2.93.

Example 20

Synthesis of 4-[3-({[(1E)-1,1'-Biphenyl-4-ylmethylidene]amino}oxy)propoxy]-2-{[4-(trifluoromethyl)benzoyl]amino}benzoic Acid Step 1: 4-Nitro-2-(4-trifluoromethyl-benzoylamino)-benzoic acid methyl ester (3.352 g, 67%) was prepared from 4-nitro-antranilic acid methyl ester and 4-trifluoromethyl benzoyl chloride using a procedure similar to step 2 of example 18. $^1$H NMR (300 MHz, CDCl$_3$); δ 12.20 (bs, 1H), 9.80 (d, 1H), 8.27 (d, 1H), 8.15 (d, 2H), 7.95 (dd, 1H), 7.82 (d, 2H), 4.08 (s, 3H).

Step 2: 4-Amino-2-(4-trifluoromethyl-benzoylamino)-benzoic acid methyl ester (2.593 g, 84%) was prepared from 4-nitro-2-(4-trifluoromethyl-benzoylamino)-benzoic acid methyl ester using a procedure similar to step 3 of example 18. $^1$H NMR (300 MHz, CDCl$_3$); δ 12.40 (s, 1H), 8.25 (d, 1H), 8.14 (d, 2H), 7.89 (d, 1H), 7.78 (d, 2H), 6.37 (dd, 1H), 4.30 (bs, 2H), 3.90 (s, 3H).

Step 3: 4-Hydroxy-2-(4-trifluoromethyl-benzoylamino)-benzoic acid methyl ester (1.073 g, 44%) was prepared from 4-amino-2-(4-trifluoromethyl-benzoylamino)-benzoic acid methyl ester using a procedure similar to step 4 of example 18. $^1$H NMR (300 MHz, CDCl$_3$); δ 12.60 (s, 1H), 9.30 (s, 1H), 8.80 (d, 1H), 8.14 (d, 2H), 8.05 (d, 1H), 7.83 (d, 2H), 6.70 (dd, 1H), 3.90 (s, 3H).

Step 4: 4-(3-Bromo-propoxy)-2-(4-trifluoromethyl-benzoylamino)-benzoic acid methyl ester was prepared as a colorless oil (0.952 g, 65%) from 2-(4-tert-butyl-benzoylamino)-4-hydroxy-benzoic acid methyl ester and dibromopropane using a procedure similar to step 1 of example 1. $^1$H NMR (300 MHz, CDCl$_3$); δ 12.40 (bs, 1H), 8.58 (d, 1H), 8.16 (d, 2H), 8.02 (d, 1H), 7.79 (d, 2H), 6.67 (dd, 1H), 4.23 (t, 2H), 3.92 (s, 3H), 3.60 (t, 2H), 2.35 (m, 2H).

Step 5: The title compound was (0.150 g, 91%) prepared as a white solid from 4-(3-bromo-propoxy)-2-(4-trifluoromethyl-benzoylamino)-benzoic acid methyl ester and biphenyl-4-carbaldehyde oxime using a procedure similar to step 1 of example 6. mp=205.6-206.6° C.; mass spectrum API-ES, (M−H) m/z 561. $^1$H NMR (400 MHz, DMSO-$d_6$); δ 13.40 (bs, 1H), 12.60 (s, 1H), 8.41 (d, 1H), 8.31 (s, 1H), 8.12 (d, 2H), 8.01 (d, 1H), 7.96 (d, 2H), 7.66 (m, 6H), 7.45 (dd, 2H), 7.38 (dd, 1H), 6.82 (dd, 1H), 4.32 (t, 2H), 4.21 (t, 2H), 2.18 (m, 2H). Elemental analysis: Calcd. for $C_{31}H_{25}F_3N_2O_5$: C, 66.19; H, 4.48; N, 4.98, Found: C, 65.8; H, 4.48; N, 4.82.

Example 21

Synthesis of 4-[3-({[(1E)-1-(4-tert-butylphenyl)propylidene]amino}oxy) propoxy]-2-{[4-(trifluoromethyl)benzoyl]amino}benzoic Acid The title compound was (0.032 g, 891%) prepared as a white solid from 4-(3-bromo-propoxy)-2-(4-trifluoromethyl-benzoylamino)-benzoic acid methyl ester and 1-(4-tert-butylphenyl)-propan-1-one oxime using a procedure similar to step 1 of example 6. mp=149.4-151.0° C.; mass spectrum +ES, (M+H) m/z 571. $^1$H NMR (400 MHz, DMSO-$d_6$); δ 13.50 (bs, 1H), 12.65 (s, 1H), 8.38 (d, 1H), 8.12 (d, 2H), 7.98 (m, 3H), 7.54 (d, 2H), 7.36 (d, 2H), 6.80 (dd, 1H), 4.28 (t, 2H), 4.20 (t, 2H), 2.70 (q, 2H), 2.15 (m, 2H), 1.22 (s, 9H), 1.06 (t, 3H). Elemental analysis: Calcd. for $C_{31}H_{33}F_3N_2O_5$: C, 65.25; H, 5.83; N, 4.91, Found: C, 63.7; H, 5.50; N, 4.60.

Example 22

Synthesis of 2-{[4-(Trifluoromethyl)benzoyl] amino}-4-{3-[({(1E)-[4-(trifluoromethyl)phenyl] methylidene}amino)oxy]propoxy}benzoic Acid The title compound was (0.032 g, 89%) prepared as a white solid from 4-(3-bromo-propoxy)-2-(4-trifluoromethyl-benzoylamino)-benzoic acid methyl ester and 4-Trifluoromethyl-benzaldehyde oxime using a procedure similar to step 1 of example 6. mp=208.6-209.6° C.; mass spectrum −ES, (M−H) m/z 553. $^1$H NMR (400 MHz, DMSO-d$_6$); δ 13.40 (bs, 1H), 12.9 (bs, 1H), 8.38 (m, 2H), 8.12 (d, 2H), 7.97 (m, 3H), 7.80 (d, 2H), 7.73 (d, 2H), 6.79 (dd, 1H), 4.34 (t, 2H), 4.20 (t, 2H), 2.18 (m, 2H). Elemental analysis: Calcd. for C$_{26}$H$_{20}$F$_6$N$_2$O$_5$: C, 56.32; H, 3.64; N, 5.05, Found: C, 55.87; H, 3.54; N, 4.91.

Example 23

Synthesis of 4-[3-({[(1E)-1-Phenylethylidene] amino}oxy)propoxy]-2-{[4-(trifluoromethyl)benzoyl]amino}benzoic acid The title compound was (0.075 g, 42%) prepared as a white solid from 4-(3-bromo-propoxy)-2-(4-trifluoromethyl-benzoylamino)-benzoic acid methyl ester and 1-phenyl-ethanone oxime using a procedure similar to step 1 of example 6. mp=174.3-175.7° C.; mass spectrum API-ES, (M−H) m/z 499. $^1$H NMR (400 MHz, DMSO-d$_6$); δ 13.50 (bs, 1H), 12.51 (bs, 1H), 8.38 (d, 2H), 8.12 (d, 2H), 8.00 (m, 4H), 7.76 (dd, 2H), 7.36 (m, 3H), 6.82 (dd, 1H), 4.30 (t, 2H), 4.20 (t, 2H), 2.18 (m, 2H). Elemental analysis: Calcd. for C$_{26}$H$_{23}$F$_3$N$_2$O$_5$: C, 62.40; H, 4.63; N, 5.60, Found: C, 59.75; H, 4.42; N, 5.06.

Example 24

Synthesis of 4-[3-({[(1E)-(4-tert-Butylphenyl)methylidene]amino}oxy)propoxy]-2-{[2-(trifluoromethyl)benzoyl]amino}benzoic acid Step 1: 4-Nitro-2-(2-trifluoromethyl-benzoylamino)-benzoic acid methyl ester (5.103 g, 91%) was prepared from 4-nitro-antranilic acid methyl ester and 2-trifluoromethyl benzoyl chloride using a procedure similar to step 2 of example 18. $^1$H NMR (300 MHz, DMSO-d$_6$); δ 11.30 (s, 1H), 8.96 (d, 1H), 8.18 (m, 2H), 7.80 (m, 4H), 3.85 (s, 3H).

Step 2: 4-Amino-2-(2-trifluoromethyl-benzoylamino)-benzoic acid methyl ester (1.072 g, 65%) was prepared from 4-nitro-2-(2-trifluoromethyl-benzoylamino)-benzoic acid methyl ester using a procedure similar to step 3 of example 18. $^1$H NMR (300 MHz, DMSO-d$_6$); δ 11.60 (s, 1H), 7.80 (m, 6H), 6.34 (m, 3H), 3.70 (s, 3H).

Step 3: 4-Hydroxy-2-(2-trifluoromethyl-benzoylamino)-benzoic acid methyl ester (1.454 g, 75%) was prepared from 4-amino-2-(2-trifluoromethyl-benzoylamino)-benzoic acid methyl ester using a procedure similar to step 4 of example 18. $^1$H NMR (300 MHz, DMSO-d$_6$); δ 11.40 (s, 1H), 10.62 (s, 1H), 8.08 (d, 1H), 7.84 (m, 5H), 6.64 (dd, 1H), 3.78 (s, 3H).

Step 4: 4-(3-Bromo-propoxy)-2-(2-trifluoromethyl-benzoylamino)-benzoic acid methyl ester was prepared as a colorless oil (1.384 g, 70%) from 2-(2-trifluoromethyl-benzoylamino)-4-hydroxy-benzoic acid methyl ester and dibromopropane using a procedure similar to step 1 of example 1. $^1$H NMR (300 MHz, CDCl$_3$); δ 11.60 (bs, 1H), 8.50 (d, 1H), 8.00 (d, 1H), 7.76 (d, 1H), 7.64 (m, 3H), 6.66 (dd, 1H), 4.23 (t, 2H), 3.84 (s, 3H), 3.61 (t, 2H), 2.35 (m, 2H).

Step 5: The title compound (0.117 g, 64%) was prepared as a white solid from 4-(3-bromo-propoxy)-2-(2-trifluoromethyl-benzoylamino)-benzoic acid methyl ester and 4-tert-butyl-benzaldehyde oxime using a procedure similar to step 1 of example 6. mp=121.1-122.0° C.; mass spectrum API-ES, (M−H) m/z 541. $^1$H NMR (400 MHz, DMSO-d$_6$); δ 13.40 (bs, 1H), 11.90 (bs, 1H), 8.28 (d, 1H), 8.22 (s, 1H), 7.96 (d, 1H), 7.88 (d, 1H), 7.80 (m, 3H), 7.50 (d, 2H), 7.39 (d, 2H), 6.82 (dd, 1H), 4.28 (t, 2H), 4.18 (t, 2H), 2.15 (m, 2H), 1.25 (s, 9H). Elemental analysis: Calcd. for C$_{29}$H$_{29}$F$_3$N$_2$O$_5$: C, 62.2; H, 5.39; N, 5.16, Found: C, 63.8; H, 5.26; N, 5.04.

Example 25

Synthesis of 2-{[2-(Trifluoromethyl)benzoyl] amino}-4-{3-[({(1E)-[4-(trifluoromethyl)phenyl] methylidene}amino)oxy]propoxy}benzoic acid The title compound (0.404 g, 70%) was prepared as a white solid from 4-(3-bromo-propoxy)-2-(2-trifluoromethyl-benzoylamino)-benzoic acid methyl ester and 4-trifluoromethyl-benzaldehyde oxime using a procedure similar to step 1 of example 6. mp=147.2-147.9° C.; mass spectrum −ES, (M−H) m/z 553. $^1$H NMR (400 MHz, DMSO-d$_6$); δ 13.40 (bs, 1H), 11.90 (bs, 1H), 8.38 (s, 1H), 8.26 (d, 1H), 7.97 (d, 1H), 7.86 (d, 1H), 7.77 (m, 7H), 6.81 (dd, 1H), 4.33 (t, 2H), 4.18 (t, 2H), 2.18 (m, 2H). Elemental analysis: Calcd. for C$_{26}$H$_{20}$F$_6$N$_2$O$_5$: C, 56.32; H, 3.64; N, 5.05, Found: C, 55.83; H, 3.27; N, 4.88.

Example 26

Synthesis of 4-[3-({[(1E)-1,1'-biphenyl-4-ylmethylidene]amino}oxy)propoxy]-2-{[2-(trifluoromethyl) benzoyl]amino}benzoic Acid The title compound (0.193 g, 92%) was prepared as a white solid from 4-(3-bromo-propoxy)-2-(2-trifluoromethyl-benzoylamino)-benzoic acid methyl ester and Biphenyl-4-carbaldehyde oxime using a procedure similar to step 1 of example 6. mp=170.5-172.5° C.; mass spectrum API-ES, (M−H) m/z 561. $^1$H NMR (400 MHz, DMSO-d$_6$); δ 13.40 (bs, 1H), 12.00 (bs, 1H), 8.32 (s, 1H), 8.27 (d, 1H), 7.98 (d, 1H), 7.88 (d, 1H), 7.81 (m, 2H), 7.76 (m, 1H), 7.68 (m, 6H), 7.46 (m, 2H), 7.38 (m, 1H), 6.82 (dd, 1H), 4.32 (t, 2H), 4.20 (t, 2H), 2.20 (m, 2H). Elemental analysis: Calcd. for C$_{31}$H$_{25}$F$_3$N$_2$O$_5$: C, 66.19; H, 4.48; N, 4.98, Found: C, 65.26; H, 4.49; N, 4.77.

Example 27

Synthesis of 2-{[3,5-Bis(trifluoromethyl)benzoyl] amino}-4-[3-({[(1E)-(4-tert-butylphenyl)methylidene]amino}oxy)propoxy]benzoic Acid Step 1: To a solution of 2-amino-4-nitro-benzoic acid methyl ester (5.00 g, 25.5 mmol) in methylene chloride (75 mL) was added triethylamine (4.13 g, 40.8 mmol) followed by 3,5-bis-trifluoromethyl-benzoyl chloride (8.46 g, 30.6 mmol). This mixture was allowed to stir overnight at ambient temperature. Work-up of an aliquot of the reaction mixture revealed incomplete reaction. Additional 0.5 equivalents of the acid chloride (2.3 mL) and triethylamine (1.8 mL) were added and the mixture was refluxed overnight. The reaction mixture was allowed to cool and filtered. The filtrate was partitioned against brine, the layers were separated, and the aqueous layer was extracted with one portion of ethyl acetate. The organics were combined, dried over MgSO$_4$, filtered and concentrated under reduced pressure. The resultant paste was dissolved in methylene chloride (25 mL) and the product was precipitated out by the addition of hexanes (175 mL). The precipitate was isolated by filtration and determined to be a mixture of the desired amide (mono-acylated) product and the carbamate (di-acylated) side product. The crude material was purified by flash chromatography through silica gel using ethyl acetate/hexanes (15/85 gradient to 30/70) to give 2-(3, 5-bis-trifluoromethyl-benzoylamino)-4-nitro-benzoic acid methyl ester (3.7 g, 33%) as an off-white solid. $^1$H NMR (400 MHz, CDCl$_3$); δ 12.40 (bs, 1H), 9.78 (d, 1H), 8.50 (s, 2H), 8.31 (d, 1H), 8.11 (s, 1H), 8.00 (dd, 1H), 4.07 (s, 3H). $^1$H NMR (400 MHz, DMSO-d$_6$); δ 9.04 (d, 1H), 8.43 (dd, 1H), 8.34 (s, 4H), 8.24 (s, 1H), 8.22 (s, 2H), 3.87 (s, 3H).

Step 2: To a solution of 2-(3,5-bis-trifluoromethyl-benzoylamino)-4-nitro-benzoic acid methyl ester (1.85 g, 4.24 mmol) in ethyl acetate (250 mL) in a Parr flask was added 10% palladium on carbon (0.20 g). The flask was attached to a Parr shaker and purged with nitrogen gas. The flask was then charged to 50 psi with hydrogen gas and the shaker was activated. After 2 hours the apparatus was recharged to 50 psi with hydrogen gas and the mixture was allowed to agitate. After an additional 2 hours the apparatus was recharged to 50 psi with hydrogen gas and the mixture was allowed to agitate for 4 additional hours (8 hours total time). The mixture was removed from the apparatus and filtered through a plug of Celite. The Celite was rinsed with ethyl acetate until no more color came through and the filtrate was concentrated under reduced pressure. The crude material was dissolved in ethyl acetate, dried over MgSO$_4$, filtered and concentrated under reduced pressure to give 4-amino-2-(3,5-bis-trifluoromethyl-benzoylamino)-benzoic acid methyl ester (1.70 g, 99%) as a yellow solid. $^1$H NMR (400 MHz, DMSO-d$_6$); δ 13.52 (s, 1H), 8.49 (s, 2H), 8.44 (s, 1H), 7.83 (d, 1H), 7.73 (d, 1H), 6.40-6.36 (m, 2H), 6.37 (s, 2H), 6.36 (dd, 1H), 3.80 (s, 3H).

Step 3: To a solution of 4-amino-2-(3,5-bis-trifluoromethyl-benzoylamino)-benzoic acid methyl ester (1.70 g, 4.18 mmol) in trifluoroacetic acid (25 mL) which has been cooled to 0° C. was slowly added a solution of sodium nitrite (0.35 g, 5.06 mmol in 9 mL of water). In a separate flask, concentrated sulfuric acid (21 m]L) was added to water (50 mL) to make a 30% sulfuric acid solution. After 5 minutes, the trifluoroacetic acid mixture was slowly added to the sulfuric acid solution. After complete addition, the reaction mixture was allowed to stir at ambient temperature for 15 minutes. The reaction mixture was extracted with three portions of ethyl acetate. The organics were combined, dried over anhydrous magnesium sulfate, filtered and concentrated under reduced pressure. The crude material was purified by flash chromatography through silica gel using ethyl acetate/hexanes (20/80) to give 2-(3,5-bis-trifluoromethyl-benzoylamino)-4-hydroxy-benzoic acid methyl ester (1.30 g, 76%) as a yellow solid. $^1$H NMR (400 MHz, DMSO-d$_6$); δ 11.92 (s, 1H), 10.68 (s, 1H), 8.50 (s, 2H), 8.44 (s, 1H), 8.03 (d, 1H), 7.88 (d, 1H), 6.64 (dd, 1H), 3.84 (s, 3H).

Step 4: To a solution of 2-(3,5-bis-trifluoromethyl-benzoylamino)-4-hydroxy-benzoic acid methyl ester (10.10 g, 2.70 mmol) and 1,3-dibromopropane (2.18 g, 10.8 mmol) in acetone (75 mL) was added potassium carbonate (1.87 g, 13.5 mmol). The reaction mixture was heated to reflux for 3 hours and allowed to cool back down to room temperature. The mixture was partitioned between ethyl acetate and brine, and the layers were separated. The aqueous layer was extracted with one additional portion of ethyl acetate. The organics were combined, washed with one portion of brine, dried over anhydrous magnesium sulfate, filtered and concentrated under reduced pressure. The crude oil was purified by flash chromatography through silica gel using ethyl acetate/hexanes (0/100 gradient to 8/92) to give 2-(3,5-bis-trifluoromethyl-benzoylamino)-4-(3-bromo-propoxy)-benzoic acid methyl ester (1.11 g, 78%) as a white powder. $^1$H NMR (400 MHz, CDCl$_3$); δ 12.58 (s, 1H), 8.53 (d, 1H), 8.51 (s, 2H), 8.08 (s, 1H), 8.04 (d, 1H), 6.70 (dd, 1H), 4.24 (t, 2H), 3.96 (s, 3H), 3.62 (t, 2H), 2.37 (m, 2H).

Step 5: To a solution of 2-(3,5-bis-trifluoromethyl-benzoylamino)-4-(3-bromo-propoxy)-benzoic acid methyl ester (0.53 g, 1.00 mmol) and 4-tert-butyl-benzaldehyde oxime (0.20 g, 1.10 mmol) in acetone (35 mL) was added cesium carbonate (1.30 g, 4.00 mmol). The mixture was heated to reflux overnight and then allowed to cool back to room temperature. The mixture was partitioned between ethyl acetate and brine and the layers were then separated. The aqueous layer was extracted with two additional portions of ethyl acetate. The organics were combined, dried over anhydrous magnesium sulfate, filtered and concentrated under reduced pressure. The crude oil was purified by flash chromatography through silica gel using diethyl ether/hexanes (0/100 gradient to 5/95) to give 2-{[3,5-bis(trifluoromethyl)benzoyl]amino}-4-[3-({[(1E)-(4-tert-butylphenyl)methylidene]amino}oxy)propoxy]benzoic acid methyl ester (0.30 g, 48%) as an off-white solid. $^1$H NMR (400 MHz, CDCl$_3$); δ 12.52 (s, 1H), 8.51 (d, 1H), 8.48 (s, 2H), 8.06 (s, 1H), 8.04 (s, 1H), 7.99 (d, 1H), 7.47-7.35 (AA'BB', 4H), 6.67 (dd, 1H), 4.34 (t, 2H), 4.22 (t, 2H), 3.92 (s, 3H), 2.23 (m, 2H), 1.28 (s, 9H).

Step 6: To a solution 2-{[3,5-bis(trifluoromethyl)benzoyl]amino}-4-[3-({[(1E)-(4-tert-butylphenyl)methylidene]amino}oxy)propoxy]benzoic acid methyl ester (0.30 g, 0.48 mmol) in ethanol (20 mL) was added 1.0 N, sodium hydroxide solution (4 mL). This mixture was heated to reflux for 20 minutes and then allowed to cool back to room temperature. Water (5 mL) was added to the mixture, it was concentrated to approximately ¼ volume and then partitioned between ethyl acetate and water. The aqueous layer was acidified to approximately pH 3 using 1 N hydrochloric acid. The layers were then separated. The aqueous layer was extracted with two additional portions of ethyl acetate. The organics were combined, dried over anhydrous magnesium sulfate, filtered and concentrated under reduced pressure. The crude material was purified by flash chromatography through silica gel using ethyl acetate/hexanes (10/90 with 1% formic acid gradient to 20/80 with 1% formic acid) and then recrystallized one time from chloroform/hexanes (1/20) to give 2-{[3,5-bis(trifluoromethyl)benzoyl]amino}-4-[3-({[(1E)-(4-tert-butylphenyl)methylidene]amino}oxy)propoxy]benzoic acid (0.13 g, 45%) as a white powder. mp=157.5-158.5° C. $^1$H NMR (500 MHz, DMSO-d$_6$); δ 13.54 (bs, 1H), 12.54 (s, 1H), 8.51 (s, 2H), 8.45 (s, 1H), 8.32 (d, 1H), 8.21 (s, 1H), 8.00 (d, 1H), 7.50-7.37 (AA'BB', 4H), 6.83 (dd, 1H), 4.27 (t, 2H), 4.21 (t, 2H), 2.16 (m, 2H), 1.23 (s, 9H). Mass spec (MW 610.55); (ES–) m/z 609.2. Elemental analysis; Calculated for C$_{30}$H$_{28}$F$_6$N$_2$O$_5$: C, 59.02; H, 4.62; N, 4.59. Found: C, 58.78; H, 4.52; N, 4.46.

Example 28

Synthesis of 4-{3-[({(1E)-[3,5-Bis (trifluoromethyl)phenyl]methylidene}amino)oxy]propoxy}-2-{[4-(trifluoromethoxy)benzoyl]amino}benzoic Acid Step 1: To a solution of 2-amino-4-nitro-benzoic acid methyl ester (5.00 g, 25.5 mmol) in methylene chloride (75 mL) was added triethylamine (4.13 g, 40.8 mmol) followed by 4-trifluoromethoxy-benzoyl chloride (6.87 g, 30.6 mmol). This mixture was allowed to stir overnight at ambient temperature. The mixture was filtered, partitioned against brine, the layers were separated, and the aqueous layer was extracted with one portion of ethyl acetate. The organics were combined, dried over MgSO$_4$, filtered and concentrated under reduced pressure. The crude material was recrystalized from ethyl acetate (250 mL) to give 4-nitro-2-(4-trifluoromethoxy-benzoylamino)-benzoic acid methyl ester (6.83 g, 70%) as pale-yellow crystals. $^1$H NMR (500 MHz, DMSO-d$_6$); δ 11.53 (s, 1H), 9.20 (d, 1H), 8.19 (d, 1H), 8.10 (d, 2H), 8.07 (dd, 1H), 7.63 (d, 2H), 3.91 (s, 3H).

Step 2: This compound was produced using similar methods as those used in Step 2, example 27, starting with 4-nitro-2-(4-trifluoromethoxy-benzoylamino)-benzoic acid methyl ester (2.00 g, 5.20 mmol) in ethyl acetate (250 mL) and 10% palladium on carbon (0.20 g). The crude 4-amino-2-(4-trifluoromethoxy-benzoylamino)-benzoic acid methyl ester (1.70 g, 99%) was used without further purification. $^1$H NMR (400 MHz, CDCl$_3$); δ 12.32 (s, 1H), 8.25 (d, 1H), 8.09 (d, 2H), 7.89 (d, 1H), 7.35 (d, 2H), 6.37 (dd, 1H), 3.90 (s, 3H).

Step 3: This compound was produced using similar methods as those used in Step 3, example 27, starting with 4-amino-2-(4-trifluoromethoxy-benzoylamino)-benzoic acid methyl ester (1.80 g, 5.08 mmol), trifluoroacetic acid (30 mL) and sodium nitrite (0.42 g, 6.15 mmol in 10 mL of water). The crude material was purified by flash chromatography through silica gel using ethyl acetate/hexanes (0/100 gradient to 20/80) to give 4-hydroxy-2-(4-trifluoromethoxy-benzoylamino)-benzoic acid methyl ester (1.49 g, 83%) as a yellow solid. $^1$H NMR (400 MHz, DMSO-d$_6$); δ 11.98 (s, 1H), 10.62 (s, 1H), 8.21 (d, 1H), 8.06 (d, 2H), 7.90 (d, 1H), 7.61 (d, 2H), 6.61 (dd, 1H), 3.84 (s, 3H).

Step 4: This compound was produced using similar methods as those used in Step 4, example 27, starting with 4-hydroxy-2-(4-trifluoromethoxy-benzoylamino)-benzoic acid methyl ester (1.49 g, 4.19 mmol), 1,3-dibromopropane (3.39 g, 16.8 mmol) and potassium carbonate (2.90 g, 21.0 mmol) in acetone (85 mL). The crude oil was purified by flash chromatography through silica gel using ethyl acetate/hexanes (0/100 gradient to 12/88) to give 4-(3-bromo-propoxy)-2-(4-trifluoromethoxy-benzoylamino)-benzoic acid methyl ester (1.49 g, 75%) as a white powder. $^1$H NMR (400 MHz, CDCl$_3$); δ 12.30 (s, 1H), 8.57 (d, 1H), 8.10 (d, 2H), 8.02 (d, 1H), 7.36 (d, 2H), 6.65 (dd, 1H), 4.24 (t, 2H), 3.93 (s, 3H), 3.61 (t, 2H), 2.35 (m, 2H).

Step 5: This compound was produced using similar methods as those used in Step 5, example 27, starting with 4-(3-bromo-propoxy)-2-(4-trifluoromethoxy-benzoylamino)-benzoic acid methyl ester (0.56 g, 1.18 mmol), 3,5-bis-trifluoromethyl-benzaldehyde oxime (0.32 g, 1.23 mmol) and cesium carbonate (1.53 g, 4.70 mmol) in acetone (35 mL). The crude material was purified by flash chromatography through silica gel using diethyl ether/hexanes (0/100 gradient to 10/90) to give 4-{3-[({(1E)-[3,5-bis(trifluoromethyl)phenyl]methylidene}amino)oxy]propoxy}-2-{[4-(trifluoromethoxy)benzoyl]amino}benzoic acid methyl ester (0.61 g, 94%) as a white solid. $^1$H NMR (400 MHz, CDCl$_3$); δ 12.26 (s, 1H), 8.56 (d, 1H), 8.13 (s, 1H), 8.06 (d, 2H), 7.98 (d, 1H), 7.97 (s, 2H), 7.80 (s, 1H), 7.33 (d, 2H), 6.64 (dd, 1H), 4.41 (t, 2H), 4.22 (t, 2H), 3.91 (s, 3H), 2.24 (m, 2H).

Step 6: To a solution 4-{3-[({(1E)-[3,5-bis(trifluoromethyl)phenyl]methylidene}amino)oxy]propoxy}-2-{[4-(trifluoromethoxy)benzoyl]amino)}benzoic acid methyl ester (0.20 g, 0.31 mmol) in 1:1 methanol:tetrahydrofuran (10 mL) was added 4N aqueous lithium hydroxide solution (0.23 mL). This mixture was heated to reflux for 10 minutes and then allowed to cool back to room temperature. The mixture was acidified to pH 1 with 1N hydrochloric acid solution and then partitioned between ethyl acetate and water. The layers were separated and the aqueous layer was extracted with one additional portion of ethyl acetate. The organics were combined, dried over anhydrous magnesium sulfate, filtered and concentrated under reduced pressure. The crude material was recrystallized one time from chloroform/hexanes and then the product was triturated with hexanes to give 4-{3-[({(1E)-[3,5-bis(trifluoromethyl)phenyl]methylidene}amino)oxy]propoxy}-2-{[4-(trifluoromethoxy)benzoyl]amino}benzoic acid (0.12 g, 61%) as a white solid. mp=184.5-185.5° C. $^1$H NMR (500 MHz, DMSO-d$_6$); δ 13.47 (bs, 1H), 12.51 (s, 1H), 8.48 (s, 1H), 8.37 (s, 1H), 8.21 (s, 2H), 8.10 (s, 1H), 8.02 (d, 2H), 7.97 (d, 1H), 7.58 (d, 2H), 6.78 (d, 1H), 4.38 (t, 2H), 4.20 (t, 2H), 2.19 (m, 2H). Mass spec (MW 638.44); (ES−) m/z 637.2. Elemental analysis; Calculated for C$_{27}$H$_{19}$F$_9$N$_2$O$_6$: C, 50.79; H, 3.00; N, 4.39. Found: C, 50.40; H, 2.68; N, 4.28.

Example 29

Synthesis of 4-[3-({[(1E)-1,1'-Biphenyl-4-ylmethylidene]amino}oxy)propoxy]-2-{[4-(trifluoromethoxy)benzoyl]amino}benzoic Acid Step 1: This compound was produced using similar methods as those used in Step 5, example 27, starting with 4-(3-bromo-propoxy)-2-(4-trifluoromethoxy-benzoylamino)-benzoic acid methyl ester (0.46 g, 0.97 mmol), biphenyl-4-carbaldehyde oxime (0.20 g, 1.01 mmol) and cesium carbonate (1.26 g, 3.86 mmol) in acetone (35 mL). The crude material was purified by flash chromatography through silica gel using diethyl ether/hexanes (0/100 gradient to 12/88) to give 4-[3-({[(1E)-1,1'-biphenyl-4-ylmethylidene]amino}oxy)propoxy]-2-{[4-(trifluoromethoxy)benzoyl]amino}benzoic acid methyl ester (0.46 g, 80%) as a white solid. $^1$H NMR (500 MHz, DMSO-d$_6$); δ 11.93 (s, 1H), 8.34 (d, 1H), 8.31 (s, 1H), 8.06 (d, 2H), 7.99 (d, 1H), 7.70-7.66 (m, 6H), 7.60 (d, 1H), 7.46 (t, 2H), 7.38 (t, 1H), 6.85 (dd, 1H), 4.31 (t, 2H), 4.23 (t, 2H), 3.87 (s, 3H), 2.18 (m, 2H).

Step 2: This compound was produced using similar methods as those used in Step 6, example 28, starting with 4-[3-({[(1E)-1,1'-biphenyl-4-ylmethylidene]amino}oxy)propoxy]-2-{[4-(trifluoromethoxy)benzoyl]amino}benzoic acid methyl ester (0.31 g, 0.52 mmol), 1:1 methanol:tetrahydrofuran (10 mL) and 4N aqueous lithium hydroxide solution (0.39 mL). The crude material was crystallized from hot chloroform (10 mL) by the addition of room temperature hexanes (100 mL), and allowing the mixture to sit for 2 hours. The product was isolated and then triturated with hexanes to give 4-[3-({[(1E)-1,1'-biphenyl-4-ylmethylidene]amino}oxy)propoxy]-2-{[4-(trifluoromethoxy)benzoyl]amino}benzoic acid (0.29 g, 95%) as a white solid. mp=194.5-195.5° C. $^1$H NMR (500 MHz, DMSO-d$_6$); δ 13.49 (bs, 1H), 12.46 (s, 1H), 8.40 (s, 1H), 8.31 (s, 1H), 8.05 (d, 2H), 8.00 (d, 1H), 7.70-7.66 (m, 6H), 7.58 (d, 2H), 7.46 (t, 2H), 7.37 (t, 1H), 6.81 (d, 1H), 4.31 (t, 2H), 4.22 (t, 2H), 2.18 (m, 2H). Mass spec (MW 578.54); (ES+) m/z 577.43 Elemental analysis; Calculated for C$_{31}$H$_{25}$F$_3$N$_2$O$_6$: C, 64.36; H, 4.36; N, 4.84. Found: C, 63.78; H, 4.18; N, 4.77.

Example 30

Synthesis of 2-{[4-(Trifluoromethoxy)benzoyl]amino}-4-{3-[({(1E)-[4-(trifluoromethyl)phenyl]methylidene}amino)oxy]propoxy}benzoic Acid Step 1: This compound was produced using similar methods as those used in Step 5, example 27, starting with 4-(3- bromo-propoxy)-2-(4-trifluoromethoxy-benzoylamino)-benzoic acid methyl ester (0.46 g, 0.97 mmol), 4-trifluoromethyl-benzaldehyde oxime (0.19 g, 1.01 mmol) and cesium carbonate (1.26 g, 3.86 mmol) in acetone (35 mL). The crude material was purified by flash chromatography through silica gel using diethyl ether/hexanes (0/100 gradient to 10/90) to give 2-{[4-(trifluoromethoxy)benzoyl]amino}-4-{3-[({(1E)-[4-(trifluoromethyl)phenyl]methylidene}amino)oxy]propoxy}benzoic acid methyl ester (0.44 g, 78%) as a white solid. $^1$H NMR (500 MHz, DMSO-$d_6$); δ 11.92 (s, 1H), 8.38 (s, 1H), 8.32 (d, 1H), 8.05 (d, 2H), 7.97 (d, 1H), 7.80-7.21 (AA'BB', 4H), 7.60 (d, 2H), 6.82 (dd, 1H), 4.34 (t, 2H), 4.21 (t, 2H), 3.87 (s, 3H), 2.18 (m, 2H).

Step 2: This compound was produced using similar methods as those used in Step 6, example 28, starting with 2-{[4-(trifluoromethoxy)benzoyl]amino}-4-{3-[({(1E)-[4-(trifluoromethyl)phenyl]methylidene}amino)oxy]propoxy}benzoic acid methyl ester (0.31 g, 0.52 mmol), 1:1 methanol:tetrahydrofuran (10 mL) and 4N aqueous lithium hydroxide solution (0.39 mL). The crude material was crystallized from hot chloroform (10 mL) by the addition of room temperature hexanes (100 mL), and allowing the mixture to sit for 2 hours. The product was isolated and then triturated with hexanes to give 4-[3-({[(1E)-1,1'-biphenyl-4-ylmethylidene]amino}oxy)propoxy]-2-{[4-(trifluoromethoxy)benzoyl]amino}benzoic acid (0.29 g, 97%) as a white solid. mp=187.5-188.5° C. $^1$H NMR (500 MHz, DMSO-$d_6$); δ 13.47 (bs, 1H), 12.45 (s, 1H), 8.38 (s,2H), 8.04 (d, 2H), 7.99 (d, 1H), 7.81-7.72 (AA'BB', 4H), 7.58 (d, 2H), 6.80 (d, 1H), 4.34 (t, 2H), 4.20 (t, 2H), 2.18 (m, 2H). Mass spec (MW 570.44); (ES−) m/z 569.39. Elemental analysis; Calculated for $C_{26}H_{20}F_6N_2O_6$: C, 54.74; H, 3.53; N, 4.91. Found: C, 54.05; H, 3.13; N, 4.80.

Example 31

Synthesis of 4-[3-({[(1E)-1,1'-Biphenyl-4-ylmethylidene]amino}oxy)propoxy]-2-{[3,5-bis(trifluoromethyl)benzoyl]amino}benzoic Acid Step 1: This compound was produced using similar methods as those used in Step 5, example 27, starting with 2-(3,5-bis-trifluoromethyl-benzoylamino)-4-(3-bromo-propoxy)-benzoic acid methyl ester (0.35 g, 0.66 mmol), biphenyl-4-carbaldehyde oxime (0.14 g, 0.70 mmol) and cesium carbonate (0.86 g, 2.65 mmol) in acetone (25 mL). The crude material was purified by flash chromatography through silica gel using diethyl ether/hexanes (0/100 gradient to 10/90) to give 4-[3-({[(1E)-1,1'-biphenyl-4-ylmethylidene]amino}oxy)propoxy]-2-{[3,5-bis(trifluoromethyl)benzoyl]amino}benzoic acid methyl ester (0.29 g, 68%) as a white solid. $^1$H NMR (500 MHz, DMSO-$d_6$); δ 11.79 (s, 1H), 8.52 (s, 2H), 8.43 (s, 1H), 8.31 (s, 1H), 8.11 (d, 1H), 7.98 (d, 1H), 7.97-7.64 (AA'BB', 4H), 7.45 (t, 2H), 7.37 (t, 1H), 6.89 (dd, 1H), 4.31 (t, 2H), 4.23 (t, 2H), 3.84 (s, 3H), 2.18 (m, 2H).

Step 2: This compound was produced using similar methods as those used in Step 6, example 28, starting with 4-[3-({[(1E)-1,1'-biphenyl-4-ylmethylidene]amino}oxy)propoxy]-2-{[3,5-bis(trifluoromethyl)benzoyl]amino}benzoic acid methyl ester (0.25 g, 0.39 mmol), 1:1 methanol:tetrahydrofuran (10 mL) and 4N aqueous lithium hydroxide solution (0.29 mL). The crude material was crystallized from hot chloroform (10 mL) by the addition of room temperature hexanes (100 mL), and allowing the mixture to sit for 2 hours. The product was isolated and then triturated with hexanes to give 4-[3-({[(1E)-1,1'-biphenyl-4-ylmethylidene]amino}oxy)propoxy]-2-{[3,5-bis(trifluoromethyl)benzoyl]amino}benzoic acid (0.054 g, 22%) as a white solid. mp=205-206° C. (dec). $^1$H NMR (500 MHz, DMSO-$d_6$); δ 13.70 (bs, 1H), 12.70 (bs, 1H), 8.51 (s, 1H), 8.43 (s, 1H), 8.32 (d, 2H), 8.00 (d, 1H), 7.67-7.64 (AA'BB', 4H), 7.45 (t, 2H), 7.37 (t, 1H), 6.84 (d, 1H), 4.31 (t, 2H), 4.22 (t, 2H), 2.18 (m, 2H). Mass spec (MW 630.54); (ES+) m/z 630.96, (ES−) m/z 629.39. Elemental analysis; Calculated for $C_{32}H_{24}F_6N_2O_5$: C, 60.96; H, 3.84; N, 4.44. Found: C, 60.10; H, 3.57; N, 4.18.

Example 32

2-{[3,5-Bis(trifluoromethyl)benzoyl]amino}-4-{3-[({(1E)-[4-(trifluoromethyl)phenyl]methylidene}amino)oxy]propoxy}benzoic Acid Step 1: This compound was produced using similar methods as those used in Step 5, example 27, starting with 2-(3,5-bis-trifluoromethyl-benzoylamino)-4-(3-bromo-propoxy)-benzoic acid methyl ester (0.35 g, 0.66 mmol), 4-trifluoromethyl-benzaldehyde oxime (0.13 g, 0.70 mmol) and cesium carbonate (0.86 g, 2.65 mmol) in acetone (25 mL). The crude material was purified by flash chromatography through silica gel using diethyl ether/hexanes (0/100 gradient to 10/90) to give 2-{[3,5-bis(trifluoromethyl)benzoyl]amino}-4-{3-[({(1E)-[4-(trifluoromethyl)phenyl]methylidene}amino)oxy]propoxy}benzoic acid methyl ester (0.33 g, 78%) as a white solid. $^1$H NMR (500 MHz, DMSO-$d_6$); δ 11.78 (s, 1H), 8.51 (s, 2H), 8.45 (s, 1H), 8.37 (s, 1H), 8.10 (d, 1H), 7.97 (d, 1H), 7.79-7.71 (AA'BB', 4H), 6.88 (dd, 1H), 4.34 (t, 2H), 4.22 (t, 2H), 3.85 (s, 3H), 2.18 (m, 2H).

Step 2: This compound was produced using similar methods as those used in Step 6, example 28, starting with 2-{[3,5-bis(trifluoromethyl)benzoyl]amino}-4-{3-[({(1E)-[4-(trifluoromethyl)phenyl]methylidene}amino)oxy]propoxy}benzoic acid methyl ester (0.22 g, 0.35 mmol), 1:1 methanol:tetrahydrofuran (10 mL) and 4N aqueous lithium hydroxide solution (0.26 mL). The crude material was triturated with hot hexanes and filtered. The product was then crystallized from hot chloroform (10 mL) by the addition of room temperature hexanes (100 mL), and allowing the mixture to sit for 2 hours to give 2-{[3,5-bis(trifluoromethyl)benzoyl]amino}-4-{3-[({(1E)-[4-(trifluoromethyl)phenyl]methylidene}amino)oxy]propoxy}benzoic acid (0.055 g, 26%) as a white solid. mp=218-219° C. (dec). $^1$H NMR (500 MHz, DMSO-$d_6$); δ 13.50 (bs, 1H), 12.72 (s, 1H), 8.49 (s, 2H), 8.44 (s, 1H), 8.38 (s, 1H), 8.31 (d, 1H), 7.99 (d, 1H), 7.80-7.71 (AA'BB', 4H), 6.82 (dd, 1H), 4.34 (t, 2H), 4.22 (t, 2H), 2.18 (m, 2H). Mass spec (MW 622.44); (ES+) m/z 623.05, (ES−) m/z 621.50. Elemental analysis; Calculated for $C_{27}H_{19}F_9N_2O_5$: C, 52.10; H, 3.08; N, 4.50. Found: C, 51.78; H, 3.03; N, 4.26.

Example 33

Synthesis of 2-Bromo-4-[({[(1E)-(4-tert-butylphenyl)methylidene]amino}oxy)methyl]benzoic Acid Step 1: To a solution of 2-bromo-4-methyl-benzoic acid (5.50 g, 25.6 mmol) in methanol (250 mL) was added concentrated sulfuric acid (1 mL). The reaction mixture was heated to reflux overnight (approximately 16 hours), allowed to cool to room temperature and then concentrated to approximately ¼ volume under reduced pressure. The residue was then partitioned between water and ethyl acetate, the layers were separated and the aqueous layer was extracted with one additional portion of ethyl acetate. The combined organics were washed one time with saturated sodium bicarbonate solution, dried over anhydrous magnesium sulfate, filtered through a plug of silica gel and concentrated under reduced pressure. 2-Bromo-4-methyl-benzoic acid methyl ester was obtained as an oil (4.95 g, 85%). To a solution of this oil (2.50 g, 10.9 mmol) in carbon tetrachloride (100 mL) was added N-bromosuccinimide (2.04 g, 11.5 mmol) and benzoylperoxide (0.106 g, 0.44 mmol). The reaction mix was heated to reflux. After approximately 1 hour, the reaction mixture became colorless. At this time the heat was removed to allow the mixture to cool to room temperature and the mixture was filtered. The filtrate was concentrated under reduced pressure. The crude mixture was purified by HPLC (40% methylene chloride in hexane) to give 2-bromo-4-bromomethyl-benzoic acid methyl ester (1.50 g, 45%) as a white powder. $^1$H NMR (400 MHz, CDCl$_3$); δ 7.75 (d, 1H), 7.66 (s, 1H), 7.35 (d, 1H), 4.39 (s, 2H), 3.90 (s, 3H).

Step 2: This compound was produced using similar methods as those used in Step 5, example 27, starting with 2-bromo-4-bromomethyl-benzoic acid methyl ester (0.40 g, 1.30 mmol), 4-tert-butyl-benzaldehyde oxime (0.24 g, 1.36 mmol) and cesium carbonate (1.69 g, 5.20 mmol) in acetone (50 mL). The crude material was purified by flash chromatography through silica gel using ethyl acetate/hexanes (0/100 gradient to 6/94) to give 2-bromo-4-[({[(1E)-(4-tert-butylphenyl)methylidene]amino}oxy)methyl]benzoic acid methyl ester (0.43 g, 83%) as a clear, colorless oil. $^1$H NMR (400 MHz, CDCl$_3$); δ 8.13 (s, 1H), 7.78 (d, 1H), 7.69 (s, 1H), 7.49 (d, 2H), 7.39-7.36 (m, 3H), 5.18 (s, 2H), 3.92 (s, 3H), 1.32 (s, 9H).

Step 3: To a solution of 2-bromo-4-[({[(1E)-(4-tert-butylphenyl)methylidene]amino}oxy)methyl]benzoic acid methyl ester (0.43 g, 1.07 mmol), in 10/5/3 tetrahydrofuran/ethanol/water (24 mL) was added 2.5 M sodium hydroxide solution (4 mL). This mixture was heated to reflux for 3 hours and then allowed to cool back to room temperature. The mixture was concentrated to approximately ¼ volume and partitioned between ethyl acetate and brine. The aqueous layer was acidified to approximately pH 1 using 1 N hydrochloric acid. The layers were then separated. The aqueous layer was extracted with one additional portion of ethyl acetate. The organics were combined, dried over anhydrous magnesium sulfate, filtered and concentrated under reduced pressure. The crude material was dissolved in hot methylene chloride and crystallized out by the addition of room temperature hexanes (60 mL), and allowing the mixture to sit for 2 hours to give 2-bromo-4-[({[(1E)-(4-tert-butylphenyl)methylidene]amino}oxy)methyl]benzoic acid (0.39 g, 94%) as a white solid. mp=162-163° C. $^1$H NMR (500 MHz, DMSO-d$_6$); δ 13.35 (bs, 1H), 8.31 (s, 1H), 7.74 (d, 1H), 7.71 (s, 1H), 7.52 (d, 2H), 7.46 (d, 1H), 7.42 (d, 2H), 5.19 (s, 2H), 1.26 (s, 9H). Mass spec (MW 390.28); (ES+) m/z 390.0, (ES−) m/z 388.3. Elemental analysis; Calculated for C$_{19}$H$_{20}$BrNO$_3$: C, 58.47; H, 5.17; N, 3.59. Found: C, 57.99; H, 5.03; N, 3.41.

Example 34

Synthesis of 4-[3-({[(1E)-(4-tert-Butylphenyl)methylidene]amino}oxy)propoxy]-2-(2-naphthoylamino)benzoic Acid Step 1: To a stirred suspension of 4-amino-2-nitrobenzoic acid (9.895 g, 54.326 mmol) in water (17 ml) was added concentrated H$_2$SO$_4$ (12 ml). The resulting homogenous solution was cooled in an ice bath and additional water (10 ml) added to aid stirring. Crushed ice (50 ml) was added followed by the drop-wise addition of NaNO$_2$ (4.124 g, 59.759 mmol) in water (9 ml). The temperature was kept below 5° C. during the addition and then stirred for 1.25 h at 0° C. The reaction mixture was quenched by adding urea (6 g), stirred for 10 minutes at 0° C., filtered and the filtrate added drop-wise into a boiling solution of concentrated H$_2$SO$_4$ (39 ml) and water (27 ml). After the addition, the entire mixture was refluxed for 3 hours then cooled. The reaction mixture was extracted with ethyl acetate (6×50 ml) and the combined organics washed with brine, filtered and concentrated to a small volume which was then purified by flash chromatography on silica. The first column was eluted with ethyl acetate and 20% MeOH/EtOAc. The second column was eluted with 10% MeOH/CHCl$_3$ and the third column was eluted with 60% EtOAc/Hexane. The purification process gave 4-hydroxy-2-nitrobenzoic acid (5.331 g, 29.112 mmol, 54%) as an orange solid, dec. 232-236° C. $^1$H NMR (DMSO-d$_6$) δ 7.05 (dd, 1H), 7.15 (s, 1H), 7.78 (d, 1H) 11.10 (s, 1H), 13.38 (s, 1H); mass spectrum [ES(−)], m/z 182 (M−H)−.

Step 2: To a solution of 4-hydroxy-2-nitrobenzoic acid (5.331 g, 29.112 mmol) in methanol (115 ml) was added concentrated H$_2$SO$_4$ (2.88 ml) and the mixture refluxed for 18 hours then cooled and concentrated. The residue was partitioned between EtOAc (200 ml) and water (50 ml). The layers were shaken, separated, and the aqueous layer washed with EtOAc (3×30 ml). The combined organics were washed with water (3×30 ml), brine (2×30 ml), dried over Na$_2$SO$_4$, filtered, concentrated and dried to give a yellow solid (5.559 g). The solid was purified by flash chromatography on silica, eluting with hexane and 20% EtOAc/hexane. The appropriate fractions were collected, filtered, concentrated, and dried to give 4-hydroxy-2-nitrobenzoic acid methyl ester (5.00 g, 25.36 mmol, 87%) as a solid, mp 161-166° C. $^1$H NMR (DMSO-d$_6$) δ 3.77 (s, 3H), 7.10 (dd, 1H), 7.23 (s, 1H), 7.78 (d, 1H), 11.20 (s, 1H); mass spectrum [ES(−)], m/z 196 (M−H)−.

Step 3: To a stirred solution of 4-hydroxy-2-nitrobenzoic acid methyl ester (4.410 g, 22.369 mmol) in methanol (80 ml) under nitrogen at room temperature was added ammonium formate (5.642 g, 89.475 mmol) and 5% Pd/C (450 mg). After 5 hours the reaction mixture was filtered through celite and rinsed. The filtrate was concentrated and the residue partitioned between EtOAc (150 ml) and water (40 ml). The layers were shaken, separated and the organic layer washed with water (3×30 ml), brine (2×30 ml), dried over Na$_2$SO$_4$, filtered, concentrated and dried to give 2-amino-4-hydroxybenzoic acid methyl ester (3.593 g, 21.494 mmol, 96%) as an off-white solid, dec. 113-118° C. $^1$H NMR (DMSO-d$_6$) δ 3.70 (s, 3H), 5.98 (dd, 1H), 6.10 (s, 1H), 6.59 (s, 1H), 7.54 (d, 1H), 9.81 (s, 1H); mass spectrum [ES(−)], m/z 166 (M−H)−.

Step 4: To a stirred solution of 2-amino-4-hydroxy-benzoic acid methyl ester (0.334 g, 2 mmol) in acetone (20 ml) with NaHCO$_3$ (0.202 g, 2.4 mmol) under nitrogen was added 2-naphthoylchloride (0.381 g, 2 mmol). After 18 h, the reaction mixture was concentrated and the residue partitioned between EtOAc (300 ml) and water (30 ml). The layers were shaken, separated and the organic layer washed with water (3×40 ml), brine (2×30 ml), dried over Na$_2$SO$_4$, filtered, concentrated and dried to give a solid (570 mg). The solid was recrystallized from acetonitrile to give 4-hydroxy-2-(naphthoylamino)-benzoic acid methyl ester (0.425 g, 1.323 mmol, 66%) as an off-white solid, mp 246-248° C. $^1$H NMR (DMSO-d$_6$) δ 3.90 (s, 3H), 6.61 (d, 1H), 7.60-7.70 (m, 2H), 7.95 (d, 1H), 7.99-8.08 (m, 2H), 8.14 (d, 2H), 8.30 (s, 1H), 8.58 (s, 1H), 10.65 (s, 1H), 12.12 (s, 1H); mass spectrum [ES(−)], m/z 320 (M−H)−.

Step 5: To a stirred solution of 2-(2-naphthoylamino)-4-hydroxybenzoic acid methyl ester (0.425 g, 1.323 mmol) in DMF/acetone (15 ml each) was added K$_2$CO$_3$ (0.914 g, 6.613 mmol) and 1,3-dibromoproprane (1.082 g, 5.358 mmol). The reaction mixture was refluxed for 4 h. After cooling, the reaction mixture was concentrated and the residue partitioned between EtOAc (100 ml) and 1:1 water/brine (50 ml). The layers were shaken, separated and the organic layer washed with brine (1×15 ml), dried over Na$_2$SO$_4$, filtered, concentrated and dried to give a yellow residue (513 mg). This residue was purified by flash chromatography (silica, 45 g), eluting with hexane and 5% EtOAc/hexane. The appropriate fractions were collected, filtered, concentrated and dried to give 4-(3-bromopropoxy)-2-(2-naphthoylamino)-benzoic acid methyl ester (350 mg, 0.791 mmol, 79%) as a colorless, viscous gum. $^1$H NMR (DMSO-d$_6$) δ 2.25-2.39 (m, 2H), 3.70 (t, 2H), 3.90 (s, 3H), 4.21 (t, 2H), 6.85 (d, 1H), 7.60-7.75 (m, 2H), 7.95-8.20 (m, 5H), 8.40 (s, 1H), 8.58 (s, 1H), 12.08 (s, 1H); mass spectrum [ES(−)], m/z 440 (M−H)$^-$.

Step 6: To a stirred solution of 4-(3-bromopropoxy)-2-(2-naphthoylamino)-benzoic acid methyl ester (0.350 g, 0.791 mmol) in acetone (25 ml) was added cesium carbonate (0.541 g, 1.661 mmol) and 4-tert-butyl-benzaldehyde oxime (0.154 g, 0.870 mmol). The mixture was refluxed. When the reaction was done, heating was stopped and the mixture concentrated. The residue was partitioned between EtOAc (70 ml) and water (15 ml). The layers were shaken, separated and the organic layer washed with water (2×15 ml), brine (2×15 ml), dried over Na$_2$SO$_4$, filtered and concentrated to give a residue (435 mg). This residue was purified by flash chromatography (alumina, Brockman activity I). The column was eluted using a chloroform/hexane gradient (0 to 40%). The residue obtained from the column was further purified by preparatory HPLC to give 4-[3-({[(1E)-(4-tert-butylphenyl)methylidene]amino}oxy)propoxy]-2-(2-naphthoylamino)benzoic acid methyl ester (0.294 g, 0.546 mmol, 69%) as a pale yellow, viscous oil. $^1$H NMR (DMSO-d$_6$) δ 1.25 (s, 9H), 2.15-2.25 (m, 2H), 3.93 (s, 3H), 4.25 (t, 2H), 4.32 (t, 2H), 6.86 (d, 1H), 7.42 (d, 2H), 7.53 (d, 2H), 7.65-7.74 (m, 2H), 8.00-8.08 (m, 3H), 8.12-8.18 (m, 2H), 8.24 (s, 1H), 8.44 (s, 1H), 8.60 (s, 1H), 12.10 (s, 1H); mass spectrum [ES(+)], m/z 539 (M+H)$^+$.

Step 7: To a solution of 4-[3-({[(1E)-(4-tert-butylphenyl)methylidene]amino}oxy)propoxy]-2-(2-naphthoylamino)benzoic acid methyl ester (0.294 g, 0.546 mmol) in THF (6 ml) and MeOH (4 ml) was added 1N KOH (1.1 ml). The reaction mixture was stirred under nitrogen at room temperature for 23 h and then concentrated. The residue was diluted with water (20 ml), acidified with 2N HCL (1.1 ml) and extracted with EtOAc (1×80 ml). The organic layer was washed with 1N HCl (2×20 ml), water (3×15 ml), brine (2×15 ml), dried over Na$_2$SO$_4$, filtered and concentrated to give a solid (0.251 g). The solid was recrystallized from MeCN to give 4-[3-({[(1E)-(4-tert-butylphenyl)methylidene]amino}oxy)propoxy]-2-(2-naphthoylamino)benzoic acid (0.135 g, 0.257 mmol, 47%) as a white solid, mp 156-158° C. $^1$H NMR (DMSO-d$_6$) δ 6.54 (dd, J=2.4, 11.1 Hz, 1H), 6.87 (d, J=15.6 Hz, 1H), 7.39 (t, J=7.3 Hz, 1H), 7.48 (t, J=7.8 Hz, 1H), 7.66 (d, J=15.6 Hz, 1H), 7.83 (d, J=8.2 Hz, 1H), 7.87 (d, J=8.7 Hz, 1H), 7.87 (d, J=8.2 Hz, 2H), 8.22 (d, J=2.4 Hz, 1H), 10.43 (s, 1H), 11.65 (s, 1H), 13.10 (s, 1H); IR (solid) 2960, 1660, 1610, 1580, 1540, 1420, and 1240 cm$^{-1}$; mass spectrum [ES(−)], m/z 523.5 (M−H)$^-$; Anal. Calcd. for C$_{32}$H$_{32}$N$_2$O$_5$: C, 73.26; H, 6.15; N, 5.34, Found: C, 73.25; H, 6.03; N, 5.02.

Example 35

Synthesis of 2-{[(2E)-3-(1,1'-Biphenyl-4-yl)prop-2-enoyl]amino}-4-[3-({[(1E)-(4-tert-butylphenyl)methylidene]amino}oxy)propoxy]-benzoic Acid Step 1: To a stirred solution of 4-biphenylcarboxaldehyde (7.289 g, 40 mmol) in MeCN (80 ml) under nitrogen at room temperature was added methyl(triphenylphosphoranylidene)acetate (16.049 g, 48 mmol). After 18 h the reaction mixture was concentrated and the residue purified by flash chromatography, eluting with 10% EtOAc/hexane. The appropriate fractions were collected, filtered, concentrated and dried to give 3-biphenyl-4-yl-acrylic acid methyl ester (9.384 g, 39.38 mmol, 98%) as a pale yellow solid, mp 144-147° C. $^1$H NMR (DMSO-d$_6$) δ 3.75 (s, 3H), 6.70 (d, 1H), 7.35-7.53 (m, 3H), 7.65-7.78 (m, 5H), 7.82 (d, 2H).

Step 2: To a suspension of 3-biphenyl-4-yl-acrylic acid methyl ester (9.384 g, 39.38 mmol) in THF (120 ml) and MeOH (80 ml) was added 1N KOH (79 ml) and the mixture refluxed. After 3 h, heating was stopped. The reaction mixture was concentrated to about 50 ml, diluted with water (200 ml) and acidified with 2N HCl (80 ml). EtOAc (1000 ml) was added and the whole mixture heated to boiling to dissolve all solids. After cooling, the layers were separated and the organic layer washed with 1N HCl (2×70 ml), water (3×70 ml), brine (2×50 ml), dried over Na$_2$SO$_4$, filtered, concentrated and dried to give 3-biphenyl-4-yl-acrylic acid (7.393 g, 32.966 mmol, 84%) as a white solid, dec. 223-226° C. $^1$H NMR (DMSO-d$_6$) δ 6.58 (d, 1H), 7.37-7.53 (m, 3H), 7.62 (d, 1H), 7.70-7.84 (m, 6H), 12.40 (s, 1H); mass spectrum [ES(−)], m/z 223 (M−H)$^-$.

Step 3: A mixture of 3-biphenyl-4-yl-acrylic acid (0.449 g, 2.004 mmol) in SOCl$_2$ (5 ml) was refluxed for 2 h. After cooling, the solvent was removed. The residue was dissolved in acetone and added into a stirred solution of 4-hydroxy-2-(naphthoylamino)-benzoic acid methyl ester (0.335 g, 2.004 mmol) in acetone (10 ml) with NaHCO$_3$ (0.202 g, 2.405 mmol). After 18 h, the reaction mixture was concentrated. The residue was triturated with water, filtered and the solids rinsed with ether and dried to give 2-{[(2E)-3-(1,1'-biphenyl-4-yl)prop-2-enoyl]amino}-4-hydroxybenzoic acid methyl ester (0.593 g, 1.588 mmol, 79%) as an off-white solid, mp 292-296° C. $^1$H NMR (DMSO-d$_6$) δ 3.88 (s, 3H), 6.57 (dd, 1H), 6.95 (d, 1H), 7.37-7.54 (m, 3H), 7.67 (d, 1H), 7.70-7.80 (m, 4H), 7.80-7.90 (m, 3H), 8.20 (dd, 1H), 10.55 (s, 1H), 11.20 (s, 1H); mass spectrum [ES(−)], m/z 372 (M−H)$^-$.

Step 4: To a stirred solution of 2-{[(2E)-3-(1,1'-biphenyl-4-yl)prop-2-enoyl]amino}-4-hydroxybenzoic acid methyl ester (0.373 g, 1 mmol) in acetone/DMF (15 ml each) was added K$_2$CO$_3$ (0.691 g, 5 mmol) and 1,3-dibromopropane (0.818 g, 4.05 mmol). The reaction mixture was refluxed for 1 h then cooled and concentrated. The residue was partitioned between EtOAc (150 ml) and water (100 ml) and the whole was filtered to remove insolubles. The layers of the filtrate were separated and the organic layer washed with brine (2×30 ml), dried over Na$_2$SO$_4$, filtered, concentrated and dried to give a white solid (0.380 g). This solid was recrystallized from MeCN to give 2-{[(2E)-3-(1,1'-biphenyl-4-yl)prop-2-enoyl]amino}-4-(3-bromopropoxy)benzoic acid methyl ester (0.301 g, 0.609 mmol, 61%) as a white solid, mp 142-145° C. $^1$H NMR (DMSO-d$_6$) δ 2.22-2.37 (m, 2H), 3.70 (t, 2H), 3.88 (s, 3H), 4.18 (t, 2H), 6.80 (dd, 1H), 6.98 (d, 1H), 7.38-7.55 (m, 3H), 7.63-7.80 (m, 5H), 7.85 (d, 2H), 7.95 (d, 1H), 8.30 (dd, 1H), 11.19 (s, 1H); mass spectrum [ES(−)], m/z 492 (M−H)$^-$.

Step 5: The desired product was prepared using a procedure similar to Step 6 of example 34. Thus, 2-{[(2E)-3-(1,1'-biphenyl-4-yl)prop-2-enoyl]amino}-4-(3-bromopropoxy)benzoic acid methyl ester (0.299 g, 0.605 mmol) was reacted with cesium carbonate (0.414 g, 1.271 mmol) and 4-tert-butyl-benzaldehyde oxime (0.118 g, 0.665 mmol) in acetone (30 ml) to give 2-{[(2E)-3-(1,1'-biphenyl-4-yl)prop-2-enoyl]amino}-4-[3-({[(1E)-(4-tert-butylphenyl)methylidene]amino}oxy)propoxy]benzoic acid methyl ester (0.148 g, 0.251 mmol, 41%) as a pale yellow solid, mp 120-122° C. $^1$H NMR (DMSO-d$_6$) δ 1.25 (s, 9H), 2.10-2.22 (m, 2H), 3.85 (s, 3H), 4.18 (t, 2H), 4.26 (t, 2H), 6.80 (dd, 1H), 6.95 (d, 1H), 7.37-7.54 (m, 7H), 7.62-7.78 (m, 5H), 7.83 (d, 2H), 7.97 (d, 1H), 8.22 (s, 1H), 8.30 (dd, 1H), 11.16 (s, 1H); mass spectrum [ES(−)], m/z 589 (M−H)⁻.

Step 6: The desired product was prepared using a procedure similar to Step 7 of example 34. Thus, 2-{[(2E)-3-(1,1'-biphenyl-4-yl)prop-2-enoyl]amino}4-[3-({[(1E)-(4-tert-butylphenyl)methylidene]amino}oxy)propoxy]benzoic acid methyl ester (0.148 g, 0.251 mmol) was reacted with 1N KOH (0.50 ml) in THF/MeOH (6 ml/4 ml) to give 2-{[(2E)-3-(1,1'-biphenyl-4-yl)prop-2-enoyl]amino}-4-[3-({[(1E)-(4-tert-butylphenyl)methylidene]amino}oxy)propoxy]benzoic acid (0.099 g, 0.172 mmol, 68%) as a white solid, mp 169-171° C. ¹H NMR (DMSO-d$_6$) δ 1.26 (s, 9H), 2.13-2.17 (m, 2H), 4.18 (t, J=6.4 Hz, 2H), 4.27 (t, J=6.3 Hz, 2H), 6.75 (dd, J=2.6, 8.9 Hz, 1H), 6.89 (d, J=15.6 Hz, 1H), 7.38-7.43 (m, 3H), 7.46-7.54 (m, 4H), 7.67 (d, J=15.6 Hz, 1H), 7.70-7.76 (m, 4H), 7.83 (d, J=8.2 Hz, 2H), 7.96 (d, J=8.9 Hz, 1H), 8.23 (s, 1H), 8.38 (d, J=2.4 Hz, 1H), 11.75 (s, 1H), 13.3 (s, 1H); IR (solid) 2960, 1680, 1610, 1580, 1540 and 1200 cm⁻¹; [ES(−)], m/z 575 (M−H)⁻; Anal. Calcd. for C$_{36}$H$_{36}$N$_2$O$_5$: C, 74.98; H, 6.29; N, 4.86, Found: C, 74.57; H, 6.32; N, 4.89.

Example 36

Synthesis of 2-[(1,1'-Biphenyl-4-ylcarbonyl)amino]-4-[3-({[(1E)-(4-tert-butylphenyl)methylidene]amino}oxy)propoxy]benzoic Acid Step 1: The desired product was prepared using a procedure similar to Step 4 of example 34. Thus, 2-amino-4-hydroxy-benzoic acid methyl ester (0.334 g, 2 mmol) was reacted with NaHCO$_3$ (0.202 g, 2.4 mmol) and 4-biphenylcarbonyl chloride (0.433 g, 2 mmol) in acetone (20 ml) to give 2-[(biphenyl-4-carbonyl)-amino]-4-hydroxy-benzoic acid methyl ester (0.423 g, 1.218 mmol, 61%) as an off-white solid, mp 273-276° C. ¹H NMR (DMSO-d$_6$) δ 3.88 (s, 3H), 6.60 (dd, 1H), 7.40-7.53 (m, 3H), 7.75 (d, 2H), 7.90-7.95 (m, 3H), 8.04 (d, 2H), 8.30 (s, 1H), 10.64 (s, 1H), 12.08 (s, 1H); mass spectrum [ES(−)], m/z 346 (M−H)⁻.

Step 2: The desired product was prepared using a procedure similar to Step 5 of example 34. Thus, 2-[(biphenyl-4-carbonyl)-amino]-4-hydroxy-benzoic acid methyl ester (0.423 g, 1.218 mmol) was reacted with K$_2$CO$_3$ (0.842 g, 6.090 mmol) and 1,3-dibromopropane (0.996 g, 4.933 mol) in acetone/DMF (15 ml each) to give 2-[(Biphenyl-4-carbonyl)-amino]-4-(3-bromo-propoxy)-benzoic acid methyl ester (0.325 g, 0.694 mmol, 57%) as a white solid, mp 108-110° C. ¹H NMR (DMSO-d$_6$) δ 2.23-2.30 (m, 2H), 3.65 (t, 2H), 3.85 (s, 3H), 4.17 (t, 2H), 6.79 (d, 1H), 7.38-7.50 (m, 3H), 7.74 (d, 2H), 7.90 (d, 2H), 7.95-8.02 (m, 3H), 8.38 (s, 1H), 11.99 (s, 1H); mass spectrum [ES(+)], m/z 468 (M+H)⁺.

Step 3: The desired product was prepared using a procedure similar to Step 6 of example 34. Thus, 2-[(biphenyl-4-carbonyl)-amino]-4-(3-bromo-propoxy)-benzoic acid methyl ester (0.325 g, 0.694 mmol) was reacted with Cs$_2$Co$_3$ (0.475 g, 1.457 mmol) and 4-tert-Butyl-benzaldehyde oxime (0.135 g, 0.763 mmol) in acetone (30 ml) to give 2-[(1,1'-biphenyl-4-ylcarbonyl)amino]-4-[3-({[(1E)-(4-tert-butylphenyl)methylidene]amino}oxy)propoxy]benzoic acid methyl ester (0.258 g, 0.457 mmol, 66%) as a viscous yellow oil. ¹H NMR (DMSO-d$_6$) δ 1.20 (s, 9H), 2.05-2.18 (m, 2H), 3.85 (s, 3H), 4.18 (t, 2H), 4.23 (t, 2H), 6.79 (d, 1H), 7.32-7.50 (m, 7H), 7.73 (d, 2H), 7.85 (d, 2H), 7.95-8.02 (m, 3H), 8.18 (s, 1H), 8.39 (s, 1H), 11.98 (s, 1H), mass spectrum [ES(+)], m/z 565 (M+H)⁺.

Step 4: The desired product was prepared using a procedure similar to Step 7 of example 34. Thus, 2-[(1,1'-biphenyl-4-ylcarbonyl)amino]4-[3-({[(1E)-(4-tert-butylphenyl)methylidene]amino}oxy)propoxy]benzoic acid methyl ester (0.253 g, 0.448 mmol) was reacted with 1N KOH (0.90 ml) in THF/MeOH (6 ml/4 ml) to give 2-[(1,1'-biphenyl-4-ylcarbonyl)amino]-4-[3-({[(1E)-(4-tert-butylphenyl)methylidene]amino}oxy)propoxy]benzoic acid (0.157 g, 0.285 mol, 64%) as a white solid, mp 155-158.5° C. ¹H NMR (DMSO-d$_6$) δ 1.25 (s, 9H), 2.14-2.18 (m, 2H), 4.21 (t, J=6.3 Hz, 2H), 4.28 (t, J=6.3 Hz, 2H), 6.78 (dd, J=2.4, 8.9 Hz, 1H), 7.38-7.45 (m, 3H), 7.49-7.54 (m, 4H), 7.77 (d, J=8.3 Hz, 2H), 7.90 (d, J=8.2 Hz, 2H), 7.98-8.06 (m, 3H), 8.22 (s, 1H), 8.46 (d, 2.4 Hz, 1H) 12.60 (s, 1H); IR (solid) 3120, 2960, 1620, 1580, 1220 and 1140 cm⁻¹; [ES(+)], m/z 551 (M+H)⁺; Anal. Calcd. for C$_{34}$H$_{34}$N$_2$O$_5$: C, 74.16; H, 6.22; N, 5.09, Found: C, 73.94; H, 5.91; N, 4.93.

Example 37

Screening for PAI-1 inhibition. Test compounds are dissolved in DMSO at a final concentration of 10 mM, then diluted 100×in physiologic buffer. The inhibitory assay is initiated by the addition of the test compound (1-100 μM final concentration, maximum DMSO concentration of 0.2%) in a pH 6.6 buffer containing 140 nM recombinant human plasminogen activator inhibitor-1 (PAI-1; Molecular Innovations, Royal Oak, Mich.). Following a 1 hour incubation at room temperature, 70 nM of recombinant human tissue plasminogen activator (tPA) is added, and the combination of the test compound, PAI-1 and tPA is incubated for an additional 30 minutes. Following the second incubation, Spectrozyme-tPA (American Diagnostica, Greenwich, Conn.), a chromogenic substrate for tPA, is added and absorbance read at 405 nm at 0 and 60 minutes. Relative PAI-1 inhibition is equal to the residual tPA activity in the presence of the test compounds and PAI-1. Control treatments include the complete inhibition of tPA by PAI-1 at the molar ratio employed (2:1), and the absence of any effect of the test compound on tPA alone.

Example 38

Assay for determining the IC$_{50}$ of inhibition of PAI-1. This assay is based upon the non-SDS dissociable interaction between tPA and active PAI-1. Assay plates are initially coated with human tPA (10 μg/ml). Test compounds are dissolved in DMSO at 10 mM, then diluted with physiologic buffer (pH 7.5) to a final concentration of 1-50 μM. The test compounds are incubated with human PAI-1 (50 ng/ml) for 15 minutes at room temperature. The tPA-coated plate is washed with a solution of 0.05% Tween 20 and 0.1% BSA, then the plate is blocked with a solution of 3% BSA. An aliquot of the test compound/PAI-1 solution is then added to the tPA-coated plate, incubated at room temperature for 1 hour, and washed. Active PAI-1 bound to the plate is assessed by adding an aliquot of a 1:1000 dilution of the 33B8 monoclonal antibody against human PAI-1, and incubating the plate at room temperature for 1 hour (Molecular Innovations, Royal Oak, Mich.). The plate is again washed, and a solution of goat anti-mouse IgG-alkaline phosphatase conjugate is added at a 1:50,000 dilution in goat serum. The plate is incubated 30 minutes at room temperature, washed, and a solution of alkaline phosphatase substrate is added. The plate is incubated 45 minutes at room temperature, and color development is determined at OD405 nm. The quantitation of active PAI-1 bound to tPA at varying concentrations of the test compound is used to determine the IC$_{50}$. Results are analyzed using a logarithmic best-fit equation. The assay sensitivity is 5 ng/ml of human PAI-1 as determined from a standard curve ranging from 0-100 ng/ml.

Representative compounds of the present invention inhibited Plasminogen Activator Inhibitor-1 as summarized in Table I.

TABLE 1

| Compound No. | Compound Name | IC$_{50}$ (µM) | % Inhibition @ 25 µM |
|---|---|---|---|
| 1 | (4-{3-[1-(4-tert-butyl-phenyl)-ethylideneaminooxy]-propoxy}-phenyl)-acetic acid | — | 39 |
| 2 | {4-[1-(4-tert-butyl-phenyl)-ethylideneaminooxymethyl]-phenyl}-acetic acid | — | 30 |
| 3 | [4-(4-tert-butyl-benzylideneaminooxymethyl)-phenyl]-acetic acid | — | 19 |
| 4 | {4-[3-(4-tert-butyl-benzylideneaminooxy)-propoxy]-phenyl}-acetic acid | 34.22 | — |
| 5 | 4-{2-[({(E)-1-[4-(tert-butyl)-phenyl]-ethylidene}amino)oxy]-ethoxy}-2-hydroxy-benzoic acid | 20.2[b] | — |
| 6 | 2-{[4-(tert-Butyl)benzoyl]oxy}-4-[2-({1-phenylethylidene]amino}oxy)ethoxy]benzoic acid | 16.70 | — |
| 7 | 4-{2-[({[4-(tert-butyl)phenyl]methylidene}amino)oxy)-ethoxy}-2-hydroxybenzoic acid | — | 33 |
| 8 | 4-{2-[({(E)-4-(tert-butyl)phenyl]methylidene}amino)oxy]ethoxy}-2-{[4-(trifluoromethyl)benzoyl]oxy}benzoic acid | — | 1 |
| 9 | 4-{2-[({(E)-4-(tert-butyl)phenyl]methylidene}amino)oxy]ethoxy}-2-[(4-methoxybenzoyl)oxy]benzoic acid | 25.6[b] | — |
| 10 | 2-{[4-(tert-butyl)benzoyl]oxy}-4-{2-[({(E)-[4-(tert-butyl)phenyl]methylidene}amino)oxy]ethoxy}benzoic acid | 17.82 | — |
| 11 | 2-(benzoyloxy)-4-{2-[({(E)-[4-(tert-butyl)phenyl]methylidene}amino)oxy]ethoxy}benzoic acid | 8.4[b] | — |
| 12 | 4-{2-[({(E)-1-[4-(tert-butyl)phenyl]ethylidene}amino)oxy]-ethoxy}-3-chloro-benzoic acid | 11.2[b] | — |
| 13 | 4-{2-[({(E)-1-[4-(tert-butyl)phenyl]ethylidene}amino)oxy]-ethoxy}-2-chloro-benzoic acid | — | 34 |
| 14 | 4-{2-[({[4-(tert-Butyl)phenyl]methylidene}amino)oxy]ethoxy}-2-{[4-(trifluoromethyl)benzyl]oxy}benzoic acid | — | 28 |
| 15 | 2-[([1,1'-biphenyl]-4-ylcarbonyl)oxy]-4-[2-({[(E)-1-phenylethylidene]amino}oxy)ethoxy]benzoic acid | 18.86 | — |
| 16 | 3-(4-{3-[({(E)-[4-(tert-butyl)phenyl]methylidene}amino)oxy]propoxy}phenyl)propanoic acid | — | 42 |
| 17 | 4-(tert-butyl)benzaldehyde O-{3-[4-(1H-tetraazol-5-ylmethyl)-phenoxy]-propyl}oxime | — | 35 |
| 18 | 2-{[4-(tert-butyl)benzoyl]amino}-4-{3-[({(E)-[4-(tert-butyl)phenyl]methylidene}amino)oxy]propoxy}benzoic acid | 18.5[b] | — |
| 19 | 4-{3-[({(E)-[3,5-bis(trifluoromethyl)phenyl]methylidene}amino)oxy]propoxy}-2-hydroxybenzoic acid | 4.14 | — |
| 20 | 4-[3-({[(1E)-1,1'-Biphenyl-4-ylmethylidene]amino}oxy)propoxy]-2-{[4-(trifluoromethyl)benzoyl]amino}benzoic acid | 25.7[b] | — |
| 21 | 4-[3-({[(1E)-1-(4-tert-Butylphenyl)propylidene]amino}oxy)propoxy]-2-{[4-(trifluoromethyl)benzoyl]amino}benzoic acid | 16.28 | — |
| 22 | 2-{[4-(trifluoromethyl)benzoyl]amino}-4-{3-[({(1E)-[4-(trifluoromethyl)phenyl]methylidene}amino)oxy]propoxy}benzoic acid | 4.14 | — |
| 23 | 4-[3-({[(1E)-1-Phenylethylidene]amino}oxy)propoxy]-2-{[4-(trifluoromethyl)benzoyl]amino}benzoic acid | — | 26 |
| 24 | 4-[3-({[(1E)-(4-tert-Butylphenyl)methylidene]amino}oxy)propoxy]-2-{[2-(trifluoromethyl)benzoyl]amino}benzoic acid | 17.52 | — |

TABLE 1-continued

| Compound No. | Compound Name | IC$_{50}$ (μM) | % Inhibition @ 25 μM |
|---|---|---|---|
| 25 | 2-{[2-(Trifluoromethyl)benzoyl]amino}-4-{3-[({(1E)-[4-(trifluoromethyl)phenyl]methylidene}amino)oxy]propoxy}benzoic acid | 26.79 | — |
| 26 | 4-[3-({[(1E)-1,1'-biphenyl-4-ylmethylidene]amino}oxy)propoxy]-2-{[2-(trifluoromethyl)benzoyl]amino}benzoic acid | — | 24 |
| 27 | 2-{[3,5-bis(trifluoromethyl)benzoyl]amino}-4-[3-({[(1E)-(4-tert-butylphenyl)methylidene]amino}oxy)propoxy]benzoic acid | 15.69 | — |
| 28 | 4-{3-[({(1E)-[3,5-bis(trifluoromethyl)phenyl]methylidene}amino)oxy]propoxy}-2-{[4-(trifluoromethoxy)benzoyl]amino}benzoic acid | — | 51 |
| 29 | 4-[3-({[(1E)-1,1'-biphenyl-4-ylmethylidene]amino}oxy)propoxy]-2-{[4-(trifluoromethoxy)benzoyl]amino}benzoic acid | — | 70 |
| 30 | 2-{[4-(trifluoromethoxy)benzoyl]amino}-4-{3-[({(1E)-[4-(trifluoromethyl)phenyl]methylidene}amino)oxy]propoxy}benzoic acid | 15.95 | — |
| 31 | 4-[3-({[(1E)-1,1'-biphenyl-4-ylmethylidene]amino}oxy)propoxy]-2-{[3,5-bis(trifluoromethyl)benzoyl]amino}benzoic acid | 19.57 | — |
| 32 | 2-{[3,5-bis(trifluoromethyl)benzoyl]amino}-4-{3-[({(1E)-[4-(trifluoromethyl)phenyl]methylidene}amino)oxy]propoxy}benzoic acid | 15.75 | — |
| 33 | 2-bromo-4-[({[(1E)-(4-tert-butylphenyl)methylidene]amino}oxy)methyl]benzoic acid | 13.84 | — |
| 34 | 4-[3-({[(1E)-(4-tert-butylphenyl)methylidene]amino}oxy)propoxy]-2-(2-naphthoylamino)benzoic acid | — | 14 |
| 35 | 2-{[(2E)-3-(1,1'-biphenyl-4-yl)prop-2-enoyl]amino}-4-[3-({[(1E)-(4-tert-butylphenyl)methylidene]amino}oxy)propoxy]benzoic acid | — | 16 |
| 36 | 2-[(1,1'-biphenyl-4-ylcarbonyl)amino]-4-[3-({[(1E)-(4-tert-butylphenyl)methylidene]amino}oxy)propoxy]benzoic acid | — | 23 |

$^b$The IC$_{50}$ was determined by a modification of the Primary Screen for PAI-1 Inhibition Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

All publications and patent documents cited above are hereby incorporated by reference in their entirety for all purposes to the same extent as if each were so individually denoted.

What is claimed:

1. A compound of the formula:

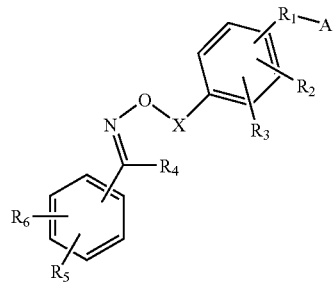

or a pharmaceutically acceptable salt or ester form thereof wherein:

$R_1$ is a direct bond to A, unsubstituted straight-chain $C_1$-$C_4$ alkylene, or —O—$C_1$-$C_4$ alkylene;

$R_2$ and $R_3$ are, independently hydrogen, halogen, $C_1$-$C_4$ alkyl, $C_1$-$C_3$ perfluoroalkyl, —O—$C_1$-$C_3$ perfluoroalkyl, $C_1$-$C_3$ alkoxy, —OH, —NH$_2$, —NO$_2$, —O(CH$_2$)$_p$-aryl, —O(CH$_2$)$_p$-heteroaryl, aryl, heteroaryl, —NH(CH$_2$)$_p$-aryl, —NH(CH$_2$)$_p$-heteroaryl, —NH(CO)-aryl, —NH(CO)-heteroaryl, —O(CO)-aryl, —O(CO)-heteroaryl, —NH(CO)—CH=CH-aryl, or —NH(CO)—CH=CH-heteroaryl;

p is an integer from 0-6;

$R_4$ is hydrogen, $C_1$-$C_8$ alkyl, or $C_3$-$C_6$ cycloalkyl;

A is COOH or an acid mimic;

X is $C_1$-$C_8$ alkylene, $C_3$-$C_6$ cycloalkylene, —(CH$_2$)$_m$O—, or —(CH$_2$)$_m$NH—;

m is an integer from 1-6;

$R_5$ and $R_6$, are, independently, hydrogen, halogen, $C_1$-$C_6$ alkyl, $C_1$-$C_6$ perfluoroalkyl, —O—$C_1$-$C_6$ perfluoroalkyl, $C_1$-$C_6$ alkoxy, —OH, —$NH_2$, —$NO_2$, —O(C$H_2$)$_n$-aryl, —O(C$H_2$)$_n$-heteroaryl, aryl, or heteroaryl; and n is an integer from 0-6, wherein $C_1$-$C_4$ alkylene, —O—$C_1$-$C_4$ alkylene, alkyl, aryl and heteroaryl are each optionally substituted by one or more substituents.

2. A compound according to claim 1 wherein $R_1$ is a direct bond, —$CH_2$—, or —$CH_2$—$CH_2$—, or a pharmaceutically acceptable salt or ester form thereof.

3. A compound according to claim 1 wherein the rings of the aryl and heteroaryl groups are optionally substituted with 1 to 3 groups selected from halogen, $C_1$-$C_6$ alkyl, $C_1$-$C_6$ perfluoroalkyl, —O—$C_1$-$C_6$ perfluoroalkyl, $C_1$-$C_6$ alkoxy, —OH, —$NH_2$, —$NO_2$, —CN, aryl, —O-aryl, —NH-aryl, —NH—CO-alkyl, or —NH—CO—aryl, or a pharmaceutically acceptable salt or ester form thereof.

4. A compound according to claim 1 wherein the rings of the aryl or heteroaryl groups are optionally substituted by 1 to 3 groups selected from halogen, $C_1$-$C_4$ alkyl, $C_1$-$C_3$ perfluoroalkyl, —O—$C_1$-$C_3$ perfluoroalkyl, $C_1$-$C_3$ alkoxy, —OH, —$NH_2$, —CN or —NO2, or a pharmaceutically acceptable salt or ester form thereof.

5. A compound according to claim 1 wherein $R_2$ and $R_3$ are, independently, hydrogen, —OH, halogen, O(CO)-aryl [optionally substituted with $CF_3$, phenyl, —$OCH_3$ or t-butyl], —O($CH_2$)-aryl [optionally substituted with $CF_3$], or —NH (CO)-aryl [optionally substituted with t-butyl, $CF_3$, —$OCF_3$ or phenyl], or a pharmaceutically acceptable salt or ester form thereof.

6. A compound according to claim 1 wherein $R_4$ is hydrogen or $C_1$-$C_6$ alkyl, or a pharmaceutically acceptable salt or ester form thereof.

7. A compound according to claim 1 wherein $R_5$ is hydrogen, aryl, t-butyl, or $CF_3$ or a pharmaceutically acceptable salt or ester form thereof.

8. A compound according to claim 1 wherein $R_6$ is hydrogen, aryl, t-butyl, or $CF_3$ or a pharmaceutically acceptable salt or ester form thereof.

9. A compound as claimed in claim 1 having the formula:

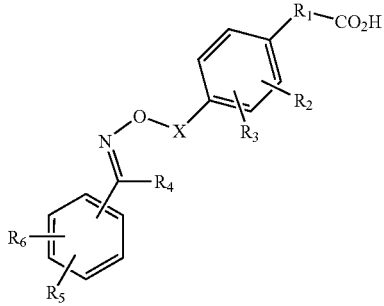

or a pharmaceutically acceptable salt or ester form thereof.

10. The compound of claim 1 that is (4-{3-[1-(4-tert-butyl-phenyl)-ethylideneaminooxy]-propoxy}-phenyl)-acetic acid or a pharmaceutically acceptable salt or ester form thereof; {4-[3-(4-tert-butyl-benzylideneaminooxy)-propoxy]-phenyl}-acetic acid or a pharmaceutically acceptable salt or ester form thereof; or 4-{2-[({(E)-1-[4-(tert-butyl)-phenyl]-ethylidene}amino)oxy]-ethoxy}-2-hydroxy-benzoic acid or a pharmaceutically acceptable salt or ester form thereof.

11. The compound of claim 1 that is 2-{[4-(tert-butyl) benzoyl]oxy}-4-[2-({1-phenylethylidene]amino}oxy) ethoxy]benzoic acid or a pharmaceutically acceptable salt or ester form thereof; 4-{2-[({[4-(tert-butyl) phenyl] methylidene}amino)oxy]-ethoxy}-2-hydroxybenzoic acid or a pharmaceutically acceptable salt or ester form thereof; 4-{2-[({(E)-[4-(tert-butyl)phenyl]methylidene}amino)oxy]-ethoxy}-2-{[4-(trifluoromethyl)benzoyl]oxy}benzoic acid or a pharmaceutically acceptable salt or ester form thereof; 4-{2-[({(E)-[4-(tert-butyl)phenyl]methyiidene}amino)oxy]ethoxy}-2-[(4-methoxy benzoyl)oxy]benzoic acid or a pharmaceutically acceptable salt or ester form thereof or 2-{[4-(tert-butyl)benzoyl]oxy}-4-{2-[({(E)-[4-(tert-butyl) phenyl] methylidene}amino)oxy]ethoxy}benzoic acid or a pharmaceutically acceptable salt or ester form thereof.

12. The compound of claim 1 that is 2-(Benzoyloxy)-4-{2-[({(E)-[4-(tert-butyl) phenyl]methylidene}amino)oxy]ethoxy}benzoic acid or a pharmaceutically acceptable salt or ester form thereof; 4-{2-[({(E)-1-[4-(tert-butyl)phenyl] ethylidene}amino)oxy]-ethoxy}-3-chloro-benzoic acid or a pharmaceutically acceptable salt or ester form thereof; 4-{2-[({(E)-1-[4-(tert-butyl)phenyl]ethylidene}amino)oxy]-ethoxy}-2-chloro-benzoic acid or a pharmaceutically acceptable salt or ester form thereof; 4-{2-[({[4-(tert-butyl)phenyl] methylidene}amino)oxy]ethoxy}-2-{[4-(trifluoromethyl) benzoyl]oxy}benzoic acid or a pharmaceutically acceptable salt or ester form thereof or 2-[([1,1'-biphenyl]-4-ylcarbonyl) oxy]-4-[2-({[(E)-1-phenylethylidene]amino}oxy)ethoxy] benzoic acid or a pharmaceutically acceptable salt or ester form thereof.

13. The compound of claim 1 that is 3-(4-{3-[({(E)-[4-(tert-butyl)phenyl]methylidene}amino)oxy] propoxy}phenyl)propanoic acid or a pharmaceutically acceptable salt or ester form thereof; 4-(tert-butyl)benzaldehyde O-{3-[4-(1H-tetraazol-5-ylmethyl)-phenoxy]-propyl}oxime or a pharmaceutically acceptable salt or ester form thereof; 2-{[4-(tert-butyl )benzoyl]amino}-4-{3-[({(E)-[4-(tert -butyl)phenyl]methylidene}amino)oxy] propoxy}benzoic acid or a pharmaceutically acceptable salt or ester form thereof; 4-{3-[({(E)-[3,5-bis(trifluoromethyl) phenyl]methylidene}amino)oxy]propoxy}-2-hydroxybenzoic acid or a pharmaceutically acceptable salt or ester form thereof or 4-[3-({[(1E)-1,1'-biphenyl-4-ylmethylidene] amino}oxy)propoxy]-2-{[4-(trifluoromethyl) benzoyl] amino}benzoic acid or a pharmaceutically acceptable salt or ester form thereof.

14. The compound of claim 1 that is 4-[3-({[(1E)-1-(4-tert-butylphenyl)propylidene]amino}oxy)propoxy]-2-{[4-(trifluoromethyl)benzoyl]amino}benzoic acid or a pharmaceutically acceptable salt or ester form thereof; 2-{[4-(trifluoromethyl) benzoyl]amino}-4-{3-[({(1E)-[4-(trifluoromethyl) phenyl]methylidene}amino)oxy] propoxy}benzoic acid or a pharmaceutically acceptable salt or ester form thereof; 4-[3-({[(1E)-1-phenylethylidene] amino}oxy)propoxy]-2-{[4-(trifluoromethyl)benzoyl] amino}benzoic acid or a pharmaceutically acceptable salt or ester form thereof; 4-[3-({[(1E)-(4-tert-butylphenyl)methylidene]amino}oxy)propoxy]-2-{[2-(trifluoromethyl)benzoyl]amino}benzoic acid or a pharmaceutically acceptable salt or ester form thereof or 2-{[2-(Trifluoromethyl) benzoyl] amino}-4-{3-[({(1E)-[4-(trifluoromethyl) phenyl] methylidene}amino)oxy]propoxy}benzoic acid or a pharmaceutically acceptable salt or ester form thereof.

15. The compound of claim 1 that is 4-[3-({[(1E)-1,1'-biphenyl-4-ylmethylidene]amino}oxy)propoxy]-2-{[2-(trifluoromethyl)benzoyl]amino}benzoic acid or a pharmaceutically acceptable salt or ester form thereof; 2-{[3,5-bis (trifluoromethyl)benzoyl]amino}-4-[3-({[(1E)-(4-tert-butylphenyl)methylidene]amino}oxy)propoxy]benzoic acid or a pharmaceutically acceptable salt or ester form thereof;

4-{3-[({(1E)-[3,5-bis(trifluoromethyl)phenyl]methylidene}amino)oxy]propoxy}-2-{[4-(trifluoromethoxy)benzoyl]amino}benzoic acid or a pharmaceutically acceptable salt or ester form thereof; 4-[3-({[(1E)-1,1'-biphenyl-4-yl methylidene]amino}oxy)propoxyl-2-{[4-(trifluoromethoxy)benzoyl]amino}benzoic acid or a pharmaceutically acceptable salt or ester form thereof or 2-{[4-(trifluoromethoxy)benzoyl]amino}-4-{3-[({(1E)-[4-(trifluoromethyl)phenyl]methylidene}amino)oxy]propoxy}benzoic acid or a pharmaceutically acceptable salt or ester form thereof.

16. The compound of claim 1 that is 4-[3-({[(1E)-1,1'-biphenyl-4-ylmethylidene]amino}oxy)propoxy]-2-{[3,5-bis(trifluoromethyl)benzoyl]amino}benzoic acid or a pharmaceutically acceptable salt or ester form thereof; 2-{[3,5-bis(trifluoromethyl)benzoyl]amino}-4-{3-[({(1E)-[4-(trifluoromethyl)phenyl]methylidene}amino)oxy]propoxy}benzoic acid or a pharmaceutically acceptable salt or ester form thereof; 2-bromo-4-[({[(1E)-(4-tert-butylphenyl)methylidene]amino}oxy)methyl]benzoic acid or a pharmaceutically acceptable salt or ester form thereof; 4-[3-({[(1E)-(4-tert-butylphenyl)methylidene]amino}oxy)propoxy]-2-(2-naphthoylamino)benzoic acid or a pharmaceutically acceptable salt or ester form thereof or 2-{[(2E)-3-(1'-biphenyl-4-yl)prop-2-enoyl]amino}-4-[3-({[(1E)-(4-tert-butylphenyl)methylidene]amino}oxy)propoxy]-benzoic acid or a pharmaceutically acceptable salt or ester form thereof.

17. The compound of claim 1 that is 2-[(1,1'-biphenyl-4-ylcarbonyl)amino]-4-[3-({[(1E)-(4-tert-butylphenyl)methylidene]amino}oxy)propoxy]benzoic acid or a pharmaceutically acceptable salt or ester form thereof.

18. The compound of claim 1 that is {4-[1-4-tert-butylphenyl)ethylideneaminooxymethyl]-phenyl}-acetic acid or a pharmaceutically acceptable salt or ester thereof or [4-(4-tert-butyl-benzylideneaminooxymethyl)-phenyl]-acetic acid or a pharmaceutically acceptable salt or ester form thereof.

19. The compound of claim 1 wherein $R_2$ is hydrogen, halogen, —O(CH$_2$)$_p$-aryl, —NH(CO)-aryl, —O(CO)-aryl, —O(CO)-heteroaryl or —NH(CO)—CH═CH-aryl and $R_3$ is hydrogen; or a pharmaceutically acceptable salt or ester form thereof.

20. The compound of claim 1 wherein $R_1$ is a direct bond to A or unsubstituted $C_1$-$C_3$ alkylene;

$R_2$ is hydrogen, halogen, $C_1$-$C_3$ alkyl, $C_1$-$C_3$ perfluoroalkyl, —O—$C_{1-C3}$ perfluoroalkyl, $C_1$-$C_3$ alkoxy, —OH, —O(CH$_2$)$_p$-aryl, aryl, heteroaryl, —NH(CO)-aryl, or —NH(CO)-heteroaryl;

$R_3$ is hydrogen, halogen, $C_1$-$C_3$ alkyl, $C_1$-$C_3$ perfluoroalkyl, —O—$C_1$-$C_3$ perfluoroalkyl, $C_1$-$C_3$ alkoxy, —OH, —O(CH$_2$)$_p$-aryl, aryl, heteroaryl, —NH(CO)-aryl, or —NH(CO)-heteroaryl;

$R_4$ is hydrogen, $C_1$-$C_4$ alkyl;

$R_5$ is hydrogen, halogen, $C_1$-$C_6$ alkyl, $C_1$-$C_6$ perfluoroalkyl, —O—$C_1$-$C_6$ perfluoroalkyl, $C_1$-$C_6$ alkoxy;

$R_6$ is hydrogen, halogen, $C_1$-$C_6$ alkyl, $C_1$-$C_6$ perfluoroalkyl, —O—$C_1$-$C_6$ perfluoroalkyl, $C_1$-$C_6$ alkoxy;

A is COOH or tetrazole; and

X is —CH$_2$, —CH$_2$—CH$_2$—O, or —CH$_2$—CH$_2$—CH$_2$—O;

or a pharmaceutically acceptable salt or ester form thereof.

21. A pharmaceutical composition comprising a pharmaceutically effective amount of a compound of claim 1, or a pharmaceutically acceptable salt or ester form thereof, and a pharmaceutically acceptable excipient or carrier.

* * * * *

UNITED STATES PATENT AND TRADEMARK OFFICE
CERTIFICATE OF CORRECTION

PATENT NO. : 7,420,083 B2
APPLICATION NO. : 10/948611
DATED : September 2, 2008
INVENTOR(S) : Lisa Marie Havran et al.

It is certified that error appears in the above-identified patent and that said Letters Patent is hereby corrected as shown below:

1) Column 51, lines 56-65, Claim 1: Please replace the chemical formula:

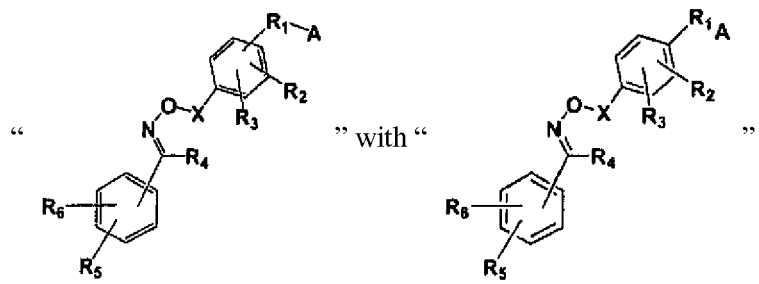

2) Column 53, line 22, Claim 4: Please replace "-NO2" with "-NO$_2$".

3) Column 54, line 7, Claim 11: Please correct typographical error "ii" in "4-{2-[({(E)-[4-(tert-butyl)phenyl]methy<u>ii</u>dene}amino)oxy]ethoxy}-2-[(4-methoxy benzoyl)oxy]benzoic acid" with "li" in "4-{2-[({(E)-[4-(tert-butyl)phenyl]methy<u>li</u>dene}amino)oxy]ethoxy}-2-[(4-methoxy benzoyl)oxy]benzoic acid".

4) Column 56, line 12, Claim 20: Please replace "-O-C$_{1-C3}$ perfluoroalkyl" with "-O-C$_1$-C$_3$ perfluoroalkyl".

Signed and Sealed this

Second Day of June, 2009

JOHN DOLL
*Acting Director of the United States Patent and Trademark Office*